(12) United States Patent
Cao et al.

(10) Patent No.: US 11,833,174 B2
(45) Date of Patent: Dec. 5, 2023

(54) MODIFIED CELL WITH ENHANCED FUNCTIONALITY AND CELLULAR THERAPY THEREOF

(71) Applicants: Innovative Cellular Therapeutics Holdings, Ltd., Grand Cayman (KY); Innovative Cellular Therapeutics, Inc., Rockville, MD (US)

(72) Inventors: Zhiyuan Cao, Shanghai (CN); Chengfei Pu, Shanghai (CN); Dongqi Chen, Shanghai (CN); Wei Ding, Shanghai (CN)

(73) Assignees: Innovative Cellular Therapeutics Holdings, Ltd., George Town (KY); Innovative Cellular Therapeutics, Inc., Rockville, MD (US)

( * ) Notice: Subject to any disclaimer, the term of this patent is extended or adjusted under 35 U.S.C. 154(b) by 423 days.

(21) Appl. No.: 17/023,835

(22) Filed: Sep. 17, 2020

(65) Prior Publication Data
US 2021/0077528 A1    Mar. 18, 2021

Related U.S. Application Data

(60) Provisional application No. 62/914,678, filed on Oct. 14, 2019, provisional application No. 62/905,082, filed on Sep. 24, 2019, provisional application No. 62/901,530, filed on Sep. 17, 2019, provisional application No. 62/901,494, filed on Sep. 17, 2019.

(51) Int. Cl.
*A61K 35/17* (2015.01)
*C07K 14/725* (2006.01)
*C07K 14/705* (2006.01)
*C07K 16/30* (2006.01)
*C07K 16/40* (2006.01)

(52) U.S. Cl.
CPC .......... *A61K 35/17* (2013.01); *C07K 14/7051* (2013.01); *C07K 14/70578* (2013.01); *C07K 16/3007* (2013.01); *C07K 16/3053* (2013.01); *C07K 16/40* (2013.01); *C07K 2319/03* (2013.01)

(58) Field of Classification Search
None
See application file for complete search history.

(56) References Cited

U.S. PATENT DOCUMENTS

2005/0233958 A1*  10/2005  Ni .................. C07K 16/2878
                                           514/18.9
2006/0228352 A1*  10/2006  Schoenberger ........ A61P 25/00
                                           424/143.1
2008/0138280 A1*  6/2008   Bauer ............... A61K 47/551
                                           424/1.77

FOREIGN PATENT DOCUMENTS

WO    WO-2020028444 A1 *  2/2020  .......... A61K 31/496

* cited by examiner

*Primary Examiner* — Brad Duffy
(74) *Attorney, Agent, or Firm* — Lee & Hayes P.C.

(57) ABSTRACT

Embodiments relate to a modified cell comprising a polynucleotide encoding a dominant negative form of Death receptor 5 (DR5). In embodiments, the modified cell further comprises a chimeric antigen receptor (CAR) and/or a modified TCR.

17 Claims, 13 Drawing Sheets
Specification includes a Sequence Listing.

MODIFIED CELL WITH ENHANCED FUNCTIONALITY AND CELLULAR THERAPY THEREOF

CROSS REFERENCE TO RELATED APPLICATIONS

This application claims the benefit of U.S. Provisional Application 62/901,494, filed Sep. 17, 2019; U.S. Provisional Application 62/901,530, filed Sep. 17, 2019; U.S. Provisional Application 62/905,082, filed Sep. 24, 2019; and U.S. Provisional Application 62/914,678, filed Oct. 14, 2019, which are hereby all incorporated by reference in their entirety.

SEQUENCE LISTING INFORMATION

A computer-readable textfile, entitled "SDS1.0085US_ST25.txt," created on or about Sep. 17, 2020, with a file size of about 111 KB, contains the sequence listing for this application and is hereby incorporated by reference in its entirety.

TECHNICAL FIELD

The present disclosure relates to compositions and methods of using T cell therapy to treat diseases such as cancer.

BACKGROUND

T cells genetically targeted to certain malignancies have demonstrated tremendous clinical outcomes. During CAR-T cell therapy, physicians draw patients' blood and harvest their cytotoxic T cells. The cells are re-engineered in a lab to attack the patient's particular cancer. Recent progress in genome editing technologies allows scientists to disrupt gene expression in T-cells in order to enhance effector functions or to bypass tumor immune suppression and metabolically hostile tumor microenvironment. Thus, there is a need to modulate T cells to overcome these problems.

SUMMARY

Embodiments relate to a modified cell comprising a polynucleotide encoding a dominant negative form of Death receptor 5 (DR5). Embodiments relate to a pharmaceutical composition comprising a population of the modified cells. Embodiments relate to a method of causing or eliciting T cell response in a subject in need thereof and/or treating a tumor of the subject, the method comprising administering an effective amount of the composition to the subject. Embodiments relate to a nucleotide acid sequence comprising the polynucleotide encoding the dominant negative form of DR5. Embodiments relate to a method of enhancing T cell response, the method comprising: a population of modified cells, the modified cells comprising a CAR; contacting target cells with the population of modified cells, wherein the CAR comprises a binding domain that binds the target cells; and measuring a level of the T cell response, wherein the T cell response is greater than that of a population of modified cells that comprises the CAR but doesn't comprise the polynucleotide encoding DR5.

This Summary is not intended to identify key features or essential features of the claimed subject matter, nor is it intended to be used to limit the scope of the claimed subject matter.

BRIEF DESCRIPTION OF THE DRAWINGS

The Detailed Description is described with reference to the accompanying figures. The use of the same reference numbers in different figures indicates similar or identical items.

DETAILED DESCRIPTION

Figure 1:
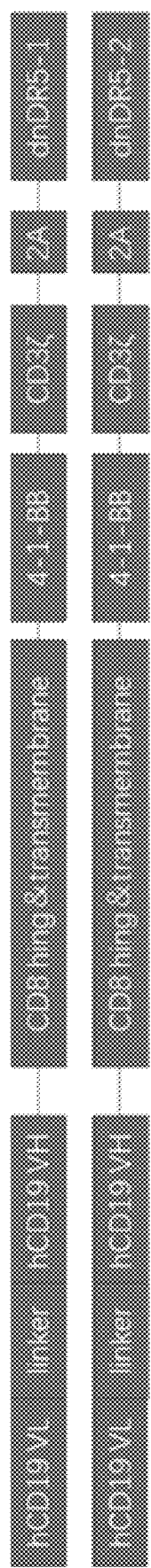
FIG. 1 shows structures of vectors encoding CD19 CAR and dnDR5.

Unless defined otherwise, all technical and scientific terms used herein have the same meaning as commonly understood by those of ordinary skill in the art to which the disclosure belongs. Although any methods and materials similar or equivalent to those described herein can be used in the practice or testing of the present disclosure, preferred methods and materials are described. For the purposes of the present disclosure, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight, or length that varies by as much as 20, 15, 10, 9, 8, 7, 6, 5, 4, 3, 2 or 1% to a reference quantity, level, value, number, frequency, percentage, dimension, size, amount, weight or length.

The term "activation," as used herein, refers to the state of a cell that has been sufficiently stimulated to induce detectable cellular proliferation. Activation can also be associated with induced cytokine production and detectable effector functions. The term "activated T cells" refers to, among other things, T cells that are undergoing cell division.

The term "antibody" is used in the broadest sense and refers to monoclonal antibodies (including full length monoclonal antibodies), polyclonal antibodies, multi-specific antibodies (e.g., bispecific antibodies), and antibody fragments so long as they exhibit the desired biological activity or function. The antibodies in the present disclosure may exist in a variety of forms including, for example, polyclonal antibodies, monoclonal antibodies, Fv, Fab and F(ab)$_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antibody fragments" refers to a portion of a full length antibody, for example, the antigen binding or variable region of the antibody. Other examples of antibody fragments include Fab, Fab', F(ab')2, and Fv fragments; diabodies; linear antibodies; single-chain antibody molecules; and multi-specific antibodies formed from antibody fragments.

The term "Fv" refers to the minimum antibody fragment which contains a complete antigen-recognition and -binding site. This fragment consists of a dimer of one heavy- and one light-chain variable region domain in tight, non-covalent association. From the folding of these two domains emanates six hypervariable loops (3 loops each from the H and L chain) that contribute the amino acid residues for antigen binding and confer antigen binding specificity to the antibody. However, even a single variable domain (or half of a Fv including only three complementarity determining regions (CDRs) specific for an antigen) has the ability to recognize and bind antigen, although at a lower affinity than the entire binding site (the dimer).

An "antibody heavy chain," as used herein, refers to the larger of the two types of polypeptide chains present in all antibody molecules in their naturally occurring conformations. An "antibody light chain," as used herein, refers to the smaller of the two types of polypeptide chains present in all antibody molecules in their naturally occurring conformations. K and A light chains refer to the two major antibody light chain isotypes.

The term "synthetic antibody" refers to an antibody which is generated using recombinant DNA technology, such as, for example, an antibody expressed by a bacteriophage. The term also includes an antibody which has been generated by the synthesis of a DNA molecule encoding the antibody and the expression of the DNA molecule to obtain the antibody, or to obtain an amino acid encoding the antibody. The synthetic DNA is obtained using technology that is available and well known in the art.

The term "antigen" refers to a molecule that provokes an immune response, which may involve either antibody production, or the activation of specific immunologically-competent cells, or both. Antigens include any macromolecule, including all proteins or peptides, or molecules derived from recombinant or genomic DNA. For example, DNA including a nucleotide sequence or a partial nucleotide sequence encoding a protein or peptide that elicits an immune response, and therefore, encodes an "antigen" as the term is used herein. An antigen need not be encoded solely by a full-length nucleotide sequence of a gene. An antigen can be generated, synthesized or derived from a biological sample including a tissue sample, a tumor sample, a cell, or a biological fluid.

The term "anti-tumor effect" as used herein, refers to a biological effect associated with a decrease in tumor volume, a decrease in the number of tumor cells, a decrease in the number of metastases, decrease in tumor cell proliferation, decrease in tumor cell survival, an increase in life expectancy of a subject having tumor cells, or amelioration of various physiological symptoms associated with the cancerous condition. An "anti-tumor effect" can also be manifested by the ability of the peptides, polynucleotides, cells, and antibodies in the prevention of the occurrence of tumor in the first place.

The term "auto-antigen" refers to an antigen mistakenly recognized by the immune system as being foreign. Auto-antigens include cellular proteins, phosphoproteins, cellular surface proteins, cellular lipids, nucleic acids, glycoproteins, including cell surface receptors.

The term "autologous" is used to describe a material derived from a subject which is subsequently re-introduced into the same subject.

The term "allogeneic" is used to describe a graft derived from a different subject of the same species. As an example, a donor subject may be a related or unrelated or recipient subject, but the donor subject has immune system markers which are similar to the recipient subject.

The term "xenogeneic" is used to describe a graft derived from an subject of a different species. As an example, the donor subject is from a different species than a recipient subject and the donor subject and the recipient subject can be genetically and immunologically incompatible.

The term "cancer" as used to refer to a disease characterized by the rapid and uncontrolled growth of aberrant cells. Cancer cells can spread locally or through the bloodstream and lymphatic system to other parts of the body. Examples of various cancers include breast cancer, prostate cancer, ovarian cancer, cervical cancer, skin cancer, pancreatic cancer, colorectal cancer, renal cancer, liver cancer, brain cancer, lymphoma, leukemia, lung cancer, and the like.

Throughout this specification, unless the context requires otherwise, the words "comprise," "includes" and "including" will be understood to imply the inclusion of a stated step or element or group of steps or elements but not the exclusion of any other step or element or group of steps or elements.

The phrase "consisting of" is meant to include, and is limited to, whatever follows the phrase "consisting of." Thus, the phrase "consisting of" indicates that the listed elements are required or mandatory and that no other elements may be present.

The phrase "consisting essentially of" is meant to include any elements listed after the phrase and can include other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands.

The term "corresponds to" or "corresponding to" refers to (a) a polynucleotide having a nucleotide sequence that is substantially identical or complementary to all or a portion of a reference polynucleotide sequence or encoding an amino acid sequence identical to an amino acid sequence in a peptide or protein; or (b) a peptide or polypeptide having an amino acid sequence that is substantially identical to a sequence of amino acids in a reference peptide or protein.

The term "co-stimulatory ligand," refers to a molecule on an antigen presenting cell (e.g., an APC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including at least one of proliferation, activation, differentiation, and other cellular responses. A co-stimulatory ligand can include B7-1 (CD80), B7-2 (CD86), PD-L1, PD-L2, 4-1BBL, OX40L, inducible co-stimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, a ligand for CD7, an agonist or antibody that binds the Toll ligand receptor and a ligand that specifically binds with B7-H3. A co-stimulatory ligand also includes, inter alia, an agonist or an antibody that specifically binds with a co-stimulatory molecule present on a T cell, such as CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds CD83.

The term "co-stimulatory molecule" refers to the cognate binding partner on a T cell that specifically binds with a co-stimulatory ligand, thereby mediating a co-stimulatory response by the T cell, such as proliferation. Co-stimulatory molecules include an MHC class I molecule, BTLA, and a Toll-like receptor.

The term "co-stimulatory signal" refers to a signal, which in combination with a primary signal, such as TCR/CD3 ligation, leads to T cell proliferation and/or upregulation or downregulation of key molecules. The terms "disease" and "condition" may be used interchangeably or may be different in that the particular malady or condition may not have a known causative agent (so that etiology has not yet been worked out), and it is therefore not yet recognized as a disease but only as an undesirable condition or syndrome, wherein a more or less specific set of symptoms have been identified by clinicians. The term "disease" is a state of health of a subject wherein the subject cannot maintain homeostasis, and wherein if the disease is not ameliorated then the subject's health continues to deteriorate. In contrast, a "disorder" in a subject is a state of health in which the animal is able to maintain homeostasis, but in which the animal's state of health is less favorable than it would be in the absence of the disorder. Left untreated, a disorder does not necessarily cause a further decrease in the animal's state of health.

The term "effective" refers to adequate to accomplish a desired, expected, or intended result. For example, an "effective amount" in the context of treatment may be an amount of a compound sufficient to produce a therapeutic or prophylactic benefit.

The term "encoding" refers to the inherent property of specific sequences of nucleotides in a polynucleotide, such as a gene, a cDNA, or an mRNA, to serve as templates for the synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence (except that a "T" is replaced by a "U") and is usually provided in sequence listings, and the non-coding strand, used as the template for transcription of a gene or cDNA, can be referred to as encoding the protein or other product of that gene or cDNA.

The term "exogenous" refers to a molecule that does not naturally occur in a wild-type cell or organism but is typically introduced into the cell by molecular biological techniques. Examples of exogenous polynucleotides include vectors, plasmids, and/or man-made nucleic acid constructs encoding the desired protein. With regard to polynucleotides and proteins, the term "endogenous" or "native" refers to naturally-occurring polynucleotide or amino acid sequences that may be found in a given wild-type cell or organism. Also, a particular polynucleotide sequence that is isolated from a first organism and transferred to a second organism by molecular biological techniques is typically considered an "exogenous" polynucleotide or amino acid sequence with respect to the second organism. In specific embodiments, polynucleotide sequences can be "introduced" by molecular biological techniques into a microorganism that already contains such a polynucleotide sequence, for instance, to create one or more additional copies of an otherwise naturally-occurring polynucleotide sequence, and thereby facilitate overexpression of the encoded polypeptide.

In embodiments, the polynucleotide may integrate into the genome of the modified cell, and descendants of the modified cell will also express the polynucleotide, resulting in a stably transfected modified cell. In embodiments, the modified cell may express the polynucleotide encoding the CAR, but the polynucleotide does not integrate into the genome of the modified cell such that the modified cell expresses the transiently transfected polynucleotide for a finite period of time (e.g., several days), after which the polynucleotide is lost through cell division or other factors. For example, the polynucleotide is present in the modified cell in a recombinant DNA construct, in an mRNA, or in a viral vector, and/or the polynucleotide is an mRNA, which is not integrated into the genome of the modified cell.

The term "expression" refers to the transcription and/or translation of a particular nucleotide sequence driven by its promoter.

The term "expression vector" refers to a vector including a recombinant polynucleotide including expression control sequences operably linked to a nucleotide sequence to be expressed. An expression vector includes sufficient cis-acting elements for expression; other elements for expression can be supplied by the host cell or in an in vitro expression system. Expression vectors include all those known in the art, such as cosmids, plasmids (e.g., naked or contained in liposomes), and viruses (e.g., lentiviruses, retroviruses, adenoviruses, and adeno-associated viruses) that incorporate the recombinant polynucleotide.

The term "homologous" refers to sequence similarity or sequence identity between two polypeptides or between two polynucleotides when a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared× 100. For example, if 6 of 10 of the positions in two sequences are matched or homologous, then the two sequences are 60% homologous. By way of example, the DNA sequences ATTGCC and TATGGC share 50% homology. A comparison is made when two sequences are aligned to give maximum homology.

The term "immunoglobulin" or "Ig," refers to a class of proteins, which function as antibodies. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function but may serve as an antigen receptor. IgE is the immunoglobulin that mediates immediate hypersensitivity by causing the release of mediators from mast cells and basophils upon exposure to the allergen.

The term "isolated" refers to a material that is substantially or essentially free from components that normally accompany it in its native state. The material can be a cell or a macromolecule such as a protein or nucleic acid. For example, an "isolated polynucleotide," as used herein, refers to a polynucleotide, which has been purified from the sequences which flank it in a naturally-occurring state, e.g., a DNA fragment which has been removed from the sequences that are normally adjacent to the fragment. Alternatively, an "isolated peptide" or an "isolated polypeptide" and the like, as used herein, refer to in vitro isolation and/or purification of a peptide or polypeptide molecule from its natural cellular environment, and from association with other components of the cell.

The term "substantially purified" refers to a material that is substantially free from components that are normally associated with it in its native state. For example, a substantially purified cell refers to a cell that has been separated from other cell types with which it is normally associated in its naturally occurring or native state. In some instances, a population of substantially purified cells refers to a homogenous population of cells. In other instances, this term refers simply to a cell that has been separated from the cells with which they are naturally associated in their natural state. In embodiments, the cells are cultured in vitro. In other embodiments, the cells are not cultured in vitro.

In the context of the present disclosure, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may, in some version, contain an intron(s).

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. Moreover, the use of lentiviruses enables the integration of the genetic information into the host chromosome, resulting in stably transduced genetic information. HIV, SIV, and FIV are all examples of lentiviruses. Vectors derived from lentiviruses offer the means to achieve significant levels of gene transfer in vivo.

The term "modulating" refers to mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response, thereby mediating a beneficial therapeutic response in a subject, preferably, a human.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation.

The term "under transcriptional control" refers to a promoter being operably linked to and in the correct location and orientation in relation to a polynucleotide to control the initiation of transcription by RNA polymerase and expression of the polynucleotide.

The term "overexpressed" tumor antigen or "overexpression" of the tumor antigen is intended to indicate an abnormal level of expression of the tumor antigen in a cell from a disease area such as a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme), astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma, and brain metastases).

Lymphocyte or T cell response in a subject refers to cell-mediated immunity associated with a helper, killer, regulatory, and other types of T cells. For example, T cell response may include activities such as assisting other WBCs in immunologic processes and identifying and destroying virus-infected cells and tumor cells. T cell response in the subject can be measured via various indicators such as a number of virus-infected cells and/or tumor cells that T cells kill, the amount of cytokines (e.g., IL-6 and IFN-γ) that T cells release in vivo and/or in co-culturing with virus-infected cells and/or tumor cells, indicates a level of proliferation of T cells in the subject, a phenotype change of T cells, for example, changes to memory T cells, and a level of longevity or lifetime of T cells in the subject.

In embodiments, the method of enhancing T cell response described herein can effectively treat a subject in need thereof, for example, a subject diagnosed with a tumor or inhibit the growth of target cells. The term tumor refers to a mass, which can be a collection of fluid, such as blood, or a solid mass. A tumor can be malignant (cancerous) or benign. Examples of blood cancers include chronic lymphocytic leukemia, acute myeloid leukemia, acute lymphoblastic leukemia, and multiple myeloma.

A solid tumor antigen is an antigen expressed on a solid tumor. In embodiments, solid tumor antigens are also expressed at low levels on healthy tissue. Examples of solid tumor antigens and their related disease tumors are provided in Table 1.

TABLE 1

| Solid Tumor antigen | Disease tumor |
| --- | --- |
| PRLR | Breast Cancer |
| CLCA1 | colorectal cancer |
| MUC12 | colorectal cancer |
| GUCY2C | colorectal cancer and other digestive cancer types |
| GPR35 | colorectal cancer |
| CR1L | Gastric Cancer |
| MUC 17 | Gastric Cancer |
| TMPRSS11B | esophageal cancer |
| MUC21 | esophageal cancer |
| TMPRSS11E | esophageal cancer |
| CD207 | bladder Cancer |
| SLC30A8 | pancreatic Cancer |
| CFC1 | pancreatic Cancer |
| SLC12A3 | Cervical Cancer |
| SSTR1 | Cervical tumor |
| GPR27 | Ovary tumor |
| FZD10 | Ovary tumor |
| TSHR | Thyroid Tumor |
| SIGLEC15 | Urothelial cancer |
| SLC6A3 | Renal cancer |
| KISS1R | Renal cancer |
| QRFPR | Renal cancer: |
| GPR119 | Pancreatic cancer |
| CLDN6 | Endometrial cancer/Urothelial cancer |
| UPK2 | Urothelial cancer (including bladder cancer) |
| ADAM12 | Breast cancer, pancreatic cancer, and the like |
| SLC45A3 | Prostate cancer |
| ACPP | Prostate cancer |
| MUC21 | Esophageal cancer |
| MUC16 | Ovarian cancer |
| MS4A12 | Colorectal cancer |
| ALPP | Endometrial cancer |
| CEA | Colorectal carcinoma |
| EphA2 | Glioma |
| FAP | Mesothelioma |
| GPC3 | Lung squamous cell carcinoma |

TABLE 1-continued

| Solid Tumor antigen | Disease tumor |
| --- | --- |
| IL13-Rα2 | Glioma |
| Mesothelin | Metastatic cancer |
| PSMA | Prostate cancer |
| ROR1 | Breast lung carcinoma |
| VEGFR-II | Metastatic cancer |
| GD2 | Neuroblastoma |
| FR-α | Ovarian carcinoma |
| ErbB2 | Carcinomas |
| EpCAM | Carcinoma |
| EGFRvIII | Glioma-Glioblastoma |
| EGFR | Glioma-NSCL cancer |
| tMUC1 | Cholangiocarcinoma, Pancreatic cancer, Breast |
| PSCA | pancreas, stomach, or prostate cancer |
| FCER2, GPR18, FCRLA, CXCR5, FCRL3, FCRL2, HTR3A, and CLEC17A | breast cancer |
| TRPMI, SLC45A2, and SLC24A5 | Lymphoma |
| DPEP3 | Melanoma |
| KCNK16 | ovarian, testis |
| LIM2 or KCNV2 | Pancreatic |
| SLC26A4 | thyroid cancer |
| CD171 | Neuroblastoma |
| Glypican-3 | Sarcoma |
| IL-13 | Glioma |
| CD79a/b | Lymphoma |
| MAGE A4 | Lung cancer and multiple cancer types |

The term "parenteral administration" of a composition includes, e.g., subcutaneous (s.c.), intravenous (i.v.), intramuscular (i.m.), intrasternal injection, or infusion techniques.

The terms "patient," "subject," and "individual," and the like are used interchangeably herein, and refer to any human, animal, or living organism, amenable to the methods described herein. In certain non-limiting embodiments, the patient, subject, or individual is a human or animal. In embodiments, the term "subject" is intended to include living organisms in which an immune response can be elicited (e.g., mammals). Examples of subjects include humans, and animals such as dogs, cats, mice, rats, and transgenic species thereof.

A subject in need of a treatment or in need thereof includes a subject having a disease, condition, or disorder that needs to be treated. A subject in need thereof also includes a subject that needs treatment for the prevention of a disease, condition, or disorder.

The term "polynucleotide" or "nucleic acid" refers to mRNA, RNA, cRNA, rRNA, cDNA, or DNA. The term typically refers to a polymeric form of nucleotides of at least 10 bases in length, either ribonucleotides or deoxynucleotides or a modified form of either type of nucleotide. The term includes all forms of nucleic acids including single and double stranded forms of nucleic acids.

The terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion, or substitution of at least one nucleotide. Accordingly, the terms "polynucleotide variant" and "variant" include polynucleotides in which one or more nucleotides have been added or deleted or replaced with different nucleotides. In this regard, it is well understood in the art that certain alterations inclusive of mutations, additions, deletions, and substitutions can be made to a reference polynucleotide whereby the altered polynucleotide retains the biological function or activity of the reference polynucleotide or has increased activity in relation to the reference polynucleotide (i.e., optimized). Polynucleotide variants include, for example, polynucleotides having at least 50% (and at least 51% to at least 99% and all integer percentages in between, e.g., 90%, 95%, or 98%) sequence identity with a reference polynucleotide sequence described herein. The terms "polynucleotide variant" and "variant" also include naturally-occurring allelic variants and orthologs.

The terms "polypeptide," "polypeptide fragment," "peptide," and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. In certain aspects, polypeptides may include enzymatic polypeptides, or "enzymes," which typically catalyze (i.e., increase the rate of) various chemical reactions.

The term "polypeptide variant" refers to polypeptides that are distinguished from a reference polypeptide sequence by the addition, deletion, or substitution of at least one amino acid residue. In certain embodiments, a polypeptide variant is distinguished from a reference polypeptide by one or more substitutions, which may be conservative or non-conservative. In certain embodiments, the polypeptide variant comprises conservative substitutions and, in this regard, it is well understood in the art that some amino acids may be changed to others with broadly similar properties without changing the nature of the activity of the polypeptide. Polypeptide variants also encompass polypeptides in which one or more amino acids have been added or deleted or replaced with different amino acid residues.

The term "promoter" refers to a DNA sequence recognized by the synthetic machinery of the cell or introduced synthetic machinery, required to initiate the specific transcription of a polynucleotide sequence. The term "expression control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

The term "bind," "binds," or "interacts with" refers to a molecule recognizing and adhering to a particular second molecule in a sample or organism but does not substantially recognize or adhere to other structurally unrelated molecules in the sample. The term "specifically binds," as used herein with respect to an antibody, refers to an antibody which recognizes a specific antigen, but does not substantially recognize or bind other molecules in a sample. For example, an antibody that specifically binds an antigen from one species may also bind that antigen from one or more species. But, such cross-species reactivity does not itself alter the classification of an antibody as specific. In another example, an antibody that specifically binds an antigen may also bind different allelic forms of the antigen. However, such cross reactivity does not itself alter the classification of an antibody as specific. In some instances, the terms "specific binding" or "specifically binding" can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds a specific protein structure rather than to any protein. If an antibody is specific for epitope "A," the presence of a molecule containing epitope A (or free, unlabeled A), in a reaction containing labeled "A" and the antibody, will reduce the amount of labeled A bound to the antibody.

A "binding protein" is a protein that is able to bind non-covalently to another molecule. A binding protein can bind to, for example, a DNA molecule (a DNA-binding protein), an RNA molecule (an RNA-binding protein), and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding, and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains can be "engineered" to bind to a predetermined nucleotide sequence, for example, via engineering (altering one or more amino acids) of the recognition helix region of a naturally occurring zinc finger protein. Further, a Zinc finger binding domain may be fused a DNA-cleavage domain to form a Zinc finger nuclease (ZFN) targeting a specific desired DNA sequence. For example, a pair of ZFNs (e.g., a ZFN-left arm and a ZFN-right arm) may be engineered to target and cause modifications of specific desired DNA sequences (e.g., TRAC genes), as illustrated in FIG. 1.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "target site" or "target sequence" is a nucleic acid sequence that defines a portion of a nucleic acid to which a binding molecule will bind, provided sufficient conditions for binding exist. For example, the sequence 5' GAATTC 3' is a target site for the Eco RI restriction endonuclease.

A "fusion" molecule is a molecule in which two or more subunit molecules are linked, preferably covalently. The subunit molecules can be the same chemical type of molecule or can be different chemical types of molecules. Examples of the first type of fusion molecule include, but are not limited to, fusion proteins (for example, a fusion between a ZFP DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage, and polypeptide ligation can also be involved in the expression of the protein in a cell. Methods for polynucleotide and polypeptide delivery to cells are presented elsewhere in this disclosure.

"Modulation" of gene expression refers to a change in the activity of a gene. Modulation of expression can include but is not limited to gene activation and gene repression. Genome editing (e.g., cleavage, alteration, inactivation, random mutation) can be used to modulate expression. Gene inactivation refers to any reduction in gene expression as compared to a cell that does not include a ZFP, as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

By "statistically significant," it is meant that the result was unlikely to have occurred by chance. Statistical significance can be determined by any method known in the art. Commonly used measures of significance include the p-value, which is the frequency or probability with which the observed event would occur if the null hypothesis were true. If the obtained p-value is smaller than the significance level, then the null hypothesis is rejected. In simple cases, the significance level is defined at a p-value of 0.05 or less. A "decreased" or "reduced" or "lesser" amount is typically a "statistically significant" or a physiologically significant amount, and may include a decrease that is about 1.1, 1.2, 1.3, 1.4, 1.5, 1.6 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 1.5, 1.6, 1.7. 1.8, etc.) an amount or level described herein.

The term "stimulation" refers to a primary response induced by binding of a stimulatory molecule (e.g., a TCR/CD3 complex) with its cognate ligand, thereby mediating a signal transduction event, such as signal transduction via the TCR/CD3 complex. Stimulation can mediate altered expression of certain molecules, such as downregulation of TGF-β and/or reorganization of cytoskeletal structures. CD3 zeta is not the only suitable primary signaling domain for a CAR construct with respect to the primary response. For example, back in 1993, both CD3 zeta and FcR gamma were shown as functional primary signaling domains of CAR molecules. Eshhar et al., "Specific activation and targeting of cytotoxic lymphocytes through chimeric single chains consisting of antibody-binding domains and the gamma or zeta subunits of the immunoglobulin and T-cell receptors" PNAS, 1993 Jan. 15; 90(2):720-4, showed that two CAR constructs in which an scFv was fused to "either the FcR γ chain or the CD3 complex s chain" triggered T cell activation and the target cell. Notably, as demonstrated in Eshhar et al., CAR constructs containing only the primary signaling domain CD3 zeta or FcR gamma are functional without the co-presence of co-stimulatory domains. Additional non-CD3 zeta based CAR constructs have been developed over the years. For example, Wang et al., "A Chimeric Antigen Receptor (CARs) Based Upon a Killer Immunoglobulin-Like Receptor (KIR) Trigger Robust Cytotoxic Activity in Solid Tumors" Molecular Therapy, vol. 22, no. Suppl.1, May 2014, page S57, tested a CAR molecule in which an scFv was fused to "the transmembrane and the cytoplasmic domain of" a killer immunoglobulin-like receptor (KIR). Wang et al. state that, "a KIR-based CAR targeting mesothelin (SS 1-KIR) triggers antigen-specific cytotoxic activity and cytokine production that is comparable to CD3—based CARs." A second publication from the same group, Wang et al., "Generation of Potent T-cell Immunotherapy for Cancer Using DAP12-Based, Multichain, Chimeric Immunoreceptors" Cancer Immunol Res. 2015 July; 3(7):815-26, showed that a CAR molecule in which "a single-chain variable fragment for antigen recognition [was fused] to the transmembrane and cytoplasmic domains of KIR2DS2, a stimulatory killer immunoglobulin-like receptor (KIR)" functioned both in vitro and in vivo "when introduced into human T cells with DAP12, an immunotyrosine-based activation motifs-containing adaptor."

The term "stimulatory molecule" refers to a molecule on a T cell that specifically binds a cognate stimulatory ligand present on an antigen presenting cell. For example, a functional signaling domain derived from a stimulatory molecule is the zeta chain associated with the T cell receptor complex.

The term "stimulatory ligand" refers to a ligand that, when present on an antigen presenting cell (e.g., an APC, a dendritic cell, a B-cell, and the like.) can specifically bind with a cognate binding partner (referred to herein as a "stimulatory molecule") on a cell, for example, a T cell, thereby mediating a primary response by the T cell, including activation, initiation of an immune response, proliferation, and similar processes. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "therapeutic" refers to a treatment and/or prophylaxis. A therapeutic effect is obtained by suppression, remission, or eradication of a disease state or alleviating the symptoms of a disease state.

The term "therapeutically effective amount" refers to the amount of the subject compound that will elicit the biological or medical response of a tissue, system, or subject that is being sought by the researcher, veterinarian, medical doctor, or another clinician. The term "therapeutically effective amount" includes that amount of a compound that, when administered, is sufficient to prevent the development of, or alleviate to some extent, one or more of the signs or symptoms of the disorder or disease being treated. The therapeutically effective amount will vary depending on the compound, the disease, and its severity and the age, weight, etc., of the subject to be treated.

The term "treat a disease" refers to the reduction of the frequency or severity of at least one sign or symptom of a disease or disorder experienced by a subject.

The term "transfected" or "transformed" or "transduced" refers to a process by which an exogenous nucleic acid is transferred or introduced into the host cell. A "transfected" or "transformed" or "transduced" cell is one which has been transfected, transformed, or transduced with the exogenous nucleic acid. The cell includes the primary subject cell and its progeny.

The term "vector" refers to a polynucleotide that comprises an isolated nucleic acid and which can be used to deliver the isolated nucleic acid to the interior of a cell. Numerous vectors are known in the art including linear polynucleotides, polynucleotides associated with ionic or amphiphilic compounds, plasmids, and viruses. Thus, the term "vector" includes an autonomously replicating plasmid or a virus. The term also includes non-plasmid and non-viral compounds that facilitate the transfer of nucleic acid into cells, such as polylysine compounds, liposomes, and the like. Examples of viral vectors include, adenoviral vectors, adeno-associated virus vectors, retroviral vectors, and others. For example, lentiviruses are complex retroviruses, which, in addition to the common retroviral genes gag, pol, and env, contain other genes with regulatory or structural function. Lentiviral vectors are well known in the art. Some examples of lentivirus include the Human Immunodeficiency Viruses: HIV-1, HIV-2, and the Simian Immunodeficiency Virus: SIV. Lentiviral vectors have been generated by multiply attenuating the HIV virulence genes, for example, the genes env, vif, vpr, vpu, and nef are deleted, making the vector biologically safe.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, and 6. This applies regardless of the breadth of the range.

Embodiments relate to a modified cell engineered to express an antigen binding molecule, wherein expression and/or function of one or more molecules in the modified cell has been reduced or eliminated, the one or more molecules associated with apoptosis of the modified cell. In embodiments, one or more molecules may include glucocorticoid receptor α (GRα), Fas, TNFR1, TNFR2, and/or TRAIL. In embodiments, the modified cell comprises a disruption in an endogenous gene or addition of an exogenous gene that is associated with a biosynthesis or transportation pathway of one or more molecules.

In embodiments, the amplification of T cells is enhanced by inhibiting the apoptosis of T cells. It acts primarily through the FAS, TNFR1/2, and TRAIL signaling pathways. Fas is a transmembrane protein belonging to the tumor necrosis factor receptor superfamily. Its binding to FasL can initiate apoptosis of apoptosis signals. Its activation involves a series of steps: first, the ligand induces receptor trimerization and then forms an apoptosis-inducing complex on the cell membrane, which includes the Fas-associated protein FADD with a death domain. The complex then polymerizes the molecules of multiple caspase8, which in turn causes a subsequent cascade reaction, namely Caspases, which is activated as a zymogen, causing the following cascade. The cells undergo apoptosis. The TNF-mediated apoptotic pathway is similar to FAS, which is mediated by the death receptor TNFRI. Tumor necrosis factor receptor (TNF Rs) is the representative family of the largest death receptors, including TNFRI (p55, CD120a), TNFRII (p75, CD120b), and the like. The common feature is that the intracellular region has a highly homologous amino acid sequence necessary for transducing cell death signals, namely DD. In recent years, the death domain proteins found mainly include FADD, TNFRI associated death domain protein (TRADD), and receptor interacting protein (RIP). TNF is mainly produced by infected and activated macrophages and T cells and mediates apoptosis through its cell surface receptors TNFRI and TNFRII. In embodiments, an apoptotic signal is a tumor necrosis factor related to apoptosis-induced ligand (TRAIL), which is a member of the tumor necrosis factor family and is capable of inducing apoptosis in most human tumor cells. There is no obvious cytotoxicity to normal cells. TRAIL induces tumor cell apoptosis mainly by activating exogenous pathways, accompanied by cascade amplification of endogenous pathways. After TRAIL binds to the death receptor on the cell membrane surface, the intramembranous segment of the death receptor activates and undergoes self-shearing to form death-inducing signaling complexes (DISCs). The recruitment of Fas-associated death domain (FADD) and caspase-8, caspase-10 precursors, is a prerequisite for the formation of DISCs. Caspase-8 and caspase-10 precursors form active cleaved caspase-8 and cleaved caspase-10, which in turn activates caspase-3, 6, and 7 and initiates apoptosis. In embodiments, dominant negative forms of FAS/TNFR1/2 and TRAIL or direct knockout/knock down (e.g., TALEN) may be used to inhibit T cell apoptosis. In embodiments, reducing of function or expression of downstream signals such as caspase8/3/fadd-caspase10 and PRKC may be implemented to inhibit apoptosis.

Dominant negative mutations have an altered gene product that acts antagonistically to the wild-type allele. These mutations usually result in an altered molecular function (often inactive) and are characterized by a dominant or semi-dominant phenotype. For example, the dominant negative form of the receptor may include one or more additions, deletions, or substitutions of the wide-type intracellular domain of the receptor such that a signaling pathway of the receptor may be blocked.

Embodiments relate to a method of expanding modified cells, the method comprising reducing or eliminating function or expression of the one or more molecules in the modified cells such that cell death of the modified cells induced by the one or more molecules are reduced as compared to the modified cells of which function of expression of the one or more molecules is not reduced or eliminated. In embodiments, reduced cell death achieves a similar effect (e.g, cell numbers) of those methods that directly increase cell numbers, which may also be considered as an expansion of the modified cells in the present application.

Embodiments relate to a modified cell engineered to express an antigen binding molecule, wherein expression and/or function of glucocorticoid receptor α (GRα) in the modified cell has been reduced or eliminated. Embodiments relate to a pharmaceutical composition comprising the population of the cells. Embodiments relate to a method of causing or eliciting T cell response in a subject in need thereof and/or treating a tumor of the subject, the method comprising administering an effective amount of the composition. For example, the modified cell comprises a disruption in an endogenous gene or addition of an exogenous gene that is associated with a biosynthesis or transportation pathway of GRα.

In embodiments, the antigen binding molecule is the chimeric antigen receptor (CAR), which comprises an antigen-binding domain, a transmembrane domain, and an intracellular signaling domain. In embodiments, the antigen-binding domain binds to a tumor antigen is selected from a group consisting of: TSHR, CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, PRSS21, VEGFR2, LewisY, CD24, PDGFR-beta, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, and IGLL1. In embodiments, the intracellular signaling domain comprises a co-stimulatory signaling domain, or a primary signaling domain and a co-stimulatory signaling domain, wherein the co-stimulatory signaling domain comprises a functional signaling domain of a protein selected from the group consisting of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D. Sequences may be found at US Patent Publication No: US20190216851, which is incorporated by reference.

In embodiments, the antigen binding molecule is a modified TCR.

In embodiments, the TCR is derived from spontaneously occurring tumor-specific T cells in patients. In embodiments, the TCR binds to a tumor antigen. In embodiments, the tumor antigen comprises CEA, gp100, MART-1, p53, MAGE-A3, or NY-ESO-1. In embodiments, the TCR comprises TCRγ and TCRδ Chains or TCRα and TCRβ chains, or a combination thereof.

In embodiments, the cell is an immune effector cell (e.g., a population of immune effector cells).

For example, the immune effector cell is a T cell or an NK cell. In embodiments, the immune effector cell is a T cell. For example, the T cell is a CD4+ T cell, a CD8+ T cell, or a combination thereof. In embodiments, the cell is a human cell.

In embodiments, the modified cell comprises an inhibitor of expression or function of one or more genes. In embodiments, the inhibitor is (1) a gene editing system targeted to one or more sites within the gene encoding the one or more genes or a corresponding regulatory elements; (2) nucleic acid encoding one or more components of a gene editing system of the one or more genes; or (3) combinations thereof.

In embodiments, the enhanced expression and/or function of the one or more genes is implemented by introducing a nucleic acid sequence of the one or more genes, which is present in the modified cell in a recombinant DNA construct, in an mRNA, or in a viral vector. In embodiments, the reduced of expression and/or function of the one or more genes is implemented by introducing and overexpressing a nucleic acid sequence encoding GRβ, a dominant negative form of TNFR1, a dominant negative form of TNFR1, and/or a dominant negative form of Fas, and nucleic acid sequence is present in the modified cell in a recombinant DNA construct, in an mRNA, or in a viral vector.

In embodiments, the nucleic acid sequence is an mRNA, which is not integrated into the genome of the modified cell. Embodiments relate to an isolated nucleic acid sequence encoding GRβ. In the modified cell, GRβ is overexpressed such that the modified cells may escape or reduce possibilities of glucocorticoid-induced cell death.

In embodiments, the nucleic acid sequence is associated with an oxygen-sensitive polypeptide domain. In embodiments, the oxygen-sensitive polypeptide domain comprises HIF VHL binding domain. In embodiments, the nucleic acid sequence is regulated by a promoter comprising a binding site for a transcription modulator that modulates the expression and/or secretion of the therapeutic agent in the cell. In embodiments, the transcription modulator is or includes Hif1a, NFAT, FOXP3, and/or NFkB.

Modified T-cells may be derived from a stem cell. The stem cells may be adult stem cells, embryonic stem cells, more particularly non-human stem cells, cord blood stem cells, progenitor cells, bone marrow stem cells, induced pluripotent stem cells, totipotent stem cells, or hematopoietic stem cells. A modified cell may also be a dendritic cell, an NK-cell, a B-cell, or a T-cell selected from the group consisting of inflammatory T-lymphocytes, cytotoxic T-lymphocytes, regulatory T-lymphocytes, or helper T-lymphocytes. In another embodiment, Modified cells may be derived from the group consisting of CD4+ T-lymphocytes and CD8+ T-lymphocytes. Prior to expansion and genetic modification of the cells of the invention, a source of cells may be obtained from a subject through a variety of non-limiting methods. T cells may be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available and known to those skilled in the art may be used. In embodiments, modified cells may be derived from a healthy donor, from a patient diagnosed with cancer, or from a patient diagnosed with an infection. In embodiments, the modified cell is part of a mixed population of cells that present different phenotypic characteristics.

The term "stem cell" refers to any of certain types of cell which have the capacity for self-renewal and the ability to differentiate into other kind(s) of a cell. For example, a stem cell gives rise either to two daughter stem cells (as occurs in vitro with embryonic stem cells in culture) or to one stem cell and a cell that undergoes differentiation (as occurs, e.g., in hematopoietic stem cells, which give rise to blood cells). Different categories of stem cells may be distinguished on the basis of their origin and/or on the extent of their capacity for differentiation into other types of cells. For example, the stem cell may include embryonic stem (ES) cells (i.e., pluripotent stem cells), somatic stem cells, Induced pluripotent stem cells, and any other types of stem cells.

The pluripotent embryonic stem cells may be found in the inner cell mass of a blastocyst and have a high innate capacity for differentiation. For example, pluripotent embryonic stem cells may have the potential to form any type of cell in the body. When grown in vitro for long periods of time, ES cells maintain pluripotency: progeny cells retain the potential for multilineage differentiation.

Somatic stem cells may include the fetal stem cells (from the fetus) and adult stem cells (found in various tissues, such as bone marrow). These cells have been regarded as having a capacity for differentiation lower than that of the pluripotent ES cells—with the capacity of fetal stem cells being greater than that of adult stem cells; they apparently differentiate into only a limited range of types of cell and have been described as multipotent. The 'tissue-specific' stem cells normally give rise to only one type of cell. For example, embryonic stem cells may be differentiated into blood stem cells (e.g., Hematopoietic stem cells (HSCs)), which may be further differentiated into various blood cells (e.g., red blood cells, platelets, white blood cells, etc.).

Induced pluripotent stem cells (i.e., iPS cells or iPSCs) may include a type of pluripotent stem cell artificially derived from a non-pluripotent cell (e.g., an adult somatic cell) by inducing expression of specific genes. Induced pluripotent stem cells are similar to natural pluripotent stem cells, such as embryonic stem (ES) cells, in many aspects, such as the expression of certain stem cell genes and proteins, chromatin methylation patterns, doubling time, embryoid body formation, teratoma formation, viable chimera formation, and potency and differentiability. Induced pluripotent cells may be made from the adult stomach, liver, skin cells, and blood cells.

In embodiments, the modified cell is a T cell, NK cell, dendritic cell, or a macrophage.

In embodiments, the antigen binding molecule is the CAR comprising an extracellular domain, a transmembrane domain, and an intracellular domain, the extracellular domain binds an antigen.

In embodiments, the intracellular domain comprises a co-stimulatory signaling region that comprises an intracellular domain of a co-stimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and any combination thereof. In embodiments, the antigen is Epidermal growth factor receptor (EGFR), Variant III of the epidermal growth factor receptor (EGFRvIII), Human epidermal growth factor receptor 2 (HER2), Mesothelin (MSLN), Prostate-specific membrane antigen (PSMA), Carcinoembryonic antigen (CEA), Disialoganglioside 2 (GD2), Interleukin-13Ra2 (IL13Ra2), Glypican-3 (GPC3), Carbonic anhydrase IX (CAIX), L1 cell adhesion molecule (L1-CAM), Cancer antigen 125 (CA125), Cluster of differentiation 133 (CD133), Fibroblast activation protein (FAP), Cancer/testis antigen 1B (CTAG1B), Mucin 1 (MUC1), Folate receptor-α (FR-α), CD19, FZD10, TSHR, PRLR, Muc 17, GUCY2C, CD207, CD3, CD5, B-Cell Maturation Antigen (BCMA), or CD4.

In embodiments, the antigen binding molecule is a modified TCR. In embodiments, the TCR is derived from spontaneously occurring tumor-specific T cells in patients. In embodiments, the TCR binds to a tumor antigen. In embodiments, the tumor antigen comprises CEA, gp100, MART-1, p53, MAGE-A3, or NY-ESO-1. In embodiments, the TCR comprises TCRγ and TCRδ Chains or TCRα and TCRβ chains, or a combination thereof. In embodiments, the TCR comprises TCRγ and TCRδ Chains or TCRα and TCRβ chains. In embodiments, a T cell clone that expresses a TCR with a high affinity for the target antigen may be isolated. In certain embodiments, tumor-infiltrating lymphocytes (TILs) or peripheral blood mononuclear cells (PBMCs) may be cultured in the presence of antigen-presenting cells (APCs) pulsed with a peptide representing an epitope known to elicit a dominant T cell response when presented in the context of a defined HLA allele. High-affinity clones may be then selected on the basis of MHC-peptide tetramer staining and/or the ability to recognize and lyse target cells pulsed with low titrated concentrations of cognate peptide antigen. After the clone has been selected, the TCRα and TCRβ chains or TCRγ and TCRδ Chains are identified and isolated by molecular cloning. For example, for TCRα and TCRβ chains, the TCRα and TCRβ gene sequences are then used to generate an expression construct that ideally promotes stable, high-level expression of both TCR chains in human T cells. The transduction vehicle (e.g., a gammaretrovirus or lentivirus) may then be generated and tested for functionality (antigen specificity and functional avidity) and used to produce a clinical lot of the vector. An aliquot of the final product is then used to transduce the target T cell population (generally purified from patient PBMCs), which is expanded before infusion into the patient. Various methods may be implemented to obtain genes encoding tumor-reactive TCR. More information is provided in Kershaw et al., Clin Transl Immunology. 2014 May; 3(5): e16.

In embodiments, specific TCR can be derived from spontaneously occurring tumor-specific T cells in patients. Antigens included in this category include the melanocyte differentiation antigens MART-1 and gp100, as well as the MAGE antigens and NY-ESO-1, with expression in a broader range of cancers. TCRs specific for viral-associated malignancies can also be isolated, as long as viral proteins are expressed by transformed cells. Malignancies in this category include liver and cervical cancer, associated with hepatitis and papilloma viruses, and Epstein-Barr virus-associated malignancies. In embodiments, target antigens of the TCR may include CEA (e.g., for colorectal cancer), gp100, MART-1, p53 (e.g., for Melanoma), MAGE-A3 (e.g., Melanoma, esophageal and synovial sarcoma), NY-ESO-1 (e.g., for Melanoma and sarcoma as well as Multiple myelomas).

Embodiments relate to a modified cell comprising one or more polynucleotides encoding one or more proteins assembling an extracellular vesicle (EV) and encoding or comprising a therapeutic agent. In embodiments, the modified cell is engineered to express an antigen binding molecule.

The term "extracellular vesicle," as used herein, refers to a cell-derived vesicle that is generated by a combination of endocytotic and exocytotic events that result in the encapsulation of various proteins and nucleic acids. Such encapsulation may protect a therapeutic nucleic acid from enzymatic degradation or other environmental stresses (e.g., ionic strength, pH, etc.). The association of proteins with an extracellular vesicle provides stability in both extracellular and intracellular environments as well as facilitates a cell-targeting mechanism for cell-cell communication.

In embodiments, Extracellular Vesicles: a vesicular structure secreted by a cell that specifically encapsulates an RNA sequence. Extracellular vesicles (EVs) are vesicle-like bodies of a two-layer membrane structure that are detached from the cell membrane or secreted by the cells, ranging in diameter from 40 nm to 1000 nm. Extracellular vesicles are mainly composed of microvesicles (MVs) and exosomes (Exs). Microvesicles are small vesicles that are detached from the cell membrane after cell activation, injury, or apoptosis, and have a diameter of about 100 nm to 1000 nm. The exosomes are released to the outside of the cell by extracellular secretion after fusion of the multivesicular bodies in the cells with the cell membrane and have a diameter of about 40 nm to 100 nm. More information about EV and the manufacture of EV may be found at Pastuzyn et al., Cell. 2018 Jan. 11; 172(1-2): 275-288.e18, which is incorporated herein as reference.

In embodiments, expression of the one or more polynucleotides may be regulated by an inducible expression system. The inducible expression system allows for a temporal and spatial controlled activation and/or expression of genes. For example, Tetracycline-Controlled Transcriptional Activation is a method of inducible gene expression where transcription is reversibly turned on or off in the presence of the antibiotic tetracycline or one of its derivatives (e.g., doxycycline). For example, an inducible suicide gene expression system allows for a temporal and spatial controlled activation and/or expression of a suicide gene, which causes a cell to kill itself through apoptosis.

In embodiments, the modified cells comprise a nucleic acid sequence encoding a reverse tetracycline transactivator (rtTA). In embodiments, expression of the one or more molecules is regulated by the rtTA, such that the one or more polynucleotides are expressed in the presence of tetracycline. In embodiments, a concentration of tetracycline in the cell culture medium is not less than about 2 µg/ml. In embodiments, the tetracycline is selected from the group consisting of tetracycline, demeclocycline, meclocycline, doxycycline, lymecycline, methacycline, minocycline, oxytetracycline, rolitetracycline, and chlortetracycline. In embodiments, the tetracycline is doxycycline.

In embodiments, the inducible suicide system is an HSV-TK system or an inducible caspase-9 system. In embodiments, the modified cells comprise a nucleic acid sequence encoding a suicide gene, such that when the modified cells are in the presence of a nucleoside analogue in a manner permitting expression of the suicide gene, to render the nucleoside analogue cytotoxic to the modified cells. In embodiments, the suicide gene is selected from the group consisting of thymidine kinase of herpes simplex virus, thymidine kinase of varicella zoster virus, and bacterial cytosine deaminase. In embodiments, the suicide gene is thymidine kinase of herpes simplex virus. In embodiments, the nucleoside analogue is selected from the group consisting of ganciclovir, acyclovir, buciclovir, famciclovir, penciclovir, valciclovir, trifluorothymidine, 1-[2-deoxy, 2-fluoro, beta-D-arabino furanosyl]-5-iodouracil, ara-A, araT 1-beta-D-arabinofuranoxyl thymine, 5-ethyl-2'-deoxyuridine, 5-iodo-5'-amino-2,5'-dideoxyuridine, idoxuridine, AZT, AIU, dideoxycytidine, and AraC. In embodiments, the nucleoside analogue is ganciclovir.

In embodiments, achieving intracellular recognition and killing is achieved by enhancing the expression of MHC I, that is, by encapsulating a gene that promotes MHC I expression. Identification of P53 mutation recognition, chromosome structure abnormality (e.g., TFEB reference). The designated RNA means that the extracellular vesicle secreted by the gene we want to wrap (e.g., TFEB, etc.) does not have a significant effect on normal cells, but according to the package, The gene may have different effects on the tumor, such as inhibiting the tumor or normalizing the tumor cells. Of course, this can be used not only in combination with NFAT but also in drug induction (tox system), pathway induction (Notch system).

In embodiments, the antigen binding molecule is chimeric antigen receptor (CAR), which comprises an antigen-binding domain, a transmembrane domain, and an intracellular signaling domain. In embodiments, the antigen-binding domain binds to a tumor antigen is selected from a group consisting of: TSHR, CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, PRSS21, VEGFR2, LewisY, CD24, PDGFR-beta, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, and IGLL1. In embodiments, the intracellular signaling domain comprises a co-stimulatory signaling domain, or a primary signaling domain and a co-stimulatory signaling domain, wherein the co-stimulatory signaling domain comprises a functional signaling domain of a protein selected from the group consisting of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D.

In embodiments, the polynucleotide may integrate into the genome of the modified cell, and descendants of the modified cell will also express the polynucleotide, resulting in a stably transfected modified cell. In embodiments, the modified cell may express the polynucleotide encoding the CAR, but the polynucleotide does not integrate into the genome of the modified cell such that the modified cell expresses the transiently transfected polynucleotide for a finite period of time (e.g., several days), after which the polynucleotide is lost through cell division or other factors. For example, the polynucleotide is present in the modified cell in a recombinant DNA construct, in an mRNA, or in a viral vector, and/or the polynucleotide is an mRNA, which is not integrated into the genome of the modified cell.

Embodiments relate to a method or use of polynucleotide. The method of use includes: providing a viral particle (e.g., AAV, lentivirus or their variants) comprising a vector genome, the vector genome comprising the polynucleotide, wherein the polynucleotide is operably linked to an expression control element conferring transcription of the polynucleotide and administering an amount of the viral particle to the subject such that the polynucleotide is expressed in the subject. In embodiments, the AAV preparation may include AAV vector particles, empty capsids, and host cell impurities, thereby providing an AAV product substantially free of AAV empty capsids. More information of the administration and preparation of the viral particle may be found at the U.S. Pat. No. 9,840,719 and Milani et al., Sci. Transl. Med. 11, eaav7325 (2019) 22 May 2019, which are incorporated herein by reference.

In embodiments, the antigen binding molecule is a modified TCR. In embodiments, the TCR is derived from spontaneously occurring tumor-specific T cells in patients. In embodiments, the TCR binds to a tumor antigen. In embodiments, the tumor antigen comprises CEA, gp100, MART-1, p53, MAGE-A3, or NY-ESO-1. In embodiments, the TCR comprises TCRγ and TCRδ Chains or TCRα and TCRβ chains, or a combination thereof.

In embodiments, the cell is an immune effector cell (e.g., a population of immune effector cells). In embodiments, the immune effector cell is a T cell or an NK cell. In embodiments, the immune effector cell is a T cell. In embodiments, the T cell is a CD4+ T cell, a CD8+ T cell, or a combination thereof. In embodiments, the cell is a human cell.

In embodiments, the modified cell comprises an inhibitor of expression or function of the one or more genes. In embodiments, the inhibitor is (1) a gene editing system targeted to one or more sites within the gene encoding the one or more genes or a corresponding regulatory elements; (2) nucleic acid encoding one or more components of a gene editing system of the one or more genes; or (3) combinations thereof.

Embodiments relate to a pharmaceutical composition comprising the population of the cells described above. Embodiments relate to a method of causing or eliciting T cell response in a subject in need thereof and/or treating a tumor of the subject, the method comprising administering an effective amount of the composition. Embodiments relate to a method of delivering the therapeutic agent, the method comprising administering an effective amount of the composition.

In embodiments, the one or more polynucleotides are present in the modified cell in a recombinant DNA construct, in an mRNA, or in a viral vector. In embodiments, the nucleic acid sequence is an mRNA, which is not integrated into the genome of the modified cell. In embodiments, the one or more polynucleotides are associated with an oxygen-sensitive polypeptide domain. In embodiments, the oxygen-sensitive polypeptide domain comprises HIF VHL binding domain. In embodiments, expression of the one or more polynucleotide is regulated by a promoter comprising a binding site for a transcription modulator that modulates the expression and/or secretion of the therapeutic agent in the cell. In embodiments, the transcription modulator is or includes Hif1a, NFAT, FOXP3, and/or NFkB.

In embodiments, expression the one or more polynucleotide is regulated by NFAT such that the EV is assembled in response to activation of the modified cell.

Embodiments relate to a polynucleotide comprising a binding site of a transcription modulator (e.g., NFAT) and encoding one or more proteins assembling the extracellular vesicle (EV) and the therapeutic agent.

In embodiments, the one or more proteins are self-assembling proteins. In embodiments, the one or more proteins that direct their release through vesicles as a luminal membrane-bound protein is chosen from the group consisting of: the retroviral group specific antigen, retroviral group specific antigen variations, the influenza MI protein, the ARRDCI protein, the ARC protein, the Ebola virus VP40 protein and the M proteins of vesicular stomatitis virus. In embodiments, the one or more proteins comprise an Arc protein, and the one or more polynucleotides comprise a nucleic acid encoding a therapeutic agent. More information on ARC based EV may be found in PCT Patent Publication Nos: WO2019091964 and WO2019118497 as well as Pastuzyn et al., Cell. 2018 Jan. 11; 172(1-2): 275-288.e18, which are herein incorporated by reference.

Embodiments relate to an EV comprising an Arc protein and a nucleic acid encoding or comprising a therapeutic agent, the nucleic acid is DNA or RNA encoding the therapeutic agent.

In embodiments, the therapeutic agent is selected from the group consisting of a siRNA, an shRNA, and RNAi. In embodiments, the nucleic acid encoding a therapeutic agent is linked to a 3' UTR sequence. In embodiments, the 3' UTR sequence is bound to the Arc protein. In embodiments, the 3' UTR sequence is an arc mRNA 3' UTR sequence. In embodiments, the nucleic acid further comprises a transcription modulator sequence.

The term "Arc protein," as used herein, refers to an activity-regulated cytoskeleton protein associated with neuronal plasticity that can be encapsulated into an extracellular vesicle. The term "3' UTR sequence," as used herein, refers to a mRNA-derived 3' untranslated repeat sequence that is capable of binding to a protein within an extracellular vesicle. For example, an arc 3 'UTR sequence may bind to an Arc protein within an extracellular vesicle. Such 3' UTR binding to a protein may occur with only the 3' UTR sequence, or when the 3' UTR sequence is linked to a non-arc nucleic acid.

The term "endocytosis," "endocytose," "endocytosing," or "endocytosed," as used herein, refers to the incorporation of substances into a cell by phagocytosis or pinocytosis.

In embodiments, the therapeutic agent is scFv binding a tumor antigen on the membrane or inside of a tumor cell. In embodiments, the tumor antigen is described above.

Embodiments relate to a cell modified to express one or more molecules at a level that is higher than the level of the one or more expressed by a cell that has not been modified to expression the one or more molecules, where the one or more molecules are overexpressed in cancer cells, associated with recruitment of immune cells, and/or associated with autoimmunity.

Embodiments relate to a modified cell engineered to express an antigen binding molecule, wherein expression and/or function of one or more molecules in the modified cell has been enhanced, or reduced or eliminated, where the one or more molecules are overexpressed in cancer cells, associated with recruitment of immune cells, and/or associated with autoimmunity. In embodiments, the modified cell comprises a disruption in an endogenous gene or addition of an exogenous gene that is associated with a biosynthesis or transportation pathway of the one or more molecules. Embodiments relate to a method or use of polynucleotide, the method comprising providing a viral particle (e.g., AAV, lentivirus or their variants) comprising a vector genome, the vector genome comprising the polynucleotide encoding the one more molecules, and a polynucleotide encoding a binding molecule, the polynucleotide operably linked to an expression control element conferring transcription of the polynucleotides; and administering an amount of the viral particle to a subject such that the polynucleotide is expressed in the subject, where the one or more molecules are overexpressed in cancer cells, associated with recruitment of immune cells, and/or associated with autoimmunity. In embodiments, the AAV preparation may include AAV vector particles, empty capsids, and host cell impurities, thereby providing an AAV product substantially free of AAV empty capsids.

Embodiments relate to a pharmaceutical composition comprising the population of the cells. Embodiments relate to a method of causing or eliciting T cell response in a subject in need thereof and/or treating a tumor of the subject, the method comprising administering an effective amount of the composition to the subject. Embodiments relate to an isolated nucleic acid sequence encoding one or more molecules are overexpressed in cancer cells, associated with recruitment of immune cells, and/or associated with autoimmunity.

Embodiments relate to modified cells including overexpress or inducing expression of NRIP3, TNS1, ALXO5, IGF2, SERPINA1, MET, SGK1, ZNF286B, GLI2 genes, and corresponding mutants to enhance proliferation of cells (including DCs, granulocytes, monocytes, NK and other immune cells) and ability to infiltrate the tumor environment and to resist apoptosis, thereby increasing the killing ability of cells in the tumor microenvironment. The tumor microenvironment inhibits the infiltration and killing ability of immune cells. Embodiments relate to enhancement of the multiple functions of immune cells by overexpressing or inducing expression of NRIP3, TNS1, ALXO5, IGF2, SERPINA1, MET, SGK1, ZNF286B, GLI2 genes, or mutants. These genes appear to better regulate the function of immune cells to enhance the ability to kill tumors. In embodiments, suicide genes may be added to the modified cells, such as to degrade or eliminate cells expressing these genes, allowing these genes to work safely and effectively.

In embodiments, the one more molecules comprise NRIP3, TNS1, ALXO5, IGF2, SERPINA1, MET, SGK1, ZNF286B, GLI2, a functional variant of the one or more molecules, or a functional fragment of the one or more molecules.

Embodiments relate to composition and methods to combine innate immune cells such as DC cells, granulocytes, and the like with CAR-T cells to enhance the function of T cells. For example, IFNγ produced by T cells can induce the production of IL-12 by DC cells, and IL-12 can serve as an essential activation signal to enhance T cells attacking tumors. The synergistic effect of immune cells in the tumor microenvironment makes CAR-T treatment more effective. It is also possible to recruit immune cells with various factors to enhance T cell function. Among them, HMGB1 is an important protein involved in the connection between natural immunity and adaptive immunity. When HMGB1 is in acute stress (granulocyte, NK cell) apoptosis, HMGB1 will be released extracellularly, and it has pro-inflammatory, activation, and recruitment. The function of monocyte. In addition, CXCL9 can recruit DC/monocytes, CCL20 recruits granulocytes, IL5, IL13 recruits eosinophils, P2Y12 recruits monocytes, CCL2 (MCP-1) recruits macrophages/monocytes, CCL7 recruits macrophages IL35 recruits monocytes, CX3CL1 recruits monocytes, IL8 recruits T cells, and granulocytes, and M-CSF recruits mononuclear and macrophages. In embodiments, combined with molecules such as CCL19 and FLT3L, DC/mononuclear/CCR7+ cells are synergistic with T cells. Molecules such as CCL19/FLT3L/HMGB are expressed in CAR-T cells, which can recruit DC cells, etc., and then activate the DC cells with an agonist to amplify the T cells. In embodiments, the one more molecules comprise at least one of CCL19, FLT3L, HMGB, a functional variant of the one or more molecules, or a functional fragment of the one or more molecules.

Embodiments relate to compositions and methods to use molecules associated with autoimmunity to solve the problem of cell depletion in cell-facing solid tumors and insufficient expansion of cells in the microenvironment of solid tumors. Autoimmunity is mainly manifested as non-specific activation of lymphocytes, auxiliary stimulating factors Activate T/B cells, immune regulation network (Th1, Th2, Th17) disorders. Therefore, the use of genes highly expressed in autoimmune diseases in T cells to promote higher T cell activity is an effective strategy for cell therapy. AIRE (Autoimmune regulator) regulates immune tolerance and inhibits autoimmune response, and its inhibition of the immune system can be relieved by knock down/knock out AIRE. RIPK1 activates TLR3 and TLR4 downstream signaling pathways, activates MAPK and NFκB signaling pathways, increases NLRP3 activity, and releases a large number of inflammatory factors; RIPK2 activates downstream NFκB signaling pathway, and simultaneously activates TCR and BCL10, promotes T cell proliferation, and activates participation in immunity. Reactive gene; RIPK3 activates LPS-mediated immune response pathway; activates NFκB signaling pathway and NLRP3 inflammatory bodies; FcRL3, FcRL6 is an autoimmune susceptibility gene that activates B cell NFκB and MAPK pathways, and causes abnormal immune activation; TICAM1 can activate TLR3, TLR5 downstream signaling pathway, stimulates NFκB and type I interferon release; TICAM2 activates TLR2 downstream signaling pathway to produce IL18; activates TLR4 downstream signaling pathway to produce type I interferon; IFIH1 acts as an innate immune receptor, activates antiviral The immune system stimulates the production of type I interferon and a large number of pro-inflammatory factors; IRF4, RORA, RORC participate in the Th17 differentiation signaling pathway, induce T cell differentiation to Th17, and release IL17; ACT1, TRAF6, TAB2, TAB3, TAK1, IL17RA, IL17RC The IL17 signaling pathway may induce the autoimmune disease through overexpression. In embodiments, the one more molecules comprise at least one of RIPK1, RIPK2, RIPK3, FcRL3, FcRL6, TICAM1, TICAM2, IFIH1, IRF4, RORA, RORC, ACT1, TRAF6, TAB2, TAB3, TAK1, IL17 RA, IL17RC, a functional variant of the one or more molecules, or a functional fragment of the one or more molecules. In embodiments, the one more molecules comprise AIRE, a functional variant of the one or more molecules, or a functional fragment of the one or more molecules, and the function and/or expression of AIRE in the modified cell is reduced or eliminated.

In embodiments, the expression of one or more molecules may be regulated by an inducible expression system. The inducible expression system allows for a temporal and spatial controlled activation and/or expression of genes. For example, Tetracycline-Controlled Transcriptional Activation is a method of inducible gene expression where transcription is reversibly turned on or off in the presence of the antibiotic tetracycline or one of its derivatives (e.g., doxycycline). For example, an inducible suicide gene expression system allows for a temporal and spatial controlled activation and/or expression of a suicide gene, which causes a cell to kill itself through apoptosis.

In embodiments, the polynucleotide may integrate into the genome of the modified cell, and descendants of the modified cell will also express the polynucleotide, resulting in a stably transfected modified cell. In embodiments, the modified cell may express the polynucleotide encoding the CAR, but the polynucleotide does not integrate into the genome of the modified cell such that the modified cell expresses the transiently transfected polynucleotide for a finite period of time (e.g., several days), after which the polynucleotide is lost through cell division or other factors. For example, the polynucleotide is present in the modified cell in a recombinant DNA construct, in an mRNA, or in a viral vector, and/or the polynucleotide is an mRNA, which is not integrated into the genome of the modified cell.

Embodiments relate to a modified cell engineered to express an antigen binding molecule, wherein expression and/or function of one or more molecules in the modified cell has been reduced or eliminated, the one or more molecules associated with apoptosis of the modified cell. In embodiments, the one or more molecules may include glucocorticoid receptor α (GRα), Fas, TNFR1, TNFR2, and/or TRAIL. In embodiments, the modified cell comprises a disruption in an endogenous gene or addition of an exogenous gene that is associated with a biosynthesis or transportation pathway of the one or more molecules.

In embodiments, the amplification of T cells is enhanced by inhibiting the apoptosis of T cells. It acts primarily through the FAS, TNFR1/2, and TRAIL signaling pathways. Fas is a transmembrane protein belonging to the tumor necrosis factor receptor superfamily. Its binding to FasL can initiate apoptosis of apoptosis signals. Its activation involves a series of steps: first, the ligand induces receptor trimerization and then forms an apoptosis-inducing complex on the cell membrane, which includes the Fas-associated protein FADD with a death domain. The complex then polymerizes the molecules of multiple caspase8, which in turn causes a subsequent cascade reaction, namely Caspases, which is activated as a zymogen, causing the following cascade. The cells undergo apoptosis. The TNF-mediated apoptotic pathway is similar to FAS, which is mediated by the death receptor TNFRI. Tumor necrosis factor receptor (TNF Rs) is the representative family of the largest death receptors, including TNFRI (p55, CD120a), TNFRII (p75, CD120b), and the like. The common feature is that the intracellular region has a highly homologous amino acid sequence necessary for transducing cell death signals, namely DD. In recent years, the death domain proteins found mainly include FADD, TNFRI associated death domain protein (TRADD), and receptor interacting protein (RIP). TNF is mainly produced by infected and activated macrophages and T cells and mediates apoptosis through its cell surface receptors TNFRI and TNFRII. In embodiments, an apoptotic signal is a tumor necrosis factor related to apoptosis-induced ligand (TRAIL), which is a member of the tumor necrosis factor family and is capable of inducing apoptosis in most human tumor cells. There is no obvious cytotoxicity to normal cells. TRAIL induces tumor cell apoptosis mainly by activating exogenous pathways, accompanied by cascade amplification of endogenous pathways. After TRAIL binds to the death receptor on the cell membrane surface, the intramembranous segment of the death receptor activates and undergoes self-shearing to form death-inducing signaling complexes (DISCs). The recruitment of Fas-associated death domain (FADD) and caspase-8, caspase-10 precursors is a prerequisite for the formation of DISCs. Caspase-8 and caspase-10 precursors form active cleaved caspase-8 and cleaved caspase-10, which in turn activates caspase-3, 6, and 7 and initiates apoptosis. In embodiments, dominant negative forms of FAS/TNFR1/2 and TRAIL or direct knockout/knock down (e.g., TALEN) may be used to inhibit T cell apoptosis. In embodiments, reducing of function or expression of downstream signals such as caspase8/3/fadd-caspase10 and PRKC may be implemented to inhibit apoptosis.

Embodiments relate to a method of expanding modified cells, the method comprising reducing or eliminating function or expression of the one or more molecules in the modified cells such that cell death of the modified cells induced by the one or more molecules are reduced as compared to the modified cells of which function of expression of the one or more molecules is not reduced or eliminated. In embodiments, reduced cell death achieves a similar effect (e.g., cell numbers) of those methods that directly increase cell numbers, which may also be considered as an expansion of the modified cells in the present application.

Embodiments relate to a modified cell engineered to express an antigen binding molecule, wherein expression and/or function of glucocorticoid receptor α (GRα) in the modified cell has been reduced or eliminated. Embodiments relate to a pharmaceutical composition comprising the population of the cells. Embodiments relate to a method of causing or eliciting T cell response in a subject in need thereof and/or treating a tumor of the subject, the method comprising administering an effective amount of the composition. For example, the modified cell comprises a disruption in an endogenous gene or addition of an exogenous gene that is associated with a biosynthesis or transportation pathway of GRα.

In embodiments, the modified cell comprises an inhibitor of expression or function of the one or more genes. In embodiments, the inhibitor is (1) a gene editing system targeted to one or more sites within the gene encoding the one or more genes or a corresponding regulatory elements; (2) nucleic acid encoding one or more components of a gene editing system of the one or more genes; or (3) combinations thereof.

In embodiments, the enhanced expression and/or function of the one or more genes is implemented by introducing a nucleic acid sequence of the one or more genes, which is present in the modified cell in a recombinant DNA construct, in an mRNA, or in a viral vector. In embodiments, the reduced of expression and/or function of the one or more genes is implemented by introducing and overexpressing a nucleic acid sequence encoding GRβ, a dominant negative form of TNFR1, a dominant negative form of TNFR1, and/or a dominant negative form of Fas, and nucleic acid sequence is present in the modified cell in a recombinant DNA construct, in an mRNA, or in a viral vector.

In embodiments, the nucleic acid sequence is an mRNA, which is not integrated into the genome of the modified cell. Embodiments relate to an isolated nucleic acid sequence encoding GRβ. In the modified cell, GRβ is overexpressed such that the modified cells may escape or reduce possibilities of glucocorticoid-induced cell death.

In embodiments, the nucleic acid sequence is associated with an oxygen-sensitive polypeptide domain. In embodiments, the oxygen-sensitive polypeptide domain comprises HIF VHL binding domain. In embodiments, the nucleic acid sequence is regulated by a promoter comprising a binding site for a transcription modulator that modulates the expression and/or secretion of the therapeutic agent in the cell. In embodiments, the transcription modulator is or includes Hif1a, NFAT, FOXP3, and/or NFkB.

Embodiments related to a cell modified to express one or more molecules at a level that is higher than the level of the one or more expressed by a cell that has not been modified to expression the one or more molecules, wherein the one or more molecules are associated with biosynthesis and/or transportation of inflammasome. Embodiments related to a modified cell engineered to express an antigen binding molecule, wherein the expression and/or function of one or more molecules in the modified cell has been enhanced, where the one or more molecules are associated with biosynthesis and/or transportation of inflammasome. In embodiments, the modified cell comprises a disruption in an endogenous gene or addition of an exogenous gene that is associated with a biosynthesis or transportation pathway of the one or more molecules.

Embodiments related to a pharmaceutical composition comprising the population of the cells above. Embodiments related to a method of causing or eliciting T cell response in a subject in need thereof and/or treating a tumor of the subject, the method comprising administering an effective amount of the composition to the subject. Embodiments related to an isolated nucleic acid sequence encoding one or more molecules are associated with biosynthesis and/or transportation of inflammasome.

In embodiments, the expression of one or more molecules is regulated by one or more promoters. In embodiments, the polynucleotide comprises a promoter comprising a binding site for a transcription modulator that modulates the expression and/or secretion of the one or more molecules in the cell. For example, the transcription modulator is or includes Hif1a, NFAT, FOXP3, and/or NFkB. For example, the one or more molecules comprise at least one cytokine associated with an oxygen-sensitive polypeptide domain, and the oxygen-sensitive polypeptide domain comprises HIF VHL binding domain.

In embodiments, the one more molecules comprise at least one of NLRR1, NLRP3, ASC, PYD, NOD2, CARD, RIP2, RICK, TBK1, and TAK1/2, a functional variant of the one or more molecules, or a functional fragment of the one or more molecules.

In embodiments, the one or more molecules comprise at least one of NLRP1, NLRP3, and TBK1, a functional variant of the one or more molecules, or a functional fragment of the one or more molecules.

Embodiments relate to a modified cell comprising a polynucleotide encoding a dominant negative form of Death receptor 5 (DR5). Embodiments relate to a pharmaceutical composition comprising a population of the modified cells. Embodiments relate to a method of causing or eliciting T cell response in a subject in need thereof and/or treating a tumor of the subject, the method comprising administering an effective amount of the composition of to the subject. Embodiments relate to a nucleotide acid sequence comprising the polynucleotide encoding the dominant negative form of DR5. Embodiments relate to a method of enhancing T cell response, the method comprising: a population of modified cells of claim 1, the modified cells comprising a CAR; contacting target cells that the CAR bind with the population of modified cells; and measuring a level of the T cell response, wherein the T cell response is greater than that of a population of modified cells that have the CAR but don't have the polynucleotide and that are contacted with the target cells.

Death receptor 5 (DR5), also known as TRAIL receptor 2 (TRAILR2) and tumor necrosis factor receptor superfamily member 10B (TNFRSF10B), is a cell surface receptor of the TNF-receptor superfamily that binds TRAIL and mediates apoptosis. In embodiments, the modified cell comprises the amino acid sequence of SEQ ID NO: 1 or 2.

In embodiments, the modified cell further comprises a chimeric antigen receptor (CAR). In embodiments, the CAR comprises which comprises an antigen-binding domain, a transmembrane domain, and an intracellular signaling domain. In embodiments, the antigen-binding domain binds to a tumor antigen is selected from a group consisting of: TSHR, CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, PRSS21, VEGFR2, Lewis Y, CD24, PDGFR-beta, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, GM3, TGS5, HMWMAA, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, MAGE A1, ETV6-AML, sperm protein 17, XAGE1, Tie 2, MAD-CT-1, MAD-CT-2, Fos-related antigen 1, p53, p53 mutant, prostein, surviving, telomerase, PCTA-1 (Galectin 8), MelanA (MART1), Ras mutant, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase (hTERT), RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, MAGE A4, CLDN 18.2, GCC (GUCY2C), or IGLL1. In embodiments, the intracellular signaling domain comprises a co-stimulatory signaling domain, or a primary signaling domain and a co-stimulatory signaling domain, wherein the co-stimulatory signaling domain comprises a functional signaling domain of a protein selected from the group consisting of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D.

In embodiments, the modified cell further comprises a modified TCR. In embodiments, the TCR is derived from spontaneously occurring tumor-specific T cells in patients. In embodiments, the TCR binds to a tumor antigen. In embodiments, the tumor antigen comprises CEA, gp100, MART-1, p53, MAGE-A3, or NY-ESO-1. In embodiments, the TCR comprises TCRγ and TCRδ Chains or TCRα and TCRβ chains, or a combination thereof.

In embodiments, the modified cell is an immune effector cell. In embodiments, the immune effector cell is a T cell or an NK cell. In embodiments, the immune effector cell is a T cell. In embodiments, the T cell is a CD4+ T cell, a CD8+ T cell, or a combination thereof. In embodiments, the cell is a human cell.

The present disclosure is further described by reference to the following exemplary embodiments and examples. These exemplary embodiments and examples are provided for purposes of illustration only and are not intended to be limiting unless otherwise specified. Thus, the present disclosure should in no way be construed as being limited to the following exemplary embodiments and examples, but rather, should be construed to encompass any and all variations which become evident as a result of the teaching provided herein.

EXEMPLARY EMBODIMENTS

The following are exemplary embodiments:
1. A modified cell engineered to express an antigen binding molecule, wherein expression and/or function of glucocorticoid receptor α (GRα) in the modified cell has been reduced or eliminated.
2. The modified cell of embodiment 1, wherein the modified cell comprises a disruption in an endogenous gene or addition of an exogenous gene that is associated with a biosynthesis or transportation pathway of GRα.
3. The modified cell of one of embodiments 1 and 2, wherein the antigen binding molecule is chimeric antigen receptor (CAR), which comprises an antigen-binding domain, a transmembrane domain, and an intracellular signaling domain.
4. The modified cell of embodiment 3, wherein the antigen-binding domain binds to a tumor antigen is selected from a group consisting of: TSHR, CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, PRSS21, VEGFR2, LewisY, CD24, PDGFR-beta, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, and IGLL1.
5. The modified cell of one of embodiments 3 and 4, wherein the intracellular signaling domain comprises a co-stimulatory signaling domain, or a primary signaling domain and a co-stimulatory signaling domain, wherein the co-stimulatory signaling domain comprises a functional signaling domain of a protein selected from the group consisting of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D.
6. The modified cell of one of embodiments 1-5, wherein the antigen binding molecule is a modified TCR.
7. The modified cell of embodiment 6, wherein the TCR is derived from spontaneously occurring tumor-specific T cells in patients.
8. The modified cell of embodiment 7 wherein the TCR binds to a tumor antigen.
9. The modified cell of embodiment 8, wherein the tumor antigen comprises CEA, gp100, MART-1, p53, MAGE-A3, or NY-ESO-1.
10. The modified cell of embodiment 8, wherein the TCR comprises TCRγ and TCRδ Chains or TCRα and TCRβ chains, or a combination thereof.
11. The modified cell of any of the preceding embodiments, wherein the cell is an immune effector cell (e.g., a population of immune effector cells).
12. The modified cell of embodiment 11, wherein the immune effector cell is a T cell or an NK cell.
13. The modified cell of embodiment 12, wherein the immune effector cell is a T cell.
14. modified cell of embodiment 13, wherein the T cell is a CD4+ T cell, a CD8+ T cell, or a combination thereof.
15. The modified cell of any of the preceding embodiments, wherein the cell is a human cell.
16. The modified cell of any of the preceding embodiments, wherein the modified cell comprises an inhibitor of expression or function of the one or more genes.
17. The modified cell of embodiment 16, wherein the inhibitor is (1) a gene editing system targeted to one or more sites within the gene encoding the one or more genes or a corresponding regulatory elements; (2) nucleic acid encoding one or more components of a gene editing system of the one or more genes; or (3) combinations thereof.

18. A pharmaceutical composition comprising the population of the cells of any of embodiments 1-17.

19. A method of causing or eliciting T cell response in a subject in need thereof and/or treating a tumor in the subject, the method comprising administering an effective amount of the composition of embodiment 18 to the subject.

20. The modified cell, the method, the pharmaceutical composition, the cell of one of embodiments 1-19, wherein the enhanced expression and/or function of the one or more genes is implemented by introducing a nucleic acid sequence of the one or more genes, which is present in the modified cell in a recombinant DNA construct, in an mRNA, or in a viral vector.

21. The modified cell, the method, the pharmaceutical composition, the cell of one of embodiments 1-21, wherein the reduced of expression and/or function of the one or more genes is implemented by introducing and overexpressing a nucleic acid sequence encoding GRβ, and nucleic acid sequence is present in the modified cell in a recombinant DNA construct, in an mRNA, or in a viral vector.

22. The modified cell, the method, the pharmaceutical composition, the cell of one of embodiments 21 and 22, wherein the nucleic acid sequence is an mRNA, which is not integrated into the genome of the modified cell.

23. The modified cell, the method, the pharmaceutical composition, the cell of one of embodiments 20-22, wherein the nucleic acid sequence is associated with an oxygen-sensitive polypeptide domain.

23. The modified cell, the method, the pharmaceutical composition, the cell of embodiment 23, wherein the oxygen-sensitive polypeptide domain comprises HIF VHL binding domain.

24. The modified cell, the method, the pharmaceutical composition, the cell of one of embodiments 20-23, wherein the nucleic acid sequence is regulated by a promoter comprising a binding site for a transcription modulator that modulates the expression and/or secretion of the therapeutic agent in the cell.

25. The modified cell, the method, the pharmaceutical composition, the cell of embodiment 24, wherein the transcription modulator is or includes Hif1a, NFAT, FOXP3, and/or NFkB.

26. A modified cell engineered to express an antigen binding molecule, wherein expression and/or function of one or more molecules in the modified cell has been reduced or eliminated, the one or more molecules associated with apoptosis of the modified cell, the one or more molecules comprising: glucocorticoid receptor α (GRα), Fas, TNFR1, TNFR2, and/or TRAIL.

27. The modified cell of embodiment 26, wherein the modified cell comprises a disruption in an endogenous gene or addition of an exogenous gene that is associated with a biosynthesis or transportation pathway of the one or more molecules.

28. The modified cell of one of embodiments 26 and 27, wherein the antigen binding molecule is chimeric antigen receptor (CAR), which comprises an antigen-binding domain, a transmembrane domain, and an intracellular signaling domain.

29. The modified cell of embodiment 28, wherein the antigen-binding domain binds to a tumor antigen is selected from a group consisting of: TSHR, CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, PRSS21, VEGFR2, LewisY, CD24, PDGFR-beta, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, and IGLL1.

30. The modified cell of one of embodiments 28 and 29, wherein the intracellular signaling domain comprises a co-stimulatory signaling domain, or a primary signaling domain and a co-stimulatory signaling domain, wherein the co-stimulatory signaling domain comprises a functional signaling domain of a protein selected from the group consisting of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D.

31. The modified cell of one of embodiments 26-30, wherein the antigen binding molecule is a modified TCR.

32. The modified cell of embodiment 31, wherein the TCR is derived from spontaneously occurring tumor-specific T cells in patients.

33. The modified cell of embodiment 32 wherein the TCR binds to a tumor antigen.

34. The modified cell of embodiment 33, wherein the tumor antigen comprises CEA, gp100, MART-1, p53, MAGE-A3, or NY-ESO-1.

35. The modified cell of embodiment 33, wherein the TCR comprises TCRγ and TCRδ Chains or TCRα and TCRβ chains, or a combination thereof.

11. The modified cell of any of the preceding embodiments, wherein the cell is an immune effector cell (e.g., a population of immune effector cells).
36. The modified cell of embodiment 11, wherein the immune effector cell is a T cell or an NK cell.
37. The modified cell of embodiment 36, wherein the immune effector cell is a T cell.
38. modified cell of embodiment 37, wherein the T cell is a CD4+ T cell, a CD8+ T cell, or a combination thereof.
39. The modified cell of any of the preceding embodiments, wherein the cell is a human cell.
40. The modified cell of any of the preceding embodiments, wherein the modified cell comprises an inhibitor of expression or function of the one or more genes.
41. The modified cell of embodiment 40, wherein the inhibitor is (1) a gene editing system targeted to one or more sites within the gene encoding the one or more genes or a corresponding regulatory elements; (2) nucleic acid encoding one or more components of a gene editing system of the one or more genes; or (3) combinations thereof.
42. A pharmaceutical composition comprising the population of the cells of any of embodiments 26-17.
43. A method of causing or eliciting T cell response in a subject in need thereof and/or treating a tumor of the subject, the method comprising administering an effective amount of the composition of embodiment 42 to the subject.
44. The modified cell, the method, the pharmaceutical composition, the cell of one of embodiments 26-19, wherein the enhanced expression and/or function of the one or more genes is implemented by introducing a nucleic acid sequence of the one or more genes, which is present in the modified cell in a recombinant DNA construct, in an mRNA, or in a viral vector.
45. The modified cell, the method, the pharmaceutical composition, the cell of one of embodiments 26-21, wherein the reduced of expression and/or function of the one or more genes is implemented by introducing and overexpressing a nucleic acid sequence encoding GRβ, a dominant negative form of TNFR1, a dominant negative form of TNFR1, and/or a dominant negative form of Fas, and nucleic acid sequence is present in the modified cell in a recombinant DNA construct, in an mRNA, or in a viral vector.
46. The modified cell, the method, the pharmaceutical composition, the cell of one of embodiments 45 and 22, wherein the nucleic acid sequence is an mRNA, which is not integrated into the genome of the modified cell.
47. The modified cell, the method, the pharmaceutical composition, the cell of one of embodiments 45-23, wherein the nucleic acid sequence is associated with an oxygen-sensitive polypeptide domain.
23. The modified cell, the method, the pharmaceutical composition, the cell of embodiment 23, wherein the oxygen-sensitive polypeptide domain comprises HIF VHL binding domain.
49. The modified cell, the method, the pharmaceutical composition, the cell of one of embodiments 44-47, wherein the nucleic acid sequence is regulated by a promoter comprising a binding site for a transcription modulator that modulates the expression and/or secretion of the therapeutic agent in the cell.
50. The modified cell, the method, the pharmaceutical composition, the cell of embodiment 49, wherein the transcription modulator is or includes Hif1a, NFAT, FOXP3, and/or NFkB.

51. A method of expanding modified cells of any one of embodiments −25, the method comprising reducing or eliminating function or expression of the one or more molecules in the modified cells such that cell death of the modified cells induced by the one or more molecules are reduced as compared to the modified cells of which function of expression of the one or more molecules is not reduced or eliminated.
52. A polynucleotide encoding a dominant negative form of TNFR1, a dominant negative form of TNFR1, and/or a dominant negative form of Fas.
53. A cell modified to express one or more molecules at a level that is higher than the level of the one or more expressed by a cell that has not been modified to expression the one or more molecules, wherein the one or more molecules are overexpressed in cancer cells, associated with recruitment of immune cells, and/or associated with autoimmunity.
54. A modified cell engineered to express an antigen binding molecule, wherein expression and/or function of one or more molecules in the modified cell has been enhanced, where the one or more molecules are overexpressed in cancer cells, associated with recruitment of immune cells, and/or associated with autoimmunity.
55. The modified cell of any one of embodiments 53 and 54, wherein the modified cell comprises a disruption in an endogenous gene or addition of an exogenous gene that is associated with a biosynthesis or transportation pathway of the one or more molecules.
56. A method or use of polynucleotide, the method comprising providing a viral particle (e.g., AAV, lentivirus or their variants) comprising a vector genome, the vector genome comprising the polynucleotide encoding the one more molecules and a polynucleotide encoding a binding molecule, the polynucleotide operably linked to an expression control element conferring transcription of the polynucleotides; and administering an amount of the viral particle to a subject such that the polynucleotide is expressed in the subject, where the one or more molecules are overexpressed in cancer cells, associated with recruitment of immune cells, and/or associated with autoimmunity.
57. The method of embodiment 56, wherein the AAV preparation may include AAV vector particles, empty capsids, and host cell impurities, thereby providing an AAV product substantially free of AAV empty capsids.
58. A pharmaceutical composition comprising the population of the cells of any of embodiments 53-56.
59. A method of causing or eliciting T cell response in a subject in need thereof and/or treating a tumor of the subject, the method comprising administering an effective amount of the composition of embodiment 58 to the subject.
58. An isolated nucleic acid sequence encoding one or more molecules is overexpressed in cancer cells, associated with the recruitment of immune cells, and/or associated with autoimmunity.
60. The isolated nucleic acid sequence, modified cell, method, or pharmaceutical composition of any one of embodiments 53-58, wherein the one more molecules comprise at least one of NRIP3, TNS1, ALXO5, IGF2, SERPINA1, MET, SGK1, ZNF286B, GLI2, a functional variant of the one or more molecules, or a functional fragment of the one or more molecules.
61. The isolated nucleic acid sequence, modified cell, method, or pharmaceutical composition of any one of embodiments 53-59, wherein the one more molecules comprise at least one of CCL19, FLT3L, HMGB, a functional variant of the one or more molecules, or a functional fragment of the one or more molecules.

62. The isolated nucleic acid sequence, modified cell, method, or pharmaceutical composition of any one of embodiments 53-60, wherein the one more molecules comprise at least one of RIPK1, RIPK2, RIPK3, FcRL3, FcRL6, TICAM1, TICAM2, IFIH1, IRF4, RORA, RORC, ACT1, TRAF6, TAB2, TAB3, TAK1, IL17RA, IL17RC, a functional variant of the one or more molecules, or a functional fragment of the one or more molecules.

63. The isolated nucleic acid sequence, modified cell, method, or pharmaceutical composition of embodiment 62, wherein one or more sequences of IGF2, SERPINA1, MET, SGK1, GLI2, TNS1, ALOX5, NRIP3, and/or ZNF286B are overexpressed in the modified cell.

64. The modified cell of any of the preceding embodiments, wherein the modified cell comprises the antigen binding molecule, the antigen binding molecule is the chimeric antigen receptor (CAR), which comprises an antigen-binding domain, a transmembrane domain, and an intracellular signaling domain.

65. The modified cell of embodiment 64, wherein the antigen-binding domain binds to a tumor antigen is selected from a group consisting of: TSHR, CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, PRSS21, VEGFR2, LewisY, CD24, PDGFR-beta, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, and IGLL1.

66. The modified cell of any one of embodiments 64 and 65, wherein the intracellular signaling domain comprises a co-stimulatory signaling domain, or a primary signaling domain and a co-stimulatory signaling domain, wherein the co-stimulatory signaling domain comprises a functional signaling domain of a protein selected from the group consisting of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D 67. The modified cell of any one of suitable embodiments, wherein the modified cell comprises the antigen binding molecule, the antigen binding molecule is a modified TCR.

68. The modified cell of embodiment 67, wherein the TCR is derived from spontaneously occurring tumor-specific T cells in patients.

69. The modified cell of embodiment 68, wherein the TCR binds to a tumor antigen.

70. The modified cell of embodiment 69, wherein the tumor antigen comprises CEA, gp100, MART-1, p53, MAGE-A3, or NY-ESO-1.

71. The modified cell of embodiment 69, wherein the TCR comprises TCRγ and TCRδ Chains or TCRα and TCRβ chains, or a combination thereof.

72. The modified cell of embodiment 21, wherein the cell is an immune effector cell (e.g., a population of immune effector cells), and/or the immune effector cell is a T cell or an NK cell.

73. The modified cell of embodiment 72, wherein the immune effector cell is a T cell.

74. modified cell of embodiment 72 wherein the T cell is a CD4+ T cell, a CD8+ T cell, or a combination thereof.

75. The modified cell of any of the preceding embodiments, wherein the cell is a human cell.

76. The modified cell of any of the preceding embodiments, wherein the enhanced expression and/or function of the one or more molecules is implemented by introducing a nucleic acid sequence encoding the one or more molecules and/or the binding molecule, which is present in the modified cell in a recombinant DNA construct, in an mRNA, or in a viral vector.

77. The modified cell of embodiment 76, wherein the nucleic acid sequence is an mRNA, which is not integrated into the genome of the modified cell.

78. The modified cell of embodiment 76, wherein the nucleic acid sequence is associated with an oxygen-sensitive polypeptide domain.

79. The modified cell of embodiment 78, wherein the oxygen-sensitive polypeptide domain comprises HIF VHL binding domain.

80. The modified cell of embodiment 76, wherein the nucleic acid sequence is regulated by a promoter comprising a binding site for a transcription modulator that modulates the expression and/or secretion of the therapeutic agent in the cell.

81. The modified cell of embodiment 80, wherein the transcription modulator is or includes Hif1a, NFAT, FOXP3, and/or NFkB.

82. A modified cell comprising one or more polynucleotides encoding one or more proteins assembling an extracellular vesicle (EV) and encoding or comprising a therapeutic agent.

83. The modified cell of embodiment 82, wherein the modified cell is engineered to express an antigen binding molecule.
84. The modified cell of one of embodiments 82 and 83, wherein the antigen binding molecule is chimeric antigen receptor (CAR), which comprises an antigen-binding domain, a transmembrane domain, and an intracellular signaling domain.
85. The modified cell of embodiment 84, wherein the antigen-binding domain binds to a tumor antigen is selected from a group consisting of: TSHR, CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, PRSS21, VEGFR2, LewisY, CD24, PDGFR-beta, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, and IGLL1.
86. The modified cell of one of embodiments 84 and 85, wherein the intracellular signaling domain comprises a co-stimulatory signaling domain, or a primary signaling domain and a co-stimulatory signaling domain, wherein the co-stimulatory signaling domain comprises a functional signaling domain of a protein selected from the group consisting of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D.
87. The modified cell of one of embodiments 82-86, wherein the antigen binding molecule is a modified TCR.
88. The modified cell of embodiment 87, wherein the TCR is derived from spontaneously occurring tumor-specific T cells in patients.
89. The modified cell of embodiment 88 wherein the TCR binds to a tumor antigen.
90. The modified cell of embodiment 89, wherein the tumor antigen comprises CEA, gp100, MART-1, p53, MAGE-A3, or NY-ESO-1.
91. The modified cell of embodiment 89, wherein the TCR comprises TCRγ and TCRδ Chains or TCRα and TCRβ chains, or a combination thereof.
92. The modified cell of embodiment 11, wherein the immune effector cell is a T cell or an NK cell, or the cell is an immune effector cell (e.g., a population of immune effector cells).
93. The modified cell of embodiment 92, wherein the immune effector cell is a T cell.
94. The modified cell of embodiment 93, wherein the T cell is a CD4+ T cell, a CD8+ T cell, or a combination thereof.
95. The modified cell of any of the preceding embodiments, wherein the cell is a human cell.
96. The modified cell of any of the preceding embodiments, wherein the modified cell comprises an inhibitor of expression or function of the one or more genes.
97. The modified cell of embodiment 96, wherein the inhibitor is (1) a gene editing system targeted to one or more sites within the gene encoding the one or more genes or a corresponding regulatory elements; (2) nucleic acid encoding one or more components of a gene editing system of the one or more genes; or (3) combinations thereof.
98. A pharmaceutical composition comprising the population of the cells of any of embodiments 82-17.
99. A method of causing or eliciting T cell response in a subject in need thereof and/or treating a tumor of the subject, the method comprising administering an effective amount of the composition of embodiment 98 to the subject.
100. A method of delivering the therapeutic agent, the method comprising administering an effective amount of the composition of embodiment 98 to the subject.
101. The modified cell, the method, the pharmaceutical composition, the cell of one of embodiments 82-100, wherein the one or more polynucleotides are present in the modified cell in a recombinant DNA construct, in an mRNA, or in a viral vector.
102. The modified cell, the method, the pharmaceutical composition, the cell of embodiment 101, wherein the nucleic acid sequence is an mRNA, which is not integrated into the genome of the modified cell.
103. The modified cell, the method, the pharmaceutical composition, the cell of one of embodiments 101-102, wherein the one or more polynucleotides are associated with an oxygen-sensitive polypeptide domain.
104. The modified cell, the method, the pharmaceutical composition, the cell of embodiment 103, wherein the oxygen-sensitive polypeptide domain comprises HIF VHL binding domain.
105. The modified cell, the method, the pharmaceutical composition, the cell of one of embodiments 101-104, wherein expression of the one or more polynucleotide are regulated by a promoter comprising a binding site for a transcription modulator that modulates the expression and/or secretion of the therapeutic agent in the cell.

106. The modified cell, the method, the pharmaceutical composition, the cell of embodiment 105, wherein the transcription modulator is or includes Hif1a, NFAT, FOXP3, and/or NFkB.

107. The modified cell of any preceding embodiments (82-106), wherein expression the one or more polynucleotide is regulated by NFAT such that the EV is assembled in response to activation of the modified cell.

108. The modified cell, the method, the pharmaceutical composition, the cell of any of embodiments 82-107, wherein the one or more proteins are self-assembling proteins.

109. The modified cell, the method, the pharmaceutical composition, the cell of any of embodiments 82-108, wherein the one or more proteins that direct their release through vesicles as a luminal membrane-bound protein is chosen from the group consisting of: the retroviral group specific antigen, retroviral group specific antigen variations, the influenza MI protein, the ARRDCI protein, the ARC protein, the Ebola virus VP40 protein and the M proteins of vesicular stomatitis virus.

110. The modified cell, the method, the pharmaceutical composition, the cell of any of embodiments 82-109, wherein the one or more proteins comprise an Arc protein and the one or more polynucleotides comprise a nucleic acid encoding a therapeutic agent.

111. An EV comprising an Arc protein and a nucleic acid encoding or comprising a therapeutic agent, the nucleic acid is DNA or RNA encoding the therapeutic agent.

112. The modified cell, the method, the pharmaceutical composition, the cell, or the EV of any of embodiments 110 and 111, wherein the therapeutic agent is selected from the group consisting of a siRNA, an shRNA, and RNAi.

113. The modified cell, the method, the pharmaceutical composition, the cell, or the EV of any of embodiments 110 and 111, wherein the nucleic acid encoding a therapeutic agent is linked to a 3' UTR sequence.

114. The modified cell, the method, the pharmaceutical composition, the cell, or the EV of embodiment 113, wherein the 3' UTR sequence is bound to the Arc protein.

115. The modified cell, the method, the pharmaceutical composition, the cell, or the EV of embodiment 114, wherein the 3' UTR sequence is an arc mRNA 3' UTR sequence.

116. The modified cell, the method, the pharmaceutical composition, the cell, or the EV of any of embodiments 110 and 111, wherein the nucleic acid further comprises a transcription modulator sequence.

117. The modified cell, the method, the pharmaceutical composition, the cell, or the EV of any of embodiments 82-37, wherein the therapeutic agent is scFv binding a tumor antigen on the membrane or inside of a tumor cell.

118. The modified cell, the method, the pharmaceutical composition, the cell, or the EV of embodiment 117, wherein the tumor antigen is at least one of the tumor antigens of embodiments 86 and 91.

119. A polynucleotide comprising a binding site of a transcription modulator (e.g., NFAT) and encoding one or more proteins assembling the extracellular vesicle (EV) and the therapeutic agent.

120. A cell modified to express one or more molecules at a level that is higher than the level of the one or more expressed by a cell that has not been modified to expression the one or more molecules, wherein the one or more molecules are associated with biosynthesis and/or transportation of inflammasome.

121. A modified cell engineered to express an antigen binding molecule, wherein the expression and/or function of one or more molecules in the modified cell has been enhanced, where the one or more molecules are associated with biosynthesis and/or transportation of inflammasome.

122. The modified cell of any one of embodiments 120 and 121, wherein the modified cell comprises a disruption in an endogenous gene or addition of an exogenous gene that is associated with a biosynthesis or transportation pathway of the one or more molecules.

123. A method or use of polynucleotide, the method comprising providing a viral particle (e.g., AAV, lentivirus or their variants) comprising a vector genome, the vector genome comprising the polynucleotide encoding the one more molecules and a polynucleotide encoding a binding molecule, the polynucleotide operably linked to an expression control element conferring transcription of the polynucleotides; and administering an amount of the viral particle to a subject such that the polynucleotide is expressed in the subject, where the one or more molecules are associated with biosynthesis and/or transportation of inflammasome.

124. The method of embodiment 123, wherein the AAV preparation may include AAV vector particles, empty capsids, and host cell impurities, thereby providing an AAV product substantially free of AAV empty capsids.

125. A pharmaceutical composition comprising the population of the cells of any of embodiments 120-122.

126. A method of causing or eliciting T cell response in a subject in need thereof and/or treating a tumor of the subject, the method comprising administering an effective amount of the composition of embodiment 125 to the subject.

127. The isolated nucleic acid sequence, modified cell, method, or pharmaceutical composition of any one of embodiments 120-126, wherein the one more molecules comprise at least one of NLRR1, NLRP3, ASC, PYD, NOD2, CARD, RIP2, RICK, TBK1, and TAK1/2, a functional variant of the one or more molecules, or a functional fragment of the one or more molecules.

128. The isolated nucleic acid sequence, modified cell, method, or pharmaceutical composition of any one of embodiments 120-127, wherein the one or more molecules comprise at least one of NLRP1, NLRP3, and TBK1, a functional variant of the one or more molecules, or a functional fragment of the one or more molecules.

129. The isolated nucleic acid sequence, modified cell, method, or pharmaceutical composition of any one of embodiments 120-128, wherein the one or more molecules comprise at least one of sequences of NLRP1 mutant1 A54V, NLRP1 mutant2 A66V, NLRP1 mutant3 M1184V, NLRP1 mutant4, Missing 787-843, NLRP1 wt, NLRP3 wt, ASC-wt, NLRP3 mutant1, NLRP3 mutant2, NLRP3 mutant3, or NLRP3 mutant4 (Sequences were disclosed in U.S. Patent Application No. 62/914,678).

130. The isolated nucleic acid sequence, modified cell, method, or pharmaceutical composition of embodiment 129, wherein one or more sequences of NLRP1 mutant1 A54V, NLRP1 mutant2 A66V, NLRP1 mutant3 M1184V, NLRP1 mutant4, Missing 787-843, NLRP1 wt, NLRP3 wt, ASC-wt, NLRP3 mutant1, NLRP3 mutant2, NLRP3 mutant3, or NLRP3 mutant4 (Sequences were disclosed in U.S. Patent Application No. 62/914,678) are overexpressed in the modified cell.

131. The modified cell of any of the preceding embodiments, wherein the modified cell comprises the antigen binding molecule, the antigen binding molecule is the chimeric antigen receptor (CAR), which comprises an antigen-binding domain, a transmembrane domain, and an intracellular signaling domain.

132. The modified cell of embodiment 131, wherein the antigen-binding domain binds to a tumor antigen is selected from a group consisting of: TSHR, CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, PRSS21, VEGFR2, LewisY, CD24, PDGFR-beta, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, and IGLL1.

133. The modified cell of any one of embodiments 131 and 132, wherein the intracellular signaling domain comprises a co-stimulatory signaling domain, or a primary signaling domain and a co-stimulatory signaling domain, wherein the co-stimulatory signaling domain comprises a functional signaling domain of a protein selected from the group consisting of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D 134. The modified cell of any one of suitable embodiments, wherein the modified cell comprises the antigen binding molecule, the antigen binding molecule is a modified TCR.

135. The modified cell of embodiment 134, wherein the TCR is derived from spontaneously occurring tumor-specific T cells in patients.

136. The modified cell of embodiment 135, wherein the TCR binds to a tumor antigen.

137. The modified cell of embodiment 136, wherein the tumor antigen comprises CEA, gp100, MART-1, p53, MAGE-A3, or NY-ESO-1.

138. The modified cell of embodiment 136, wherein the TCR comprises TCRγ and TCRδ Chains or TCRα and TCRβ chains, or a combination thereof.

139. The modified cell of any of the preceding embodiments, wherein the immune effector cell is a T cell or an NK cell, or the cell is an immune effector cell (e.g., a population of immune effector cells).

140. The modified cell of embodiment 139, wherein the immune effector cell is a T cell.

141. modified cell of embodiment 139 wherein the T cell is a CD4+ T cell, a CD8+ T cell, or a combination thereof.

142. The modified cell of any of the preceding embodiments, wherein the cell is a human cell.

143. The modified cell of any of the preceding embodiments, wherein the enhanced expression and/or function of the one or more molecules is implemented by introducing a nucleic acid sequence encoding the one or more molecules and/or the binding molecule, which is present in the modified cell in a recombinant DNA construct, in an mRNA, or in a viral vector.

144. The modified cell of embodiment 143, wherein the nucleic acid sequence is an mRNA, which is not integrated into the genome of the modified cell.

145. The modified cell of embodiment 143, wherein the nucleic acid sequence is associated with an oxygen-sensitive polypeptide domain.

146. The modified cell of embodiment 145, wherein the oxygen-sensitive polypeptide domain comprises HIF VHL binding domain.

147. The modified cell of embodiment 143, wherein the nucleic acid sequence is regulated by a promoter comprising a binding site for a transcription modulator that modulates the expression and/or secretion of the therapeutic agent in the cell.

148. The modified cell of embodiment 147, wherein the transcription modulator is or includes Hif1a, NFAT, FOXP3, and/or NFkB.

149. An isolated nucleic acid sequence encoding the one or more molecules of any preceding embodiments are associated with biosynthesis and/or transportation of inflammasome.

EXAMPLES

Figure 2:
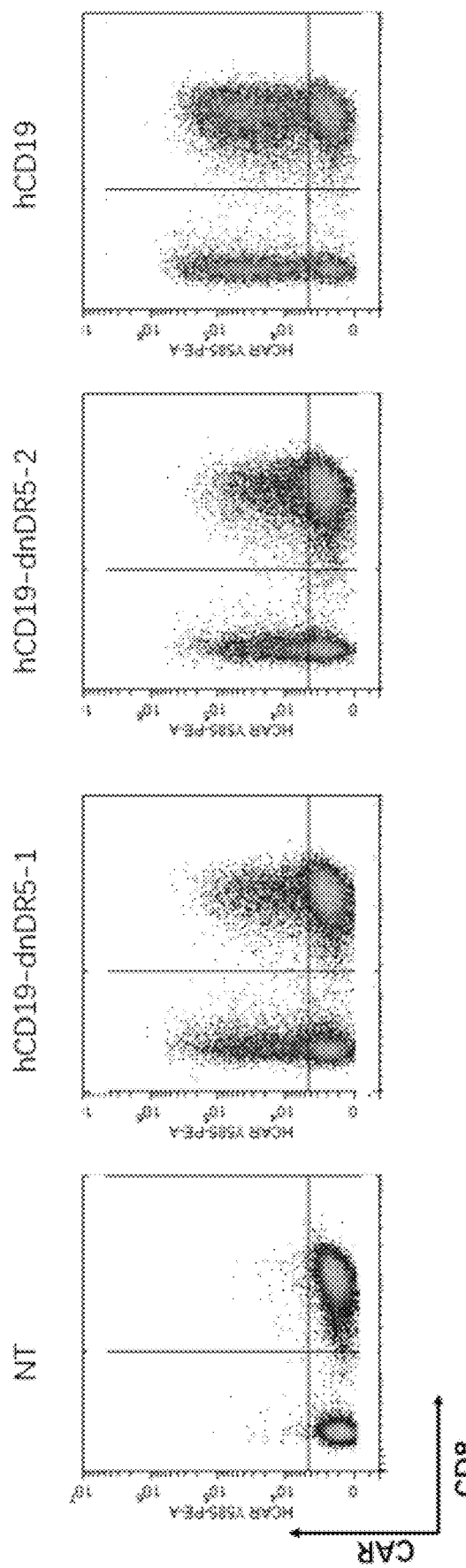
FIG. 2 shows flow cytometry results of expression of humanized CD19 CAR and various forms of dnDR5.

FIG. 1 shows vectors encoding CD19 CAR and dnDR5 (dominant negative DR5). FIG. 2 shows flow cytometry results of expression of humanized CD19 CAR and various forms of dnDR5. The expression of hCD19 CAR (human CD19 CAR) was normal after T cells were infected with hCD19-DNDR5-1 and hCD19-dnDR5-2, and DR5 is the receptor of Trail. Sequences are provided in Table 2, and additional information of the sequences may be found in PCT Patent Publications WO2020106843 and WO2019140100 and in PCT Patent Application NO: PCT/US20/13099, which are incorporated herein by reference in their entirety.

Figure 3:
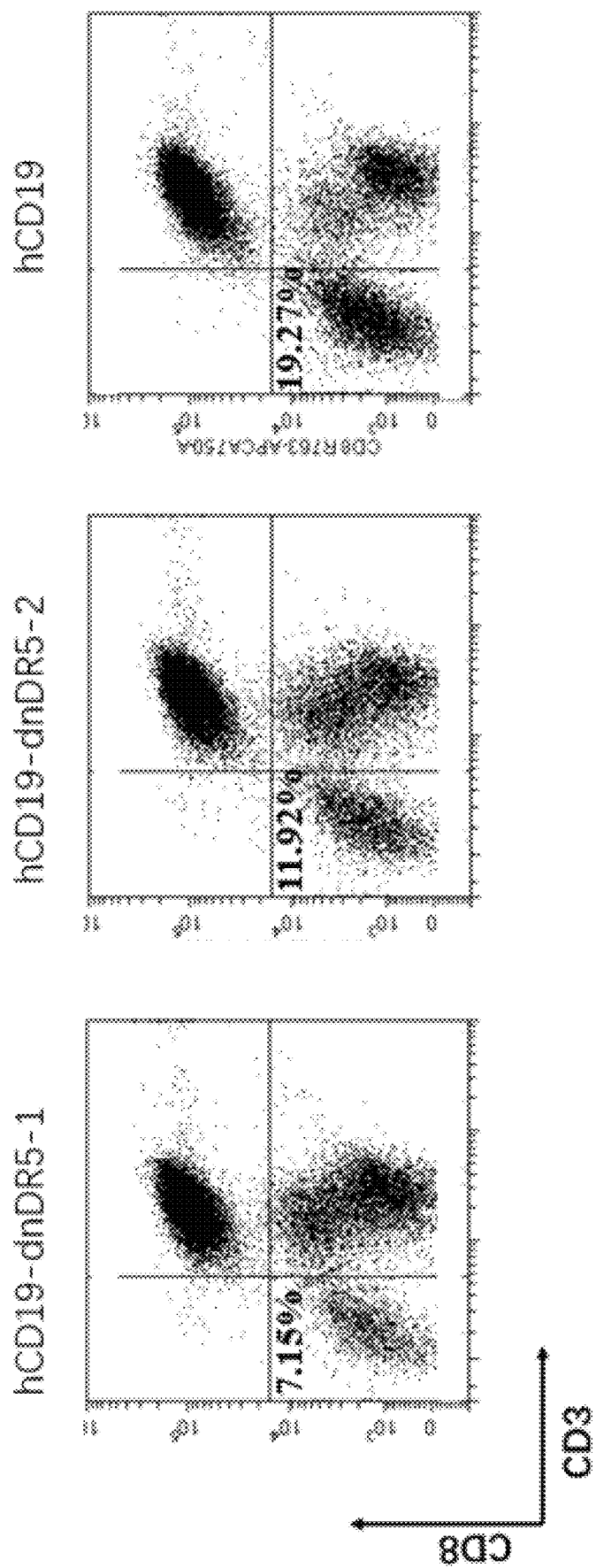
FIGS. 3, 4, 5, and 6 show flow cytometry results of the co-culturing analysis.

FIGS. 3-6 show flow cytometry results of the co-culturing analysis. As shown in FIG. 3, T cells including hCD19 CAR and various forms of dnDR5 and TRAIL-GFP Nalm6 cells (substrate cells of CD19 CAR T), were co-cultured at a ratio of 3:1. The killing effect of T cells was detected by flow cytometry at 24 h. The percentage of killed Nalm6 in the hCD19 CAR T group was 19.27%, The percentage of killed Nalm6 in the hCD19-dnDR5-1 group was 7.15%, and the percentage of killed Nalm6 in the hCD19-dnDR5-2 group was 11.92%. In the hCD19-dnDR5-1 and hCD19-dnDR5-2 groups, the percentages of killed tumor cells (Nalm6) were lower, indicating that hCD19-dnDR5-1 and hCD19-dnDR5-2 had a better killing effect. Trail-GFP Nalm6 cells are the substrate cells of hCD19-dnDR5-1 CART and hCD19-dnDR5-2 CART.

Figure 4:
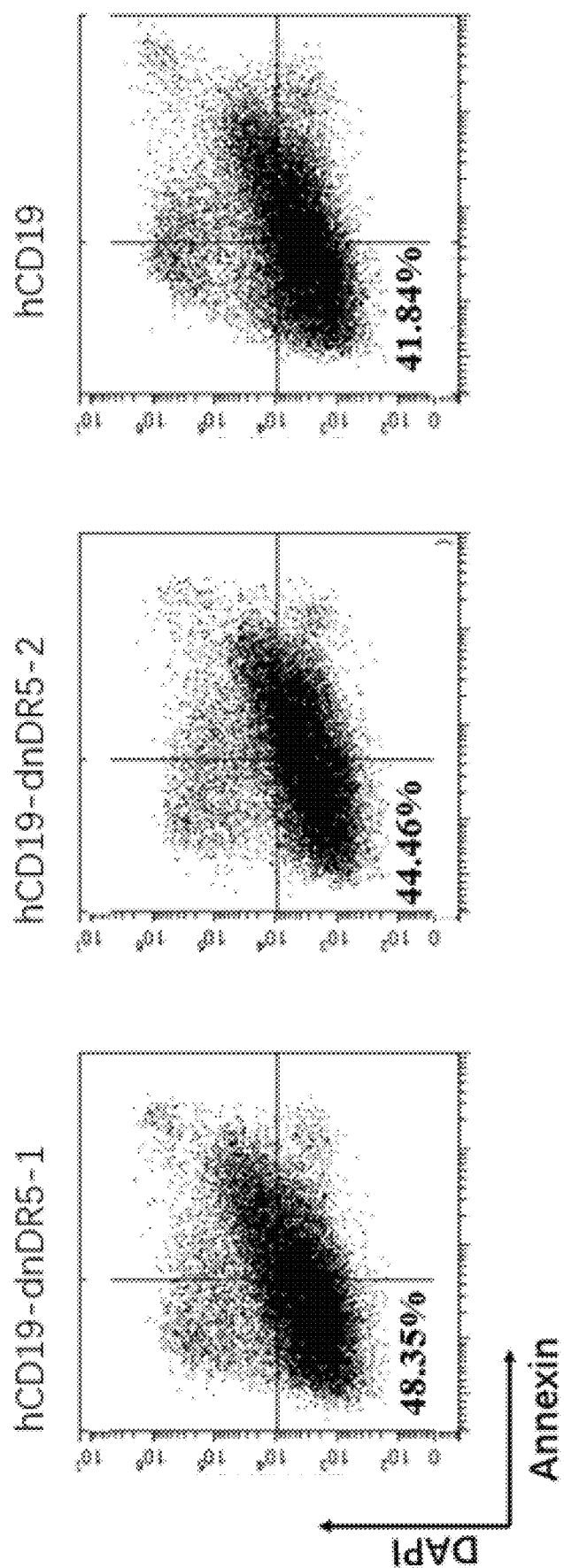

In FIG. 4, T cells and TRAIL-GFP Nalm6 cells were co-cultured at a ratio of 3:1. The exhaustion of T cells was detected by flow cytometry at 24 h. The percentage of non-exhausted T cells in the hCD19 CART group was 41.84%. The percentage of non-exhausted T cells in the hCD19-dnDR5-1 group was 48.35%, and the percentage of non-exhausted T cells in the hCD19-dnDR5-2 group was 44.46%. In the hCD19-dnDR5-1 and hCD19-dnDR5-2 groups, the percentage s of non-exhausted T cells were higher, indicating that hCD19-dnDR5-1 and hCD19-dnDR5-2 had an anti-exhaustion effect.

Figure 5:
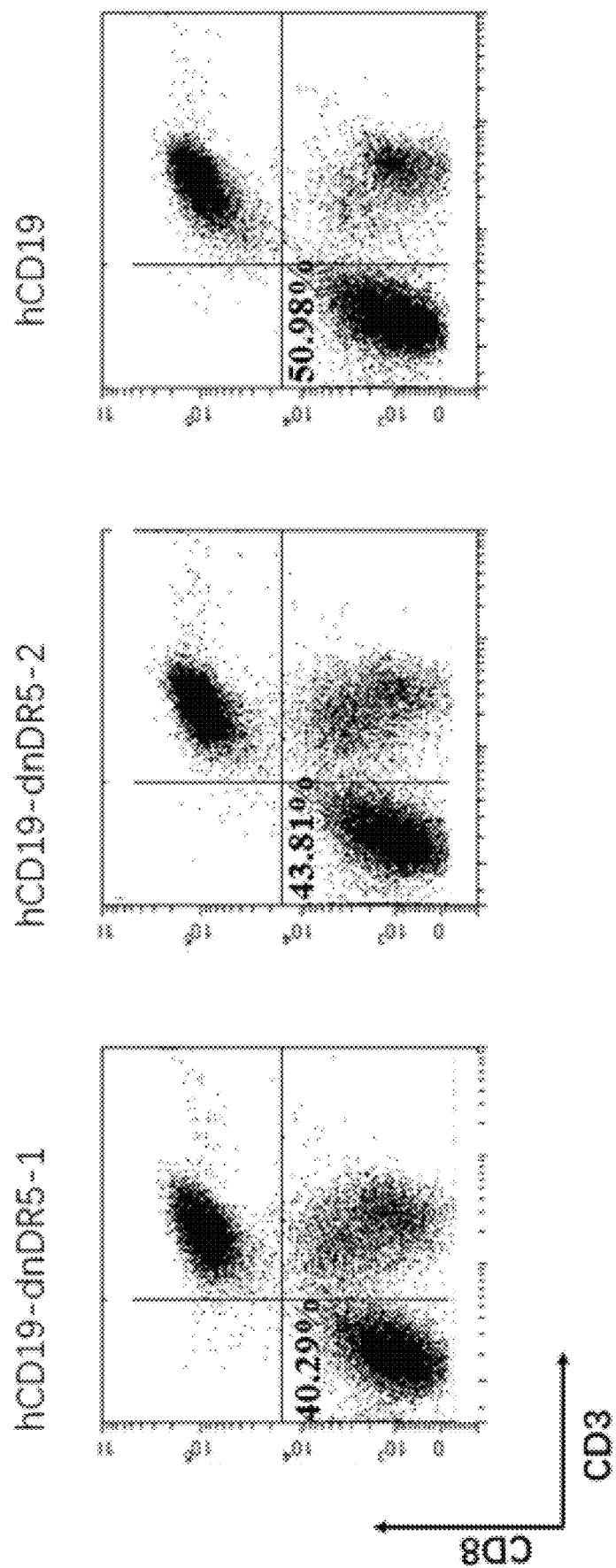

In FIG. 5, T cells and TRAIL-GFP Nalm6 cells were co-cultured at a ratio of 1:1. The killing effect of T cells was detected by flow cytometry at 24 h. The percentage of killed Nalm6 in the hCD19 CART group was 50.98%. The percentage of killed Nalm6 in the hCD19-dnDR5-1 group was 40.29%, and the percentage of killed Nalm6 in the hCD19-dnDR5-2 group was 43.81%. In the hCD19-dnDR5-1 and hCD19-dnDR5-2 groups, and the percentages of killed tumor cells (Nalm6) were lower, indicating that hCD19-dnDR5-1 and hCD19-dnDR5-2 had a better killing effect.

Figure 6:
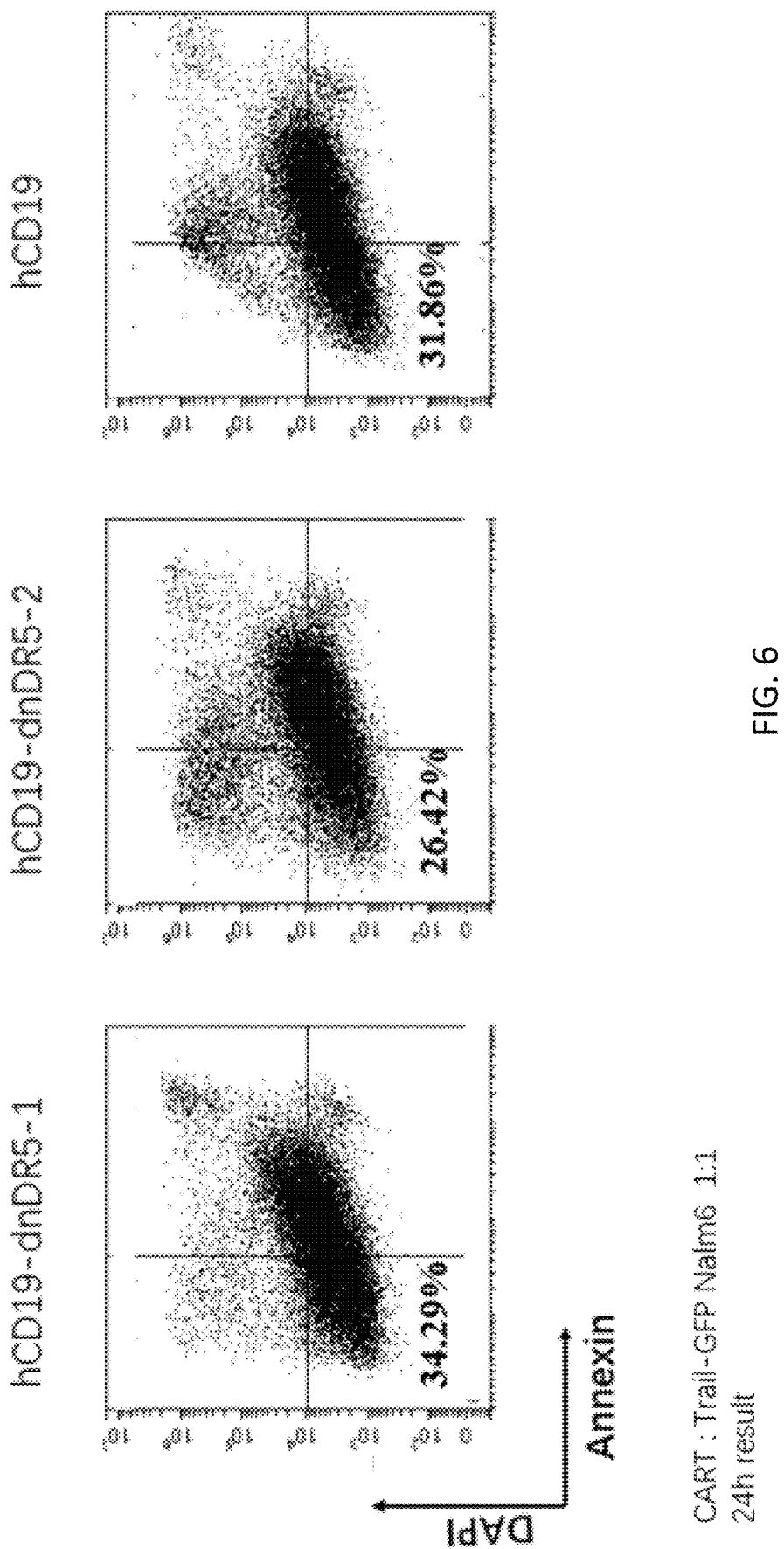
Figure 7:
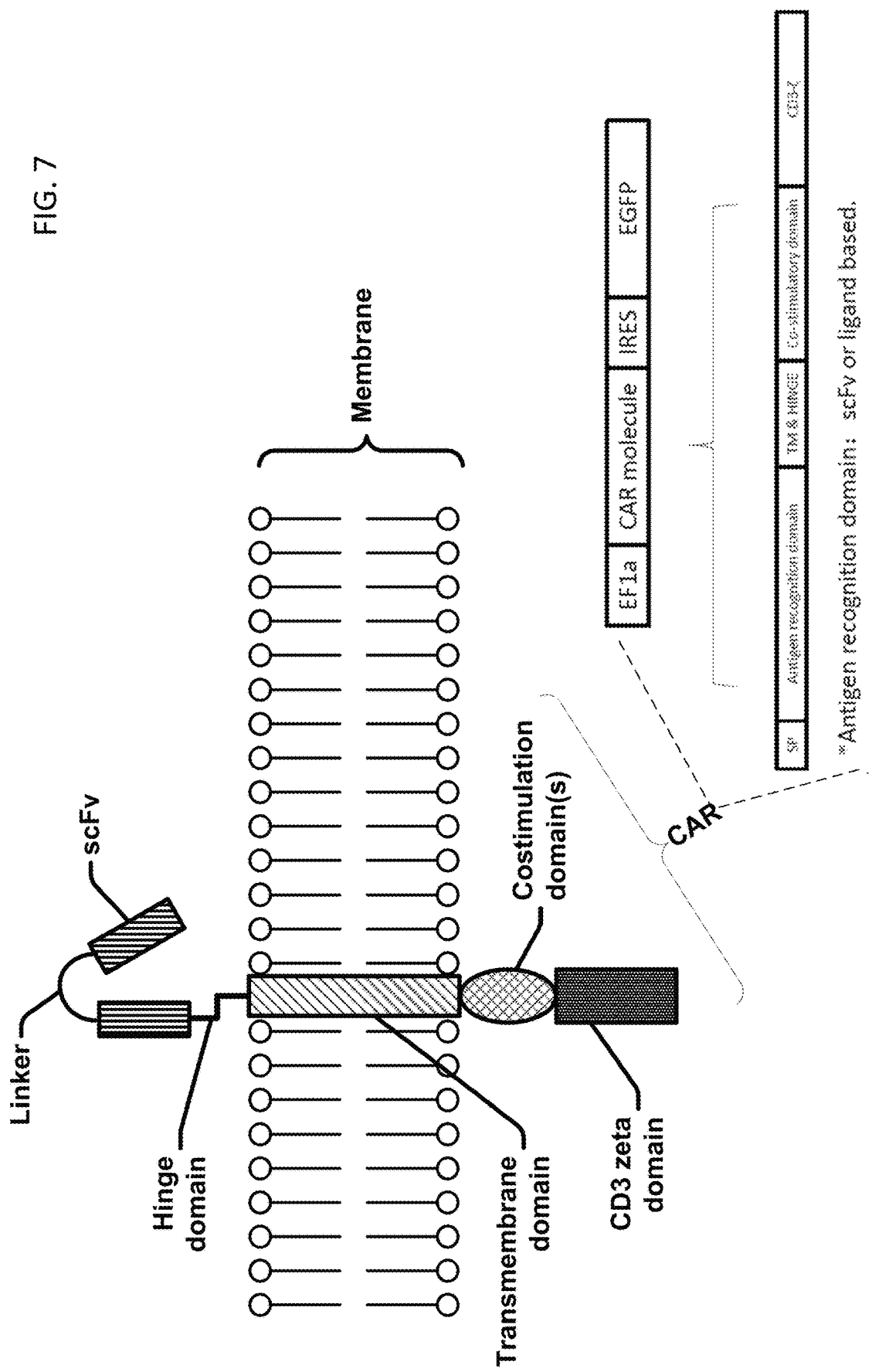
FIG. 7 shows a schematic diagram of CAR and a portion of a cell modified to express at least one of NRIP3, TNS1, ALXO5, IGF2, SERPINA1, MET, SGK1, ZNF286B, GLI2, a functional variant of the one or more molecules, or a functional fragment of the one or more molecules.
Figure 8:
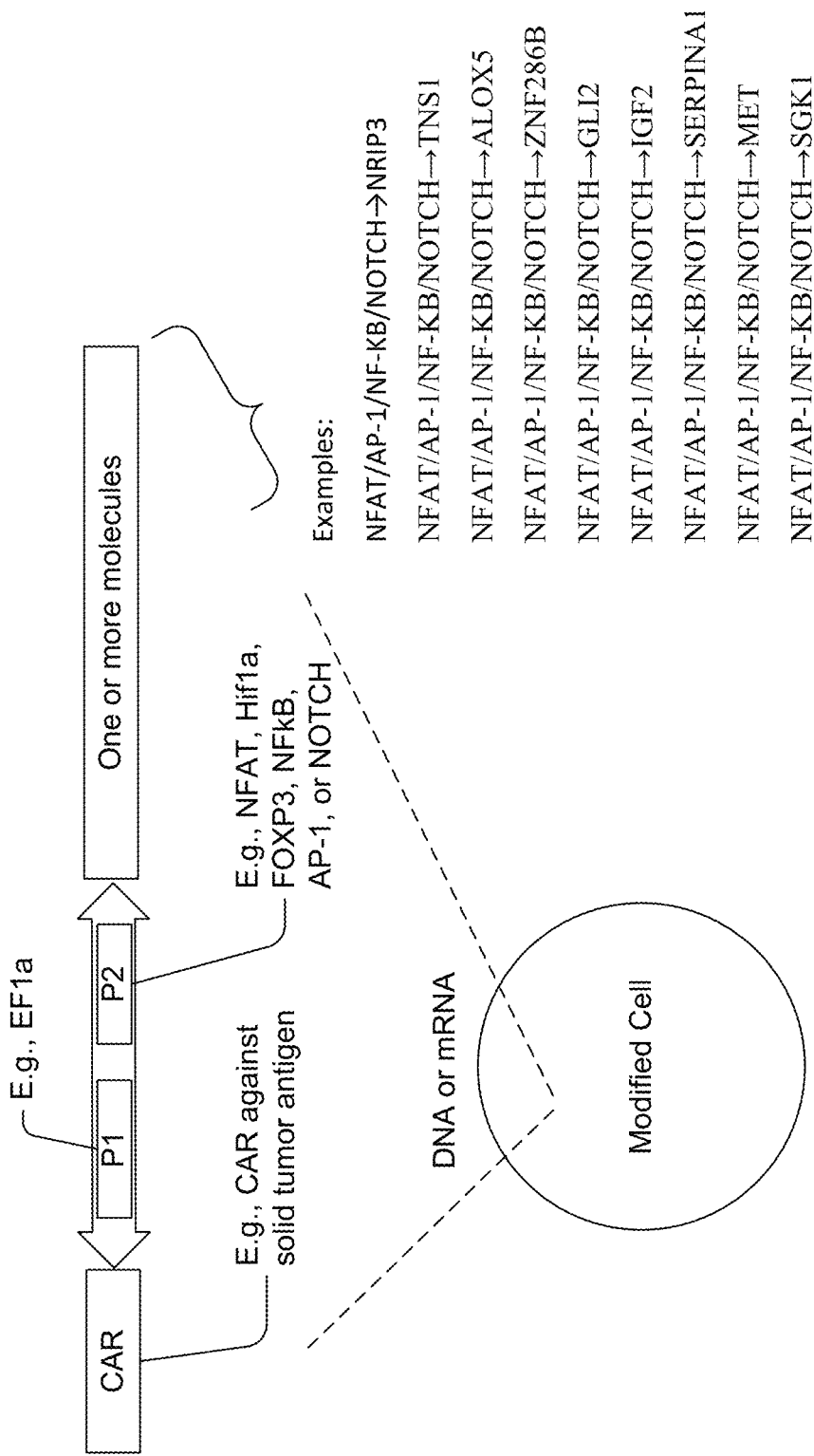
FIG. 8 shows a schematic diagram of a polynucleotide and a cell modified to express at least one of NRIP3, TNS1, ALXO5, IGF2, SERPINA1, MET, SGK1, ZNF286B, GLI2, a functional variant of the one or more molecules, or a functional fragment of the one or more molecules.
Figure 9:
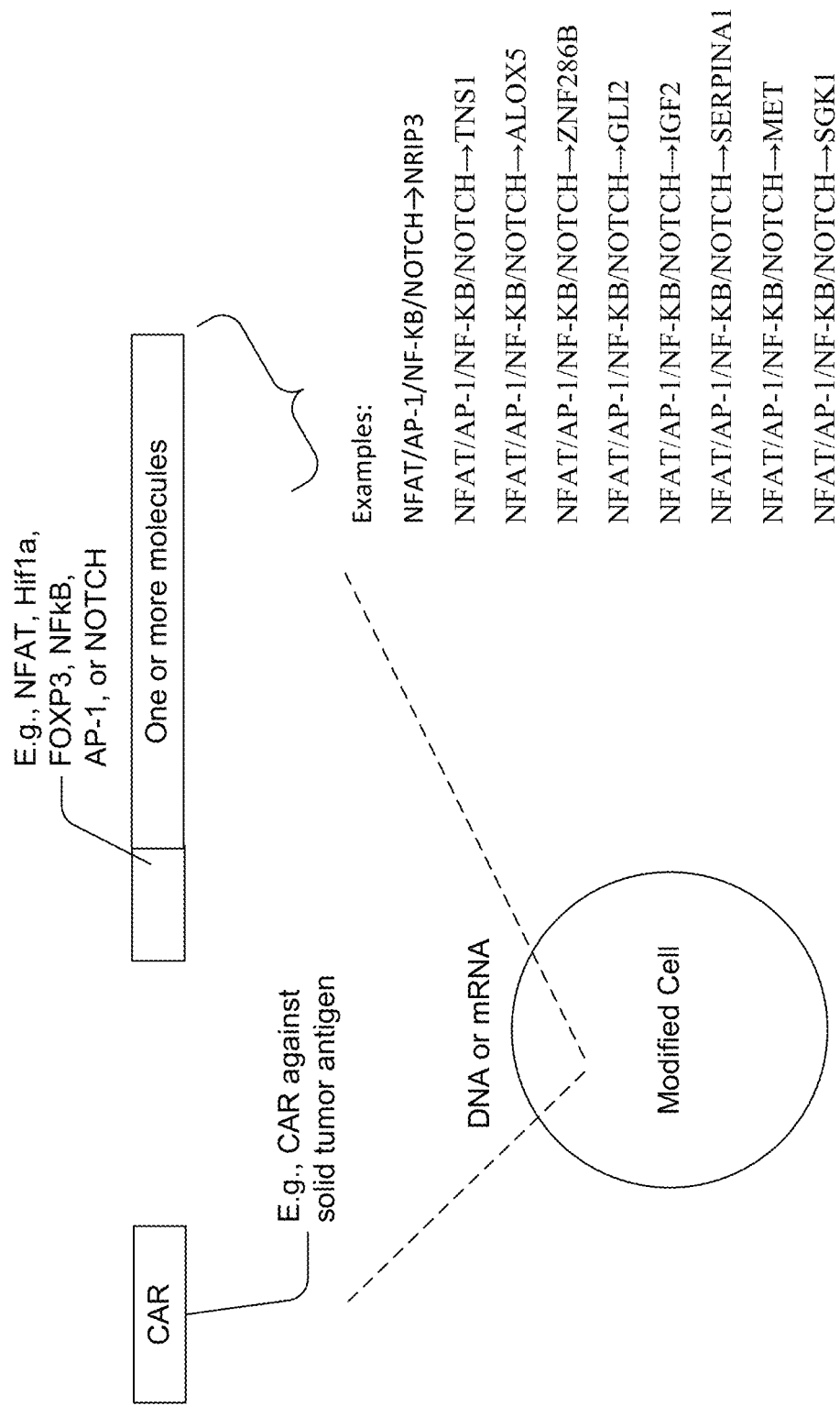
FIG. 9 shows a schematic diagram of multiple polynucleotides and a cell modified to express at least one of NRIP3, TNS1, ALXO5, IGF2, SERPINA1, MET, SGK1, ZNF286B, GLI2, a functional variant of the one or more molecules, or a functional fragment of the one or more molecules.
Figure 10:
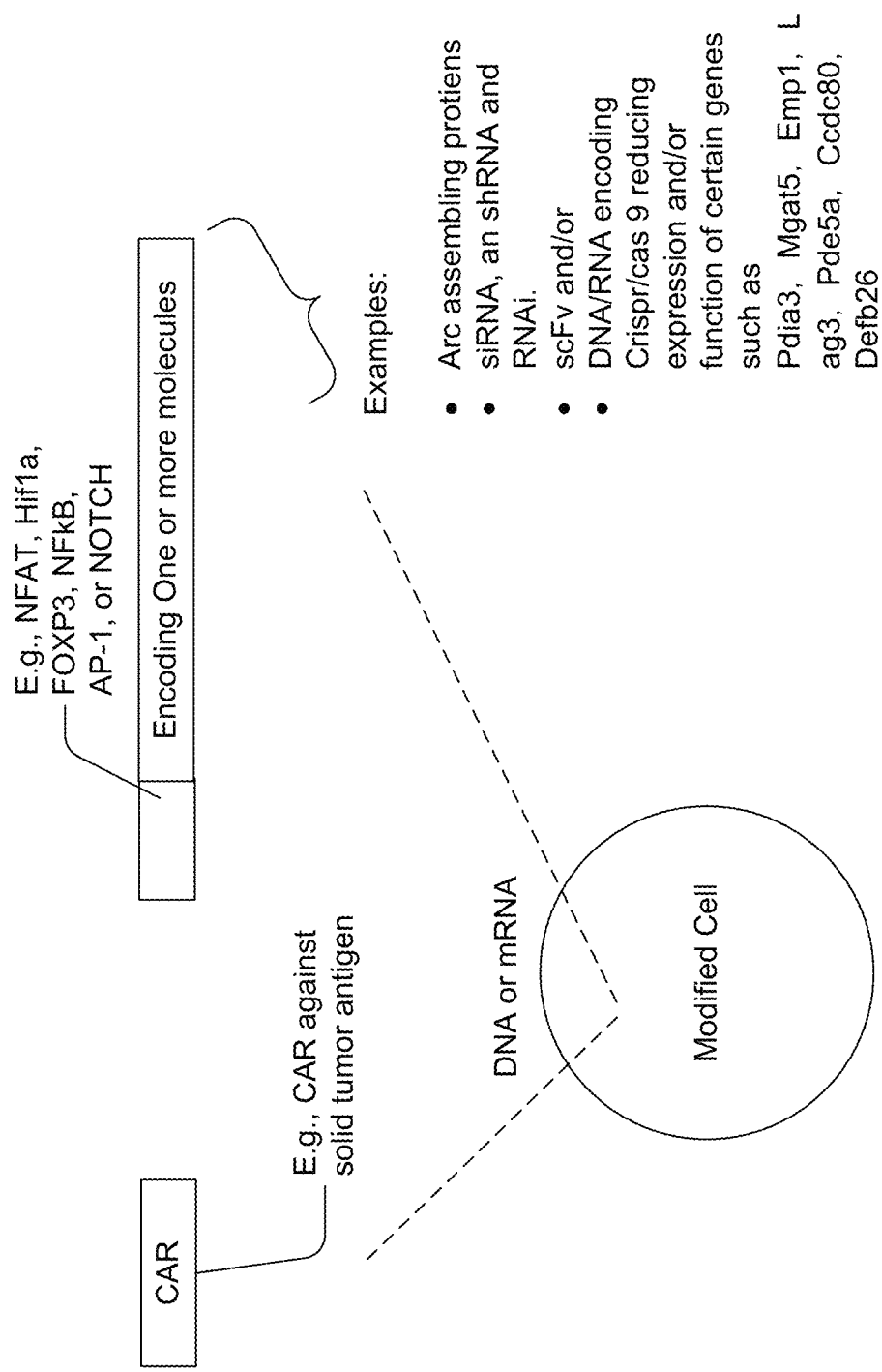
FIG. 10 shows a schematic diagram of multiple polynucleotides and a modified cell comprising one or more polynucleotides encoding one or more proteins assembling an extracellular vesicle (EV) and encoding or comprising a therapeutic agent.
Figure 11:
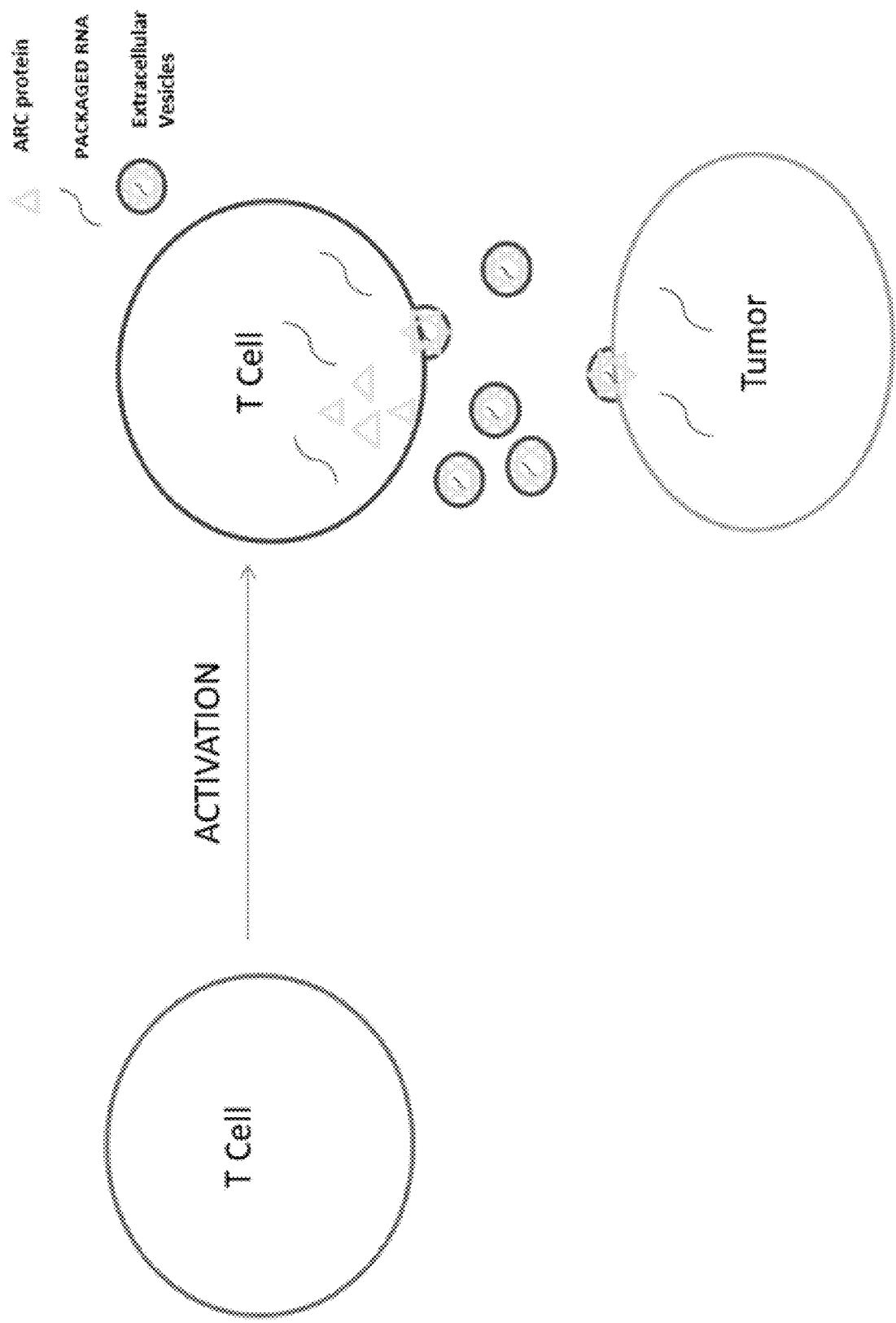
FIG. 11 shows a schematic diagram of cells releasing extracellular vesicles to treat a tumor.
Figure 12:
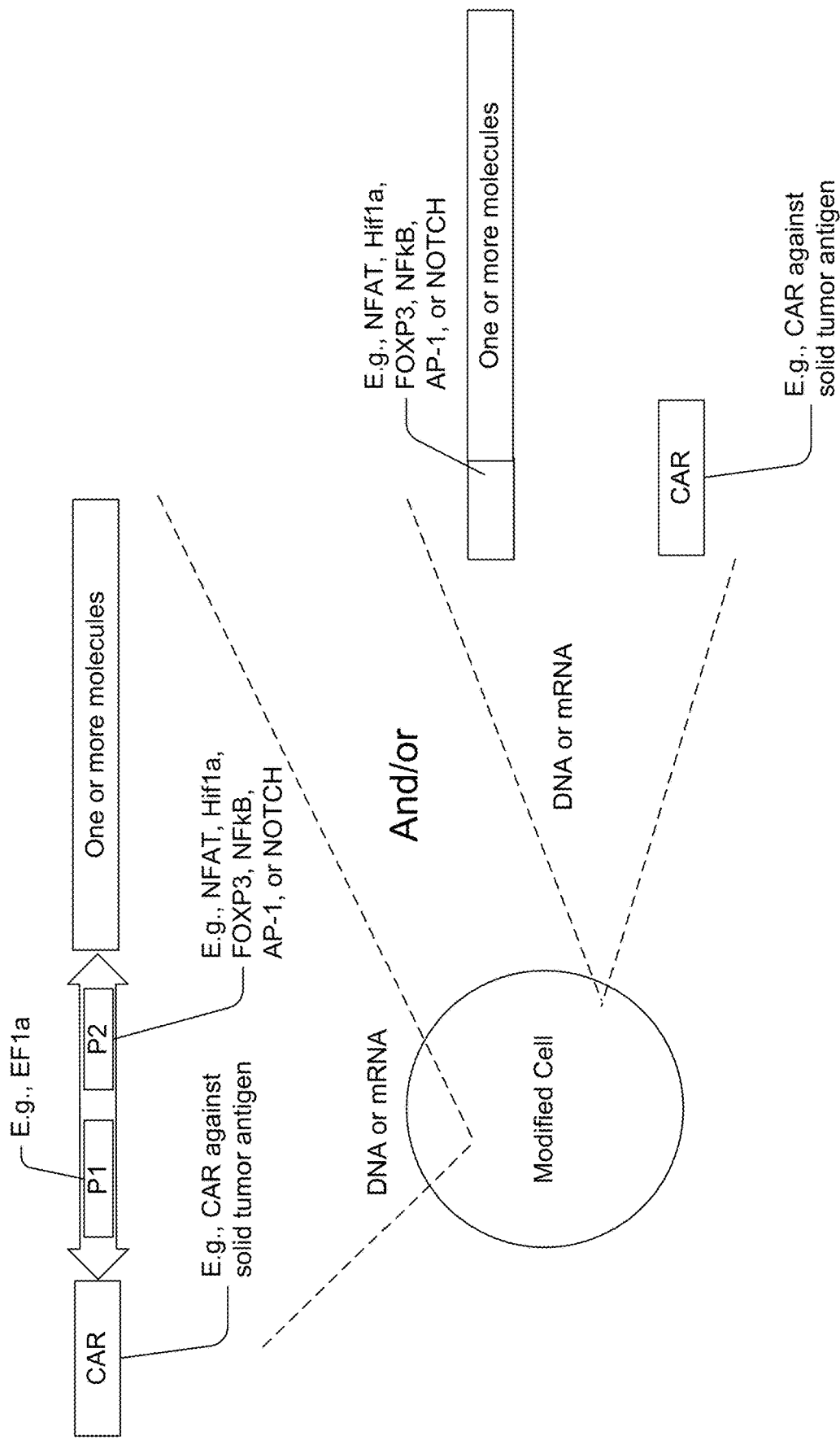
FIG. 12 show a schematic diagram of a polynucleotide, and a modified cell associated with one or more molecules are associated with biosynthesis and/or transportation of NLRR1 and/or NLRP3.
Figure 13:
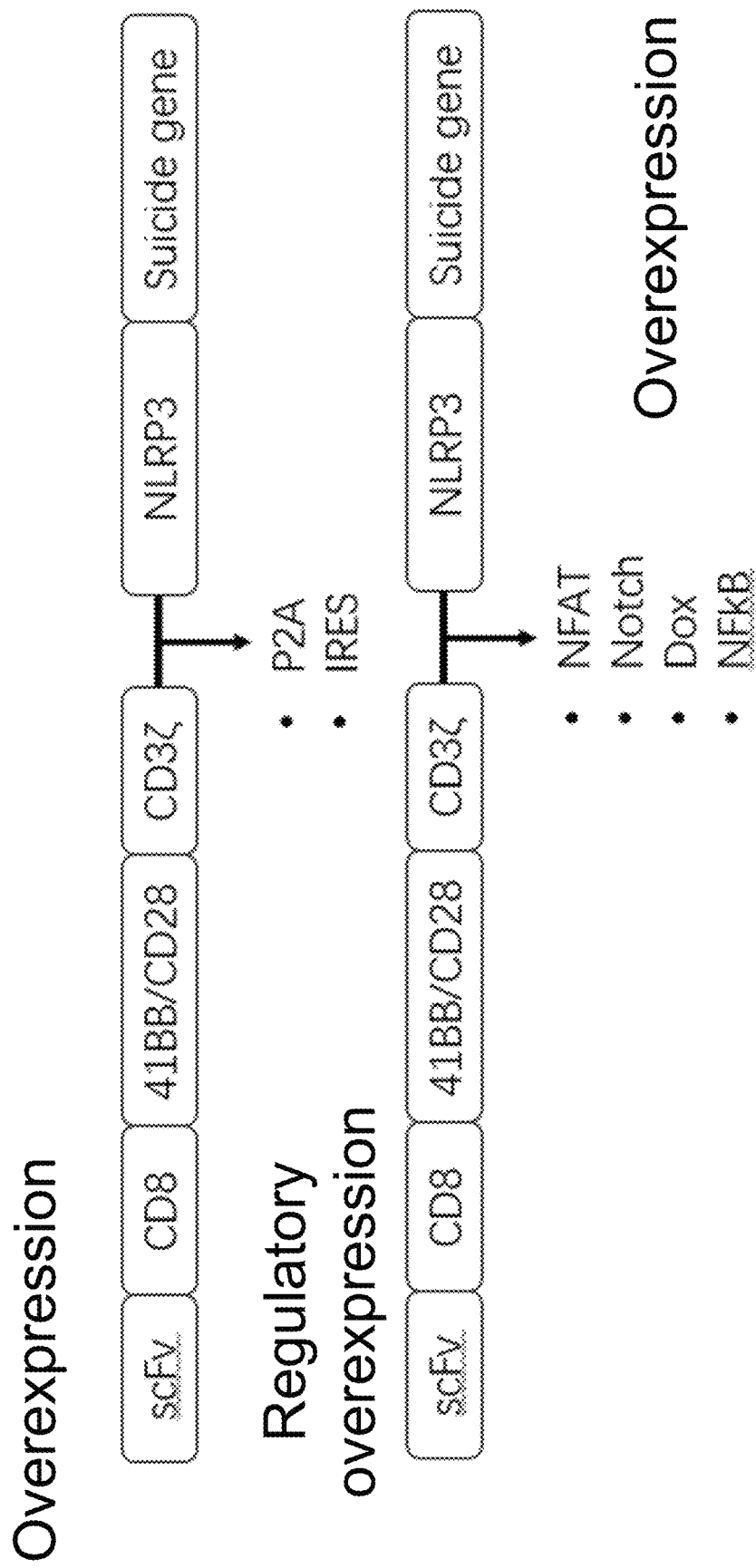
FIG. 13 shows a schematic diagram of multiple polynucleotides associated with one or more molecules that are associated with biosynthesis and/or transportation of NLRR1 and/or NLRP3.

In FIG. 6, T cells and TRAIL-GFP Nalm6 cells were co-cultured at a ratio of 1:1. The exhaustion of T cells was detected by flow cytometry at 24 h. The percentage of non-exhausted T cells in the hCD19 CART group was 31.86%. The percentage of non-exhausted T cells in the hCD19-dnDR5-1 group was 34.29%, and the percentage of non-exhausted T cells in the hCD19-dnDR5-2 group was 26.42%. In the hCD19-dnDR5-1 group, the percentages of non-exhausted T cells were higher, indicating that hCD19-dnDR5-1 had an anti-exhaustion effect.

TABLE 2

| SEQ ID NO | Identifier | Notes |
| --- | --- | --- |
| 1 | dnDR5-1 | amino acid |
| 2 | dnDR5-2 | amino acid |
| 3 | scFv Humanized CD19 | amino acid |
| 4 | CD8 hinge/transmembrane | amino acid |
| 5 | 4-1BB | amino acid |
| 6 | CD3 | amino acid |
| 7 | The dominant negative form of - TNR1A | amino acid |
|  | The dominant negative form of-TNR1B | amino acid |
| 8 | NLRP1 mutant1 A54V | gain-of-function alleles that predispose to inflammasome activation, increase IL1B release activate Inflammation and autoimmunity |
| 9 | NLRP1 mutant2 A66V | gain-of-function alleles that predispose to inflammasome activation, increase IL1B release activate Inflammation and autoimmunity |
| 10 | NLRP1 mutant3 M1184V | gain-of-function alleles that predispose to inflammasome activation, increase IL1B release, activate Inflammation and autoimmunity |
| 11 | NLRP1 mutant4 Missing 787-843 | increase NLRP1-inflammasome complex assembly, stimulate inflammatory responses |
| 12 | NLRP1 mutant1 A54V | gain-of-function alleles that predispose to inflammasome activation, increase IL1B release activate Inflammation and autoimmunity |
| 13 | NLRP1 mutant2 A66V | gain-of-function alleles that predispose to inflammasome activation, increase IL1B release, activate Inflammation and autoimmunity |
| 14 | NLRP1 mutant3 M1184V | gain-of-function alleles that predispose to inflammasome activation, increase IL1B release, activate Inflammation and autoimmunity |
| 15 | NLRP1 mutant4 Missing 787-843 | increase NLRP1-inflammasome complex assembly, stimulate inflammatory responses |

What is claimed is:

1. A modified cell comprising a polynucleotide encoding a dominant negative form of Death receptor 5 (dnDR5), wherein the dnDR5 comprises amino acid sequence SEQ ID NO: 1 or 2.

2. The modified cell of claim 1, wherein the modified cell further comprises a chimeric antigen receptor (CAR).

3. The modified cell of claim 2, wherein the CAR comprises an antigen-binding domain, a transmembrane domain, and an intracellular signaling domain.

4. The modified cell of claim 3, wherein the antigen-binding domain binds a tumor antigen, and wherein the tumor antigen comprises TSHR, CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, PRSS21, VEGFR2, Lewis Y, CD24, PDGFR-beta, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, GM3, TGS5, HMWMAA, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, MAGE A1, ETV6-AML, sperm protein 17, XAGE1, Tie 2, MAD-CT-1, MAD-CT-2, Fos-related antigen 1, p53, p53 mutant, prostein, survivin, telomerase, PCTA-1 (Galectin 8), MelanA (MART1), Ras mutant, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase (hTERT), RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, MAGE A4, CLDN 18.2, GCC (GUCY2C), or IGLL1.

5. The modified cell of claim 3, wherein the intracellular signaling domain comprises a co-stimulatory signaling domain, or a primary signaling domain and a co-stimulatory signaling domain, wherein the co-stimulatory signaling domain comprises a functional signaling domain of a protein, and wherein the protein comprises CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11 a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, or NKG2D.

6. The modified cell of claim 1, wherein the modified cell further comprises a modified TCR.

7. The modified cell of claim 6, wherein the TCR is derived from spontaneously occurring tumor-specific T cells in patients.

8. The modified cell of claim 6, wherein the TCR binds a tumor antigen.

9. The modified cell of claim 8, wherein the tumor antigen comprises CEA, gp100, MART-1, p53, MAGE-A3, or NY-ESO-1.

10. The modified cell of claim 6, wherein the TCR comprises TCRγ and TCRδ chains or TCRα and TCRβ chains, or a combination thereof.

11. The modified cell of claim 1, wherein the modified cell is an immune effector cell.

12. The modified cell of claim 11, wherein the immune effector cell is a T cell or an NK cell.

13. The modified cell of claim 11, wherein the immune effector cell is a T cell.

14. The modified cell of claim 13, wherein the T cell is a CD4+ T cell, a CD8+ T cell, or a combination thereof.

15. The modified cell of claim 1, wherein the cell is a human cell.

16. A pharmaceutical composition comprising the modified cell of claim 1.

17. A polynucleotide encoding a dominant negative form of Death receptor 5 (dnDR5) comprising amino acid sequence SEQ ID NO: 1 or 2.

* * * * *

SEQUENCE LISTING

```
<160> NUMBER OF SEQ ID NOS: 15

<210> SEQ ID NO 1
<211> LENGTH: 356
<212> TYPE: PRT
<213> ORGANISM: Artificial Sequence
<220> FEATURE:
<223> OTHER INFORMATION: Synthesized

<400> SEQUENCE: 1

Met Glu Gln Arg Gly Gln Asn Ala Pro Ala Ala Ser Gly Ala Arg Lys
1               5                   10                  15
```

```
Arg His Gly Pro Gly Pro Arg Glu Ala Arg Gly Ala Arg Pro Gly Pro
            20                  25                  30

Arg Val Pro Lys Thr Leu Val Leu Val Ala Ala Val Leu Leu Leu
        35                  40                  45

Val Ser Ala Glu Ser Ala Leu Ile Thr Gln Gln Asp Leu Ala Pro Gln
 50                  55                  60

Gln Arg Ala Ala Pro Gln Gln Lys Arg Ser Ser Pro Ser Glu Gly Leu
 65                  70                  75                  80

Cys Pro Pro Gly His His Ile Ser Glu Asp Gly Arg Asp Cys Ile Ser
                    85                  90                  95

Cys Lys Tyr Gly Gln Asp Tyr Ser Thr His Trp Asn Asp Leu Leu Phe
               100                 105                 110

Cys Leu Arg Cys Thr Arg Cys Asp Ser Gly Glu Val Glu Leu Ser Pro
           115                 120                 125

Cys Thr Thr Thr Arg Asn Thr Val Cys Gln Cys Glu Glu Gly Thr Phe
 130                 135                 140

Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
                165                 170                 175

Glu Cys Val His Lys Glu Ser Gly Thr Lys His Ser Gly Glu Val Pro
            180                 185                 190

Ala Val Glu Glu Thr Val Thr Ser Ser Pro Gly Thr Pro Ala Ser Pro
        195                 200                 205

Cys Ser Leu Ser Gly Ile Ile Ile Gly Val Thr Val Ala Ala Val Val
210                 215                 220

Leu Ile Val Ala Val Phe Val Cys Lys Ser Leu Leu Trp Lys Lys Val
225                 230                 235                 240

Leu Pro Tyr Leu Lys Gly Ile Cys Ser Gly Gly Gly Asp Pro Glu
                245                 250                 255

Arg Val Asp Arg Ser Ser Gln Arg Pro Gly Ala Glu Asp Asn Val Leu
            260                 265                 270

Asn Glu Ile Val Ser Ile Leu Gln Pro Thr Gln Val Pro Glu Gln Glu
        275                 280                 285

Met Glu Val Gln Glu Pro Ala Glu Pro Thr Gly Val Asn Met Leu Ser
290                 295                 300

Pro Gly Glu Ser Glu His Leu Leu Glu Pro Ala Glu Ala Glu Arg Ser
305                 310                 315                 320

Gln Arg Arg Arg Leu Leu Val Pro Ala Asn Glu Gly Asp Pro Thr Glu
                325                 330                 335

Thr Leu Leu Ser Ser Gly Lys Phe Met Tyr Leu Glu Gly Asn Ala Asp
        340                 345                 350

Ser Ala Met Ser
        355

<210> SEQ ID NO 2
<211> LENGTH: 341
<212> TYPE: PRT
<213> ORGANISM: Artificial Sequence
<220> FEATURE:
<223> OTHER INFORMATION: Synthesized

<400> SEQUENCE: 2

Met Glu Gln Arg Gly Gln Asn Ala Pro Ala Ala Ser Gly Ala Arg Lys
 1               5                   10                  15
```

Arg His Gly Pro Gly Pro Arg Glu Ala Arg Gly Ala Arg Pro Gly Pro
            20                  25                  30

Arg Val Pro Lys Thr Leu Val Leu Val Val Ala Ala Val Leu Leu Leu
        35                  40                  45

Val Ser Ala Glu Ser Ala Leu Ile Thr Gln Gln Asp Leu Ala Pro Gln
50                  55                  60

Gln Arg Ala Ala Pro Gln Gln Lys Arg Ser Ser Pro Ser Glu Gly Leu
65                  70                  75                  80

Cys Pro Pro Gly His His Ile Ser Glu Asp Gly Arg Asp Cys Ile Ser
                85                  90                  95

Cys Lys Tyr Gly Gln Asp Tyr Ser Thr His Trp Asn Asp Leu Leu Phe
            100                 105                 110

Cys Leu Arg Cys Thr Arg Cys Asp Ser Gly Glu Val Glu Leu Ser Pro
        115                 120                 125

Cys Thr Thr Thr Arg Asn Thr Val Cys Gln Cys Glu Glu Gly Thr Phe
130                 135                 140

Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
                165                 170                 175

Glu Cys Val His Lys Glu Ser Gly Thr Lys His Ser Gly Glu Val Pro
            180                 185                 190

Ala Val Glu Glu Thr Val Thr Ser Ser Pro Gly Thr Pro Ala Ser Pro
        195                 200                 205

Cys Ser Leu Ser Gly Ile Ile Ile Gly Val Thr Val Ala Ala Val Val
210                 215                 220

Leu Ile Val Ala Val Phe Val Cys Lys Ser Leu Leu Trp Lys Lys Val
225                 230                 235                 240

Leu Pro Tyr Leu Lys Gly Ile Cys Ser Gly Gly Gly Asp Pro Glu
                245                 250                 255

Arg Val Asp Arg Ser Ser Gln Arg Pro Gly Ala Glu Asp Asn Val Leu
            260                 265                 270

Asn Glu Ile Val Ser Ile Leu Gln Pro Thr Gln Val Pro Glu Gln Glu
        275                 280                 285

Met Glu Val Gln Glu Pro Ala Glu Pro Thr Gly Val Asn Met Leu Ser
290                 295                 300

Pro Gly Glu Ser Glu His Leu Leu Glu Pro Ala Glu Ala Glu Arg Ser
305                 310                 315                 320

Gln Arg Arg Arg Leu Leu Glu Asp Phe Leu Cys Leu Gln Thr Lys Glu
                325                 330                 335

Ile Leu Gln Lys His
            340

<210> SEQ ID NO 3
<211> LENGTH: 242
<212> TYPE: PRT
<213> ORGANISM: Artificial Sequence
<220> FEATURE:
<223> OTHER INFORMATION: Synthesized

<400> SEQUENCE: 3

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
            35                  40                  45

Tyr His Thr Ser Arg Leu His Ser Gly Val Pro Ser Arg Phe Ser Gly
        50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Gly Ser Glu Val Lys Leu Gln Glu
            115                 120                 125

Ser Gly Pro Gly Leu Val Ala Pro Ser Gln Ser Leu Ser Val Thr Cys
            130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
            195                 200                 205

Thr Asp Asp Thr Ala Ile Tyr Tyr Cys Ala Lys His Tyr Tyr Tyr Gly
            210                 215                 220

Gly Ser Tyr Ala Met Asp Tyr Trp Gly Gln Gly Thr Ser Val Thr Val
225                 230                 235                 240

Ser Ser

<210> SEQ ID NO 4
<211> LENGTH: 69
<212> TYPE: PRT
<213> ORGANISM: Artificial Sequence
<220> FEATURE:
<223> OTHER INFORMATION: Synthesized

<400> SEQUENCE: 4

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ile Tyr Ile
            35                  40                  45

Trp Ala Pro Leu Ala Gly Thr Cys Gly Val Leu Leu Leu Ser Leu Val
        50                  55                  60

Ile Thr Leu Tyr Cys
65

<210> SEQ ID NO 5
<211> LENGTH: 42
<212> TYPE: PRT
<213> ORGANISM: Homo sapiens

<400> SEQUENCE: 5

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Gly Gly Cys Glu Leu
            35                  40

<210> SEQ ID NO 6
<211> LENGTH: 112
<212> TYPE: PRT
<213> ORGANISM: Homo sapiens

<400> SEQUENCE: 6

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 7
<211> LENGTH: 531
<212> TYPE: PRT
<213> ORGANISM: Artificial Sequence
<220> FEATURE:
<223> OTHER INFORMATION: Synthesized

<400> SEQUENCE: 7

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Lys
        35                  40                  45

Tyr Ile His Pro Gln Asn Asn Ser Ile Cys Cys Thr Lys Cys His Lys
    50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

```
Asn Glu Cys Val Ser Cys Ser Asn Cys Lys Lys Ser Leu Glu Cys Thr
                180                 185                 190

Lys Leu Cys Leu Pro Gln Ile Glu Asn Val Lys Gly Thr Glu Asp Ser
            195                 200                 205

Gly Thr Thr Val Leu Leu Pro Leu Val Ile Phe Phe Gly Leu Cys Leu
        210                 215                 220

Leu Ser Leu Leu Phe Ile Gly Leu Met Tyr Arg Tyr Gln Arg Met Ala
225                 230                 235                 240

Pro Val Ala Val Trp Ala Ala Leu Ala Val Gly Leu Glu Leu Trp Ala
                245                 250                 255

Ala Ala His Ala Leu Pro Ala Gln Val Ala Phe Thr Pro Tyr Ala Pro
            260                 265                 270

Glu Pro Gly Ser Thr Cys Arg Leu Arg Glu Tyr Tyr Asp Gln Thr Ala
        275                 280                 285

Gln Met Cys Cys Ser Lys Cys Ser Pro Gly Gln His Ala Lys Val Phe
            290                 295                 300

Cys Thr Lys Thr Ser Asp Thr Val Cys Asp Ser Cys Glu Asp Ser Thr
305                 310                 315                 320

Tyr Thr Gln Leu Trp Asn Trp Val Pro Glu Cys Leu Ser Cys Gly Ser
                325                 330                 335

Arg Cys Ser Ser Asp Gln Val Glu Thr Gln Ala Cys Thr Arg Glu Gln
            340                 345                 350

Asn Arg Ile Cys Thr Cys Arg Pro Gly Trp Tyr Cys Ala Leu Ser Lys
        355                 360                 365

Gln Glu Gly Cys Arg Leu Cys Ala Pro Leu Arg Lys Cys Arg Pro Gly
            370                 375                 380

Phe Gly Val Ala Arg Pro Gly Thr Glu Thr Ser Asp Val Val Cys Lys
385                 390                 395                 400

Pro Cys Ala Pro Gly Thr Phe Ser Asn Thr Thr Ser Ser Thr Asp Ile
                405                 410                 415

Cys Arg Pro His Gln Ile Cys Asn Val Val Ala Ile Pro Gly Asn Ala
            420                 425                 430

Ser Met Asp Ala Val Cys Thr Ser Thr Ser Pro Thr Arg Ser Met Ala
        435                 440                 445

Pro Gly Ala Val His Leu Pro Gln Pro Val Ser Thr Arg Ser Gln His
            450                 455                 460

Thr Gln Pro Thr Pro Glu Pro Ser Thr Ala Pro Ser Thr Ser Phe Leu
465                 470                 475                 480

Leu Pro Met Gly Pro Ser Pro Ala Glu Gly Ser Thr Gly Asp Phe
                485                 490                 495

Ala Leu Pro Val Gly Leu Ile Val Gly Val Thr Ala Leu Gly Leu Leu
            500                 505                 510

Ile Ile Gly Val Val Asn Cys Val Ile Met Thr Gln Val Lys Lys Lys
        515                 520                 525

Pro Leu Cys
    530

<210> SEQ ID NO 8
<211> LENGTH: 1473
<212> TYPE: PRT
<213> ORGANISM: Artificial Sequence
<220> FEATURE:
<223> OTHER INFORMATION: Synthesized
```

<400> SEQUENCE: 8

```
Met Ala Gly Gly Ala Trp Gly Arg Leu Ala Cys Tyr Leu Glu Phe Leu
1               5                   10                  15

Lys Lys Glu Glu Leu Lys Glu Phe Gln Leu Leu Ala Asn Lys Ala
            20                  25                  30

His Ser Arg Ser Ser Ser Gly Glu Thr Pro Ala Gln Pro Glu Lys Thr
                35                  40                  45

Ser Gly Met Glu Val Thr Ser Tyr Leu Val Ala Gln Tyr Gly Glu Gln
    50                  55                  60

Arg Ala Trp Asp Leu Ala Leu His Thr Trp Glu Gln Met Gly Leu Arg
65                  70                  75                  80

Ser Leu Cys Ala Gln Ala Gln Glu Gly Ala Gly His Ser Pro Ser Phe
                85                  90                  95

Pro Tyr Ser Pro Ser Glu Pro His Leu Gly Ser Pro Ser Gln Pro Thr
                100                 105                 110

Ser Thr Ala Val Leu Met Pro Trp Ile His Glu Leu Pro Ala Gly Cys
                115                 120                 125

Thr Gln Gly Ser Glu Arg Arg Val Leu Arg Gln Leu Pro Asp Thr Ser
    130                 135                 140

Gly Arg Arg Trp Arg Glu Ile Ser Ala Ser Leu Leu Tyr Gln Ala Leu
145                 150                 155                 160

Pro Ser Ser Pro Asp His Glu Ser Pro Ser Gln Glu Ser Pro Asn Ala
                165                 170                 175

Pro Thr Ser Thr Ala Val Leu Gly Ser Trp Gly Ser Pro Pro Gln Pro
                180                 185                 190

Ser Leu Ala Pro Arg Glu Gln Glu Ala Pro Gly Thr Gln Trp Pro Leu
                195                 200                 205

Asp Glu Thr Ser Gly Ile Tyr Tyr Thr Glu Ile Arg Glu Arg Glu Arg
    210                 215                 220

Glu Lys Ser Glu Lys Gly Arg Pro Pro Trp Ala Ala Val Val Gly Thr
225                 230                 235                 240

Pro Pro Gln Ala His Thr Ser Leu Gln Pro His His Pro Trp Glu
                245                 250                 255

Pro Ser Val Arg Glu Ser Leu Cys Ser Thr Trp Pro Trp Lys Asn Glu
                260                 265                 270

Asp Phe Asn Gln Lys Phe Thr Gln Leu Leu Leu Gln Arg Pro His
                275                 280                 285

Pro Arg Ser Gln Asp Pro Leu Val Lys Arg Ser Trp Pro Asp Tyr Val
    290                 295                 300

Glu Glu Asn Arg Gly His Leu Ile Glu Ile Arg Asp Leu Phe Gly Pro
305                 310                 315                 320

Gly Leu Asp Thr Gln Glu Pro Arg Ile Val Ile Leu Gln Gly Ala Ala
                325                 330                 335

Gly Ile Gly Lys Ser Thr Leu Ala Arg Gln Val Lys Glu Ala Trp Gly
                340                 345                 350

Arg Gly Gln Leu Tyr Gly Asp Arg Phe Gln His Val Phe Tyr Phe Ser
                355                 360                 365

Cys Arg Glu Leu Ala Gln Ser Lys Val Val Ser Leu Ala Glu Leu Ile
    370                 375                 380

Gly Lys Asp Gly Thr Ala Thr Pro Ala Pro Ile Arg Gln Ile Leu Ser
385                 390                 395                 400
```

```
Arg Pro Glu Arg Leu Leu Phe Ile Leu Asp Gly Val Asp Glu Pro Gly
                405                 410                 415

Trp Val Leu Gln Glu Pro Ser Ser Glu Leu Cys Leu His Trp Ser Gln
            420                 425                 430

Pro Gln Pro Ala Asp Ala Leu Leu Gly Ser Leu Leu Gly Lys Thr Ile
        435                 440                 445

Leu Pro Glu Ala Ser Phe Leu Ile Thr Ala Arg Thr Thr Ala Leu Gln
    450                 455                 460

Asn Leu Ile Pro Ser Leu Glu Gln Ala Arg Trp Val Glu Val Leu Gly
465                 470                 475                 480

Phe Ser Glu Ser Ser Arg Lys Glu Tyr Phe Tyr Arg Tyr Phe Thr Asp
                485                 490                 495

Glu Arg Gln Ala Ile Arg Ala Phe Arg Leu Val Lys Ser Asn Lys Glu
            500                 505                 510

Leu Trp Ala Leu Cys Leu Val Pro Trp Val Ser Trp Leu Ala Cys Thr
        515                 520                 525

Cys Leu Met Gln Gln Met Lys Arg Lys Glu Lys Leu Thr Leu Thr Ser
    530                 535                 540

Lys Thr Thr Thr Thr Leu Cys Leu His Tyr Leu Ala Gln Ala Leu Gln
545                 550                 555                 560

Ala Gln Pro Leu Gly Pro Gln Leu Arg Asp Leu Cys Ser Leu Ala Ala
                565                 570                 575

Glu Gly Ile Trp Gln Lys Lys Thr Leu Phe Ser Pro Asp Asp Leu Arg
            580                 585                 590

Lys His Gly Leu Asp Gly Ala Ile Ile Ser Thr Phe Leu Lys Met Gly
        595                 600                 605

Ile Leu Gln Glu His Pro Ile Pro Leu Ser Tyr Ser Phe Ile His Leu
    610                 615                 620

Cys Phe Gln Glu Phe Phe Ala Ala Met Ser Tyr Val Leu Glu Asp Glu
625                 630                 635                 640

Lys Gly Arg Gly Lys His Ser Asn Cys Ile Ile Asp Leu Glu Lys Thr
                645                 650                 655

Leu Glu Ala Tyr Gly Ile His Gly Leu Phe Gly Ala Ser Thr Thr Arg
            660                 665                 670

Phe Leu Leu Gly Leu Leu Ser Asp Glu Gly Glu Arg Glu Met Glu Asn
        675                 680                 685

Ile Phe His Cys Arg Leu Ser Gln Gly Arg Asn Leu Met Gln Trp Val
    690                 695                 700

Pro Ser Leu Gln Leu Leu Leu Gln Pro His Ser Leu Glu Ser Leu His
705                 710                 715                 720

Cys Leu Tyr Glu Thr Arg Asn Lys Thr Phe Leu Thr Gln Val Met Ala
                725                 730                 735

His Phe Glu Glu Met Gly Met Cys Val Glu Thr Asp Met Glu Leu Leu
            740                 745                 750

Val Cys Thr Phe Cys Ile Lys Phe Ser Arg His Val Lys Lys Leu Gln
        755                 760                 765

Leu Ile Glu Gly Arg Gln His Arg Ser Thr Trp Ser Pro Thr Met Val
    770                 775                 780

Val Leu Phe Arg Trp Val Pro Val Thr Asp Ala Tyr Trp Gln Ile Leu
785                 790                 795                 800

Phe Ser Val Leu Lys Val Thr Arg Asn Leu Lys Glu Leu Asp Leu Ser
                805                 810                 815
```

-continued

Gly Asn Ser Leu Ser His Ser Ala Val Lys Ser Leu Cys Lys Thr Leu
              820                 825                 830

Arg Arg Pro Arg Cys Leu Leu Glu Thr Leu Arg Leu Ala Gly Cys Gly
              835                 840                 845

Leu Thr Ala Glu Asp Cys Lys Asp Leu Ala Phe Gly Leu Arg Ala Asn
              850                 855                 860

Gln Thr Leu Thr Glu Leu Asp Leu Ser Phe Asn Val Leu Thr Asp Ala
865                 870                 875                 880

Gly Ala Lys His Leu Cys Gln Arg Leu Arg Gln Pro Ser Cys Lys Leu
              885                 890                 895

Gln Arg Leu Gln Leu Val Ser Cys Gly Leu Thr Ser Asp Cys Cys Gln
              900                 905                 910

Asp Leu Ala Ser Val Leu Ser Ala Ser Pro Ser Leu Lys Glu Leu Asp
              915                 920                 925

Leu Gln Gln Asn Asn Leu Asp Asp Val Gly Val Arg Leu Leu Cys Glu
              930                 935                 940

Gly Leu Arg His Pro Ala Cys Lys Leu Ile Arg Leu Gly Leu Asp Gln
945                 950                 955                 960

Thr Thr Leu Ser Asp Glu Met Arg Gln Glu Leu Arg Ala Leu Glu Gln
              965                 970                 975

Glu Lys Pro Gln Leu Leu Ile Phe Ser Arg Arg Lys Pro Ser Val Met
              980                 985                 990

Thr Pro Thr Glu Gly Leu Asp Thr Gly Glu Met Ser Asn Ser Thr Ser
              995                 1000                1005

Ser Leu Lys Arg Gln Arg Leu Gly Ser Glu Arg Ala Ala Ser His
              1010                1015                1020

Val Ala Gln Ala Asn Leu Lys Leu Leu Asp Val Ser Lys Ile Phe
              1025                1030                1035

Pro Ile Ala Glu Ile Ala Glu Glu Ser Ser Pro Glu Val Val Pro
              1040                1045                1050

Val Glu Leu Leu Cys Val Pro Ser Pro Ala Ser Gln Gly Asp Leu
              1055                1060                1065

His Thr Lys Pro Leu Gly Thr Asp Asp Asp Phe Trp Gly Pro Thr
              1070                1075                1080

Gly Pro Val Ala Thr Glu Val Val Asp Lys Glu Lys Asn Leu Tyr
              1085                1090                1095

Arg Val His Phe Pro Val Ala Gly Ser Tyr Arg Trp Pro Asn Thr
              1100                1105                1110

Gly Leu Cys Phe Val Met Arg Glu Ala Val Thr Val Glu Ile Glu
              1115                1120                1125

Phe Cys Val Trp Asp Gln Phe Leu Gly Glu Ile Asn Pro Gln His
              1130                1135                1140

Ser Trp Met Val Ala Gly Pro Leu Leu Asp Ile Lys Ala Glu Pro
              1145                1150                1155

Gly Ala Val Glu Ala Val His Leu Pro His Phe Val Ala Leu Gln
              1160                1165                1170

Gly Gly His Val Asp Thr Ser Leu Phe Gln Met Ala His Phe Lys
              1175                1180                1185

Glu Glu Gly Met Leu Leu Glu Lys Pro Ala Arg Val Glu Leu His
              1190                1195                1200

His Ile Val Leu Glu Asn Pro Ser Phe Ser Pro Leu Gly Val Leu
              1205                1210                1215

Leu Lys Met Ile His Asn Ala Leu Arg Phe Ile Pro Val Thr Ser
    1220                1225                1230

Val Val Leu Leu Tyr His Arg Val His Pro Glu Glu Val Thr Phe
    1235                1240                1245

His Leu Tyr Leu Ile Pro Ser Asp Cys Ser Ile Arg Lys Ala Ile
    1250                1255                1260

Asp Asp Leu Glu Met Lys Phe Gln Phe Val Arg Ile His Lys Pro
    1265                1270                1275

Pro Pro Leu Thr Pro Leu Tyr Met Gly Cys Arg Tyr Thr Val Ser
    1280                1285                1290

Gly Ser Gly Ser Gly Met Leu Glu Ile Leu Pro Lys Glu Leu Glu
    1295                1300                1305

Leu Cys Tyr Arg Ser Pro Gly Glu Asp Gln Leu Phe Ser Glu Phe
    1310                1315                1320

Tyr Val Gly His Leu Gly Ser Gly Ile Arg Leu Gln Val Lys Asp
    1325                1330                1335

Lys Lys Asp Glu Thr Leu Val Trp Glu Ala Leu Val Lys Pro Gly
    1340                1345                1350

Asp Leu Met Pro Ala Thr Thr Leu Ile Pro Pro Ala Arg Ile Ala
    1355                1360                1365

Val Pro Ser Pro Leu Asp Ala Pro Gln Leu Leu His Phe Val Asp
    1370                1375                1380

Gln Tyr Arg Glu Gln Leu Ile Ala Arg Val Thr Ser Val Glu Val
    1385                1390                1395

Val Leu Asp Lys Leu His Gly Gln Val Leu Ser Gln Glu Gln Tyr
    1400                1405                1410

Glu Arg Val Leu Ala Glu Asn Thr Arg Pro Ser Gln Met Arg Lys
    1415                1420                1425

Leu Phe Ser Leu Ser Gln Ser Trp Asp Arg Lys Cys Lys Asp Gly
    1430                1435                1440

Leu Tyr Gln Ala Leu Lys Glu Thr His Pro His Leu Ile Met Glu
    1445                1450                1455

Leu Trp Glu Lys Gly Ser Lys Lys Gly Leu Leu Pro Leu Ser Ser
    1460                1465                1470

<210> SEQ ID NO 9
<211> LENGTH: 1473
<212> TYPE: PRT
<213> ORGANISM: Artificial Sequence
<220> FEATURE:
<223> OTHER INFORMATION: Synthesized

<400> SEQUENCE: 9

Met Ala Gly Gly Ala Trp Gly Arg Leu Ala Cys Tyr Leu Glu Phe Leu
1               5                   10                  15

Lys Lys Glu Glu Leu Lys Glu Phe Gln Leu Leu Leu Ala Asn Lys Ala
                20                  25                  30

His Ser Arg Ser Ser Ser Gly Glu Thr Pro Ala Gln Pro Glu Lys Thr
            35                  40                  45

Ser Gly Met Glu Val Ala Ser Tyr Leu Val Ala Gln Tyr Gly Glu Gln
        50                  55                  60

Arg Val Trp Asp Leu Ala Leu His Thr Trp Glu Gln Met Gly Leu Arg
65                  70                  75                  80

Ser Leu Cys Ala Gln Ala Gln Glu Gly Ala Gly His Ser Pro Ser Phe
                85                  90                  95

-continued

```
Pro Tyr Ser Pro Ser Glu Pro His Leu Gly Ser Pro Ser Gln Pro Thr
            100                 105                 110
Ser Thr Ala Val Leu Met Pro Trp Ile His Glu Leu Pro Ala Gly Cys
        115                 120                 125
Thr Gln Gly Ser Glu Arg Arg Val Leu Arg Gln Leu Pro Asp Thr Ser
    130                 135                 140
Gly Arg Arg Trp Arg Glu Ile Ser Ala Ser Leu Leu Tyr Gln Ala Leu
145                 150                 155                 160
Pro Ser Ser Pro Asp His Glu Ser Pro Ser Gln Ser Pro Asn Ala
                165                 170                 175
Pro Thr Ser Thr Ala Val Leu Gly Ser Trp Ser Pro Pro Gln Pro
            180                 185                 190
Ser Leu Ala Pro Arg Glu Gln Glu Ala Pro Gly Thr Gln Trp Pro Leu
        195                 200                 205
Asp Glu Thr Ser Gly Ile Tyr Tyr Thr Glu Ile Arg Glu Arg Glu Arg
    210                 215                 220
Glu Lys Ser Glu Lys Gly Arg Pro Pro Trp Ala Ala Val Val Gly Thr
225                 230                 235                 240
Pro Pro Gln Ala His Thr Ser Leu Gln Pro His His His Pro Trp Glu
                245                 250                 255
Pro Ser Val Arg Glu Ser Leu Cys Ser Thr Trp Pro Trp Lys Asn Glu
            260                 265                 270
Asp Phe Asn Gln Lys Phe Thr Gln Leu Leu Leu Leu Gln Arg Pro His
        275                 280                 285
Pro Arg Ser Gln Asp Pro Leu Val Lys Arg Ser Trp Pro Asp Tyr Val
    290                 295                 300
Glu Glu Asn Arg Gly His Leu Ile Glu Ile Arg Asp Leu Phe Gly Pro
305                 310                 315                 320
Gly Leu Asp Thr Gln Glu Pro Arg Ile Val Ile Leu Gln Gly Ala Ala
                325                 330                 335
Gly Ile Gly Lys Ser Thr Leu Ala Arg Gln Val Lys Glu Ala Trp Gly
            340                 345                 350
Arg Gly Gln Leu Tyr Gly Asp Arg Phe Gln His Val Phe Tyr Phe Ser
        355                 360                 365
Cys Arg Glu Leu Ala Gln Ser Lys Val Val Ser Leu Ala Glu Leu Ile
    370                 375                 380
Gly Lys Asp Gly Thr Ala Thr Pro Ala Pro Ile Arg Gln Ile Leu Ser
385                 390                 395                 400
Arg Pro Glu Arg Leu Leu Phe Ile Leu Asp Gly Val Asp Glu Pro Gly
                405                 410                 415
Trp Val Leu Gln Glu Pro Ser Ser Glu Leu Cys Leu His Trp Ser Gln
            420                 425                 430
Pro Gln Pro Ala Asp Ala Leu Leu Gly Ser Leu Leu Gly Lys Thr Ile
        435                 440                 445
Leu Pro Glu Ala Ser Phe Leu Ile Thr Ala Arg Thr Thr Ala Leu Gln
    450                 455                 460
Asn Leu Ile Pro Ser Leu Glu Gln Ala Arg Trp Val Glu Val Leu Gly
465                 470                 475                 480
Phe Ser Glu Ser Ser Arg Lys Glu Tyr Phe Arg Tyr Phe Thr Asp
                485                 490                 495
Glu Arg Gln Ala Ile Arg Ala Phe Arg Leu Val Lys Ser Asn Lys Glu
            500                 505                 510
```

```
Leu Trp Ala Leu Cys Leu Val Pro Trp Val Ser Trp Leu Ala Cys Thr
        515                 520                 525

Cys Leu Met Gln Gln Met Lys Arg Lys Glu Lys Leu Thr Leu Thr Ser
530                 535                 540

Lys Thr Thr Thr Thr Leu Cys Leu His Tyr Leu Ala Gln Ala Leu Gln
545                 550                 555                 560

Ala Gln Pro Leu Gly Pro Gln Leu Arg Asp Leu Cys Ser Leu Ala Ala
                565                 570                 575

Glu Gly Ile Trp Gln Lys Lys Thr Leu Phe Ser Pro Asp Asp Leu Arg
                580                 585                 590

Lys His Gly Leu Asp Gly Ala Ile Ile Ser Thr Phe Leu Lys Met Gly
        595                 600                 605

Ile Leu Gln Glu His Pro Ile Pro Leu Ser Tyr Ser Phe Ile His Leu
        610                 615                 620

Cys Phe Gln Glu Phe Phe Ala Ala Met Ser Tyr Val Leu Glu Asp Glu
625                 630                 635                 640

Lys Gly Arg Gly Lys His Ser Asn Cys Ile Ile Asp Leu Glu Lys Thr
                645                 650                 655

Leu Glu Ala Tyr Gly Ile His Gly Leu Phe Gly Ala Ser Thr Thr Arg
                660                 665                 670

Phe Leu Leu Gly Leu Leu Ser Asp Glu Gly Glu Arg Glu Met Glu Asn
675                 680                 685

Ile Phe His Cys Arg Leu Ser Gln Gly Arg Asn Leu Met Gln Trp Val
        690                 695                 700

Pro Ser Leu Gln Leu Leu Leu Gln Pro His Ser Leu Glu Ser Leu His
705                 710                 715                 720

Cys Leu Tyr Glu Thr Arg Asn Lys Thr Phe Leu Thr Gln Val Met Ala
                725                 730                 735

His Phe Glu Glu Met Gly Met Cys Val Glu Thr Asp Met Glu Leu Leu
                740                 745                 750

Val Cys Thr Phe Cys Ile Lys Phe Ser Arg His Val Lys Lys Leu Gln
        755                 760                 765

Leu Ile Glu Gly Arg Gln His Arg Ser Thr Trp Ser Pro Thr Met Val
770                 775                 780

Val Leu Phe Arg Trp Val Pro Val Thr Asp Ala Tyr Trp Gln Ile Leu
785                 790                 795                 800

Phe Ser Val Leu Lys Val Thr Arg Asn Leu Lys Glu Leu Asp Leu Ser
                805                 810                 815

Gly Asn Ser Leu Ser His Ser Ala Val Lys Ser Leu Cys Lys Thr Leu
                820                 825                 830

Arg Arg Pro Arg Cys Leu Leu Glu Thr Leu Arg Leu Ala Gly Cys Gly
        835                 840                 845

Leu Thr Ala Glu Asp Cys Lys Asp Leu Ala Phe Gly Leu Arg Ala Asn
        850                 855                 860

Gln Thr Leu Thr Glu Leu Asp Leu Ser Phe Asn Val Leu Thr Asp Ala
865                 870                 875                 880

Gly Ala Lys His Leu Cys Gln Arg Leu Arg Gln Pro Ser Cys Lys Leu
                885                 890                 895

Gln Arg Leu Gln Leu Val Ser Cys Gly Leu Thr Ser Asp Cys Cys Gln
                900                 905                 910

Asp Leu Ala Ser Val Leu Ser Ala Ser Pro Ser Leu Lys Glu Leu Asp
        915                 920                 925
```

-continued

```
Leu Gln Gln Asn Asn Leu Asp Asp Val Gly Val Arg Leu Leu Cys Glu
            930                 935                 940
Gly Leu Arg His Pro Ala Cys Lys Leu Ile Arg Leu Gly Leu Asp Gln
945                 950                 955                 960
Thr Thr Leu Ser Asp Glu Met Arg Gln Glu Leu Arg Ala Leu Glu Gln
                965                 970                 975
Glu Lys Pro Gln Leu Leu Ile Phe Ser Arg Arg Lys Pro Ser Val Met
            980                 985                 990
Thr Pro Thr Glu Gly Leu Asp Thr Gly Glu Met Ser Asn Ser Thr Ser
        995                 1000                1005
Ser Leu Lys Arg Gln Arg Leu Gly Ser Glu Arg Ala Ala Ser His
    1010                1015                1020
Val Ala Gln Ala Asn Leu Lys Leu Leu Asp Val Ser Lys Ile Phe
    1025                1030                1035
Pro Ile Ala Glu Ile Ala Glu Glu Ser Ser Pro Glu Val Val Pro
    1040                1045                1050
Val Glu Leu Leu Cys Val Pro Ser Pro Ala Ser Gln Gly Asp Leu
    1055                1060                1065
His Thr Lys Pro Leu Gly Thr Asp Asp Asp Phe Trp Gly Pro Thr
    1070                1075                1080
Gly Pro Val Ala Thr Glu Val Val Asp Lys Glu Lys Asn Leu Tyr
    1085                1090                1095
Arg Val His Phe Pro Val Ala Gly Ser Tyr Arg Trp Pro Asn Thr
    1100                1105                1110
Gly Leu Cys Phe Val Met Arg Glu Ala Val Thr Val Glu Ile Glu
    1115                1120                1125
Phe Cys Val Trp Asp Gln Phe Leu Gly Glu Ile Asn Pro Gln His
    1130                1135                1140
Ser Trp Met Val Ala Gly Pro Leu Leu Asp Ile Lys Ala Glu Pro
    1145                1150                1155
Gly Ala Val Glu Ala Val His Leu Pro His Phe Val Ala Leu Gln
    1160                1165                1170
Gly Gly His Val Asp Thr Ser Leu Phe Gln Met Ala His Phe Lys
    1175                1180                1185
Glu Glu Gly Met Leu Leu Glu Lys Pro Ala Arg Val Glu Leu His
    1190                1195                1200
His Ile Val Leu Glu Asn Pro Ser Phe Ser Pro Leu Gly Val Leu
    1205                1210                1215
Leu Lys Met Ile His Asn Ala Leu Arg Phe Ile Pro Val Thr Ser
    1220                1225                1230
Val Val Leu Leu Tyr His Arg Val His Pro Glu Glu Val Thr Phe
    1235                1240                1245
His Leu Tyr Leu Ile Pro Ser Asp Cys Ser Ile Arg Lys Ala Ile
    1250                1255                1260
Asp Asp Leu Glu Met Lys Phe Gln Phe Val Arg Ile His Lys Pro
    1265                1270                1275
Pro Pro Leu Thr Pro Leu Tyr Met Gly Cys Arg Tyr Thr Val Ser
    1280                1285                1290
Gly Ser Gly Ser Gly Met Leu Glu Ile Leu Pro Lys Glu Leu Glu
    1295                1300                1305
Leu Cys Tyr Arg Ser Pro Gly Glu Asp Gln Leu Phe Ser Glu Phe
    1310                1315                1320
```

```
Tyr Val Gly His Leu Gly Ser Gly Ile Arg Leu Gln Val Lys Asp
    1325                1330                1335

Lys Lys Asp Glu Thr Leu Val Trp Glu Ala Leu Val Lys Pro Gly
    1340                1345                1350

Asp Leu Met Pro Ala Thr Thr Leu Ile Pro Pro Ala Arg Ile Ala
    1355                1360                1365

Val Pro Ser Pro Leu Asp Ala Pro Gln Leu Leu His Phe Val Asp
    1370                1375                1380

Gln Tyr Arg Glu Gln Leu Ile Ala Arg Val Thr Ser Val Glu Val
    1385                1390                1395

Val Leu Asp Lys Leu His Gly Gln Val Leu Ser Gln Glu Gln Tyr
    1400                1405                1410

Glu Arg Val Leu Ala Glu Asn Thr Arg Pro Ser Gln Met Arg Lys
    1415                1420                1425

Leu Phe Ser Leu Ser Gln Ser Trp Asp Arg Lys Cys Lys Asp Gly
    1430                1435                1440

Leu Tyr Gln Ala Leu Lys Glu Thr His Pro His Leu Ile Met Glu
    1445                1450                1455

Leu Trp Glu Lys Gly Ser Lys Lys Gly Leu Leu Pro Leu Ser Ser
    1460                1465                1470

<210> SEQ ID NO 10
<211> LENGTH: 1473
<212> TYPE: PRT
<213> ORGANISM: Artificial Sequence
<220> FEATURE:
<223> OTHER INFORMATION: Synthesized

<400> SEQUENCE: 10

Met Ala Gly Gly Ala Trp Gly Arg Leu Ala Cys Tyr Leu Glu Phe Leu
1               5                   10                  15

Lys Lys Glu Glu Leu Lys Glu Phe Gln Leu Leu Leu Ala Asn Lys Ala
                20                  25                  30

His Ser Arg Ser Ser Ser Gly Glu Thr Pro Ala Gln Pro Glu Lys Thr
            35                  40                  45

Ser Gly Met Glu Val Ala Ser Tyr Leu Val Ala Gln Tyr Gly Glu Gln
        50                  55                  60

Arg Ala Trp Asp Leu Ala Leu His Thr Trp Glu Gln Met Gly Leu Arg
65                  70                  75                  80

Ser Leu Cys Ala Gln Ala Gln Glu Gly Ala Gly His Ser Pro Ser Phe
                85                  90                  95

Pro Tyr Ser Pro Ser Glu Pro His Leu Gly Ser Pro Ser Gln Pro Thr
            100                 105                 110

Ser Thr Ala Val Leu Met Pro Trp Ile His Glu Leu Pro Ala Gly Cys
        115                 120                 125

Thr Gln Gly Ser Glu Arg Arg Val Leu Arg Gln Leu Pro Asp Thr Ser
    130                 135                 140

Gly Arg Arg Trp Arg Glu Ile Ser Ala Ser Leu Leu Tyr Gln Ala Leu
145                 150                 155                 160

Pro Ser Ser Pro Asp His Glu Ser Pro Ser Gln Glu Ser Pro Asn Ala
                165                 170                 175

Pro Thr Ser Thr Ala Val Leu Gly Ser Trp Gly Ser Pro Pro Gln Pro
            180                 185                 190

Ser Leu Ala Pro Arg Glu Gln Glu Ala Pro Gly Thr Gln Trp Pro Leu
        195                 200                 205
```

-continued

```
Asp Glu Thr Ser Gly Ile Tyr Tyr Thr Glu Ile Arg Glu Arg Glu Arg
    210                 215                 220

Glu Lys Ser Glu Lys Gly Arg Pro Pro Trp Ala Ala Val Val Gly Thr
225                 230                 235                 240

Pro Pro Gln Ala His Thr Ser Leu Gln Pro His His His Pro Trp Glu
                245                 250                 255

Pro Ser Val Arg Glu Ser Leu Cys Ser Thr Trp Pro Trp Lys Asn Glu
                260                 265                 270

Asp Phe Asn Gln Lys Phe Thr Gln Leu Leu Leu Gln Arg Pro His
                275                 280                 285

Pro Arg Ser Gln Asp Pro Leu Val Lys Arg Ser Trp Pro Asp Tyr Val
290                 295                 300

Glu Glu Asn Arg Gly His Leu Ile Glu Ile Arg Asp Leu Phe Gly Pro
305                 310                 315                 320

Gly Leu Asp Thr Gln Glu Pro Arg Ile Val Ile Leu Gln Gly Ala Ala
                325                 330                 335

Gly Ile Gly Lys Ser Thr Leu Ala Arg Gln Val Lys Glu Ala Trp Gly
                340                 345                 350

Arg Gly Gln Leu Tyr Gly Asp Arg Phe Gln His Val Phe Tyr Phe Ser
                355                 360                 365

Cys Arg Glu Leu Ala Gln Ser Lys Val Val Ser Leu Ala Glu Leu Ile
    370                 375                 380

Gly Lys Asp Gly Thr Ala Thr Pro Ala Pro Ile Arg Gln Ile Leu Ser
385                 390                 395                 400

Arg Pro Glu Arg Leu Leu Phe Ile Leu Asp Gly Val Asp Glu Pro Gly
                405                 410                 415

Trp Val Leu Gln Glu Pro Ser Ser Glu Leu Cys Leu His Trp Ser Gln
                420                 425                 430

Pro Gln Pro Ala Asp Ala Leu Leu Gly Ser Leu Leu Gly Lys Thr Ile
                435                 440                 445

Leu Pro Glu Ala Ser Phe Leu Ile Thr Ala Arg Thr Thr Ala Leu Gln
    450                 455                 460

Asn Leu Ile Pro Ser Leu Glu Gln Ala Arg Trp Val Glu Val Leu Gly
465                 470                 475                 480

Phe Ser Glu Ser Ser Arg Lys Glu Tyr Phe Tyr Arg Tyr Phe Thr Asp
                485                 490                 495

Glu Arg Gln Ala Ile Arg Ala Phe Arg Leu Val Lys Ser Asn Lys Glu
                500                 505                 510

Leu Trp Ala Leu Cys Leu Val Pro Trp Val Ser Trp Leu Ala Cys Thr
    515                 520                 525

Cys Leu Met Gln Gln Met Lys Arg Lys Glu Lys Leu Thr Leu Thr Ser
    530                 535                 540

Lys Thr Thr Thr Thr Leu Cys Leu His Tyr Leu Ala Gln Ala Leu Gln
545                 550                 555                 560

Ala Gln Pro Leu Gly Pro Gln Leu Arg Asp Leu Cys Ser Leu Ala Ala
                565                 570                 575

Glu Gly Ile Trp Gln Lys Lys Thr Leu Phe Ser Pro Asp Asp Leu Arg
                580                 585                 590

Lys His Gly Leu Asp Gly Ala Ile Ile Ser Thr Phe Leu Lys Met Gly
    595                 600                 605

Ile Leu Gln Glu His Pro Ile Pro Leu Ser Tyr Ser Phe Ile His Leu
    610                 615                 620
```

```
Cys Phe Gln Glu Phe Phe Ala Met Ser Tyr Val Leu Glu Asp Glu
625                 630                 635                 640

Lys Gly Arg Gly Lys His Ser Asn Cys Ile Ile Asp Leu Glu Lys Thr
            645                 650                 655

Leu Glu Ala Tyr Gly Ile His Gly Leu Phe Gly Ala Ser Thr Thr Arg
            660                 665                 670

Phe Leu Leu Gly Leu Leu Ser Asp Glu Gly Glu Arg Glu Met Glu Asn
            675                 680                 685

Ile Phe His Cys Arg Leu Ser Gln Gly Arg Asn Leu Met Gln Trp Val
690                 695                 700

Pro Ser Leu Gln Leu Leu Gln Pro His Ser Leu Glu Ser Leu His
705                 710                 715                 720

Cys Leu Tyr Glu Thr Arg Asn Lys Thr Phe Leu Thr Gln Val Met Ala
                725                 730                 735

His Phe Glu Glu Met Gly Met Cys Val Glu Thr Asp Met Glu Leu Leu
                740                 745                 750

Val Cys Thr Phe Cys Ile Lys Phe Ser Arg His Val Lys Lys Leu Gln
                755                 760                 765

Leu Ile Glu Gly Arg Gln His Arg Ser Thr Trp Ser Pro Thr Met Val
770                 775                 780

Val Leu Phe Arg Trp Val Pro Val Thr Asp Ala Tyr Trp Gln Ile Leu
785                 790                 795                 800

Phe Ser Val Leu Lys Val Thr Arg Asn Leu Lys Glu Leu Asp Leu Ser
                805                 810                 815

Gly Asn Ser Leu Ser His Ser Ala Val Lys Ser Leu Cys Lys Thr Leu
                820                 825                 830

Arg Arg Pro Arg Cys Leu Leu Glu Thr Leu Arg Leu Ala Gly Cys Gly
            835                 840                 845

Leu Thr Ala Glu Asp Cys Lys Asp Leu Ala Phe Gly Leu Arg Ala Asn
850                 855                 860

Gln Thr Leu Thr Glu Leu Asp Leu Ser Phe Asn Val Leu Thr Asp Ala
865                 870                 875                 880

Gly Ala Lys His Leu Cys Gln Arg Leu Arg Gln Pro Ser Cys Lys Leu
            885                 890                 895

Gln Arg Leu Gln Leu Val Ser Cys Gly Leu Thr Ser Asp Cys Cys Gln
            900                 905                 910

Asp Leu Ala Ser Val Leu Ser Ala Ser Pro Ser Leu Lys Glu Leu Asp
            915                 920                 925

Leu Gln Gln Asn Asn Leu Asp Asp Val Gly Val Arg Leu Leu Cys Glu
            930                 935                 940

Gly Leu Arg His Pro Ala Cys Lys Leu Ile Arg Leu Gly Leu Asp Gln
945                 950                 955                 960

Thr Thr Leu Ser Asp Glu Met Arg Gln Glu Leu Arg Ala Leu Glu Gln
                965                 970                 975

Glu Lys Pro Gln Leu Leu Ile Phe Ser Arg Arg Lys Pro Ser Val Met
            980                 985                 990

Thr Pro Thr Glu Gly Leu Asp Thr Gly Glu Met Ser Asn Ser Thr Ser
            995                 1000                1005

Ser Leu Lys Arg Gln Arg Leu Gly Ser Glu Arg Ala Ala Ser His
    1010                1015                1020

Val Ala Gln Ala Asn Leu Lys Leu Leu Asp Val Ser Lys Ile Phe
    1025                1030                1035
```

-continued

Pro Ile Ala Glu Ile Ala Glu Glu Ser Ser Pro Glu Val Val Pro
    1040                1045                1050

Val Glu Leu Leu Cys Val Pro Ser Pro Ala Ser Gln Gly Asp Leu
    1055                1060                1065

His Thr Lys Pro Leu Gly Thr Asp Asp Asp Phe Trp Gly Pro Thr
    1070                1075                1080

Gly Pro Val Ala Thr Glu Val Val Asp Lys Glu Lys Asn Leu Tyr
    1085                1090                1095

Arg Val His Phe Pro Val Ala Gly Ser Tyr Arg Trp Pro Asn Thr
    1100                1105                1110

Gly Leu Cys Phe Val Met Arg Glu Ala Val Thr Val Glu Ile Glu
    1115                1120                1125

Phe Cys Val Trp Asp Gln Phe Leu Gly Glu Ile Asn Pro Gln His
    1130                1135                1140

Ser Trp Met Val Ala Gly Pro Leu Leu Asp Ile Lys Ala Glu Pro
    1145                1150                1155

Gly Ala Val Glu Ala Val His Leu Pro His Phe Val Ala Leu Gln
    1160                1165                1170

Gly Gly His Val Asp Thr Ser Leu Phe Gln Val Ala His Phe Lys
    1175                1180                1185

Glu Glu Gly Met Leu Leu Glu Lys Pro Ala Arg Val Glu Leu His
    1190                1195                1200

His Ile Val Leu Glu Asn Pro Ser Phe Ser Pro Leu Gly Val Leu
    1205                1210                1215

Leu Lys Met Ile His Asn Ala Leu Arg Phe Ile Pro Val Thr Ser
    1220                1225                1230

Val Val Leu Leu Tyr His Arg Val His Pro Glu Glu Val Thr Phe
    1235                1240                1245

His Leu Tyr Leu Ile Pro Ser Asp Cys Ser Ile Arg Lys Ala Ile
    1250                1255                1260

Asp Asp Leu Glu Met Lys Phe Gln Phe Val Arg Ile His Lys Pro
    1265                1270                1275

Pro Pro Leu Thr Pro Leu Tyr Met Gly Cys Arg Tyr Thr Val Ser
    1280                1285                1290

Gly Ser Gly Ser Gly Met Leu Glu Ile Leu Pro Lys Glu Leu Glu
    1295                1300                1305

Leu Cys Tyr Arg Ser Pro Gly Glu Asp Gln Leu Phe Ser Glu Phe
    1310                1315                1320

Tyr Val Gly His Leu Gly Ser Gly Ile Arg Leu Gln Val Lys Asp
    1325                1330                1335

Lys Lys Asp Glu Thr Leu Val Trp Glu Ala Leu Val Lys Pro Gly
    1340                1345                1350

Asp Leu Met Pro Ala Thr Thr Leu Ile Pro Pro Ala Arg Ile Ala
    1355                1360                1365

Val Pro Ser Pro Leu Asp Ala Pro Gln Leu Leu His Phe Val Asp
    1370                1375                1380

Gln Tyr Arg Glu Gln Leu Ile Ala Arg Val Thr Ser Val Glu Val
    1385                1390                1395

Val Leu Asp Lys Leu His Gly Gln Val Leu Ser Gln Glu Gln Tyr
    1400                1405                1410

Glu Arg Val Leu Ala Glu Asn Thr Arg Pro Ser Gln Met Arg Lys
    1415                1420                1425

Leu Phe Ser Leu Ser Gln Ser Trp Asp Arg Lys Cys Lys Asp Gly
        1430                1435                1440

Leu Tyr Gln Ala Leu Lys Glu Thr His Pro His Leu Ile Met Glu
        1445                1450                1455

Leu Trp Glu Lys Gly Ser Lys Gly Leu Leu Pro Leu Ser Ser
        1460                1465                1470

<210> SEQ ID NO 11
<211> LENGTH: 1203
<212> TYPE: PRT
<213> ORGANISM: Artificial Sequence
<220> FEATURE:
<223> OTHER INFORMATION: Synthesized

<400> SEQUENCE: 11

Met Ala Gly Gly Ala Trp Gly Arg Leu Ala Cys Tyr Leu Glu Phe Leu
1               5                   10                  15

Lys Lys Glu Glu Leu Lys Glu Phe Gln Leu Leu Leu Ala Asn Lys Ala
            20                  25                  30

His Ser Arg Ser Ser Ser Gly Glu Thr Pro Ala Gln Pro Glu Lys Thr
        35                  40                  45

Ser Gly Met Glu Val Ala Ser Tyr Leu Val Ala Gln Tyr Gly Glu Gln
    50                  55                  60

Arg Ala Trp Asp Leu Ala Leu His Thr Trp Glu Gln Met Gly Leu Arg
65                  70                  75                  80

Ser Leu Cys Ala Gln Ala Gln Glu Gly Ala Gly His Ser Pro Ser Phe
                85                  90                  95

Pro Tyr Ser Pro Ser Glu Pro His Leu Gly Ser Pro Ser Gln Pro Thr
            100                 105                 110

Ser Thr Ala Val Leu Met Pro Trp Ile His Glu Leu Pro Ala Gly Cys
        115                 120                 125

Thr Gln Gly Ser Glu Arg Arg Val Leu Arg Gln Leu Pro Asp Thr Ser
    130                 135                 140

Gly Arg Arg Trp Arg Glu Ile Ser Ala Ser Leu Leu Tyr Gln Ala Leu
145                 150                 155                 160

Pro Ser Ser Pro Asp His Glu Ser Pro Ser Gln Glu Ser Pro Asn Ala
                165                 170                 175

Pro Thr Ser Thr Ala Val Leu Gly Ser Trp Gly Ser Pro Pro Gln Pro
            180                 185                 190

Ser Leu Ala Pro Arg Glu Gln Glu Ala Pro Gly Thr Gln Trp Pro Leu
        195                 200                 205

Asp Glu Thr Ser Gly Ile Tyr Tyr Thr Glu Ile Arg Glu Arg Glu Arg
    210                 215                 220

Glu Lys Ser Glu Lys Gly Arg Pro Pro Trp Ala Ala Val Val Gly Thr
225                 230                 235                 240

Pro Pro Gln Ala His Thr Ser Leu Gln Pro His His His Pro Trp Glu
                245                 250                 255

Pro Ser Val Arg Glu Ser Leu Cys Ser Thr Trp Pro Trp Lys Asn Glu
            260                 265                 270

Asp Phe Asn Gln Lys Phe Thr Gln Leu Leu Leu Leu Gln Arg Pro His
        275                 280                 285

Pro Arg Ser Gln Asp Pro Leu Val Lys Arg Ser Trp Pro Asp Tyr Val
    290                 295                 300

Glu Glu Asn Arg Gly His Leu Ile Glu Ile Arg Asp Leu Phe Gly Pro
305                 310                 315                 320

```
Gly Leu Asp Thr Gln Glu Pro Arg Ile Val Ile Leu Gln Gly Ala Ala
                325                 330                 335

Gly Ile Gly Lys Ser Thr Leu Ala Arg Gln Val Lys Glu Ala Trp Gly
            340                 345                 350

Arg Gly Gln Leu Tyr Gly Asp Arg Phe Gln His Val Phe Tyr Phe Ser
                355                 360                 365

Cys Arg Glu Leu Ala Gln Ser Lys Val Val Ser Leu Ala Glu Leu Ile
        370                 375                 380

Gly Lys Asp Gly Thr Ala Thr Pro Ala Pro Ile Arg Gln Ile Leu Ser
385                 390                 395                 400

Arg Pro Glu Arg Leu Leu Phe Ile Leu Asp Gly Val Asp Glu Pro Gly
                405                 410                 415

Trp Val Leu Gln Glu Pro Ser Ser Glu Leu Cys Leu His Trp Ser Gln
                420                 425                 430

Pro Gln Pro Ala Asp Ala Leu Leu Gly Ser Leu Leu Gly Lys Thr Ile
        435                 440                 445

Leu Pro Glu Ala Ser Phe Leu Ile Thr Ala Arg Thr Thr Ala Leu Gln
        450                 455                 460

Asn Leu Ile Pro Ser Leu Glu Gln Ala Arg Trp Val Glu Val Leu Gly
465                 470                 475                 480

Phe Ser Glu Ser Ser Arg Lys Glu Tyr Phe Tyr Arg Tyr Phe Thr Asp
                485                 490                 495

Glu Arg Gln Ala Ile Arg Ala Phe Arg Leu Val Lys Ser Asn Lys Glu
        500                 505                 510

Leu Trp Ala Leu Cys Leu Val Pro Trp Val Ser Trp Leu Ala Cys Thr
        515                 520                 525

Cys Leu Met Gln Gln Met Lys Arg Lys Glu Lys Leu Thr Leu Thr Ser
        530                 535                 540

Lys Thr Thr Thr Thr Leu Cys Leu His Tyr Leu Ala Gln Ala Leu Gln
545                 550                 555                 560

Ala Gln Pro Leu Gly Pro Gln Leu Arg Asp Leu Cys Ser Leu Ala Ala
                565                 570                 575

Glu Gly Ile Trp Gln Lys Lys Thr Leu Phe Ser Pro Asp Asp Leu Arg
                580                 585                 590

Lys His Gly Leu Asp Gly Ala Ile Ile Ser Thr Phe Leu Lys Met Gly
        595                 600                 605

Ile Leu Gln Glu His Pro Ile Pro Leu Ser Tyr Ser Phe Ile His Leu
        610                 615                 620

Cys Phe Gln Glu Phe Phe Ala Ala Met Ser Tyr Val Leu Glu Asp Glu
625                 630                 635                 640

Lys Gly Arg Gly Lys His Ser Asn Cys Ile Ile Asp Leu Glu Lys Thr
                645                 650                 655

Leu Glu Ala Tyr Gly Ile His Gly Leu Phe Gly Ala Ser Thr Thr Arg
                660                 665                 670

Phe Leu Leu Gly Leu Leu Ser Asp Glu Gly Glu Arg Glu Met Glu Asn
            675                 680                 685

Ile Phe His Cys Arg Leu Ser Gln Gly Arg Asn Leu Met Gln Trp Val
        690                 695                 700

Pro Ser Leu Gln Leu Leu Leu Gln Pro His Ser Leu Glu Ser Leu His
705                 710                 715                 720

Cys Leu Tyr Glu Thr Arg Asn Lys Thr Phe Leu Thr Gln Val Met Ala
                725                 730                 735
```

-continued

His Phe Glu Glu Met Gly Met Cys Val Thr Asp Met Glu Leu Leu
                740                 745                 750

Val Cys Thr Phe Cys Ile Lys Phe Ser Arg His Val Lys Lys Leu Gln
        755                 760                 765

Leu Ile Glu Gly Arg Gln His Arg Ser Thr Trp Ser Pro Thr Met Val
    770                 775                 780

Val Leu Leu Ala Gly Cys Gly Leu Thr Ala Glu Asp Cys Lys Asp Leu
785                 790                 795                 800

Ala Phe Gly Leu Arg Ala Asn Gln Thr Leu Thr Glu Leu Asp Leu Ser
                805                 810                 815

Phe Asn Val Leu Thr Asp Ala Gly Ala Lys His Leu Cys Gln Arg Leu
                820                 825                 830

Arg Gln Pro Ser Cys Lys Leu Gln Arg Leu Gln Leu Val Ser Cys Gly
                835                 840                 845

Leu Thr Ser Asp Cys Cys Gln Asp Leu Ala Ser Val Leu Ser Ala Ser
        850                 855                 860

Pro Ser Leu Lys Glu Leu Asp Leu Gln Gln Asn Asn Leu Asp Asp Val
865                 870                 875                 880

Gly Val Arg Leu Leu Cys Glu Gly Leu Arg His Pro Ala Cys Lys Leu
                885                 890                 895

Ile Arg Leu Gly Leu Asp Gln Thr Thr Leu Ser Asp Glu Met Arg Gln
                900                 905                 910

Glu Leu Arg Ala Leu Glu Gln Glu Lys Pro Gln Leu Leu Ile Phe Ser
                915                 920                 925

Arg Arg Lys Pro Ser Val Met Thr Pro Thr Glu Gly Leu Asp Thr Gly
        930                 935                 940

Glu Met Ser Asn Ser Thr Ser Ser Leu Lys Arg Gln Arg Leu Gly Ser
945                 950                 955                 960

Glu Arg Ala Ala Ser His Val Ala Gln Ala Asn Leu Lys Leu Leu Asp
                965                 970                 975

Val Ser Lys Ile Phe Pro Ile Ala Glu Ile Ala Glu Glu Ser Ser Pro
                980                 985                 990

Glu Val Val Pro Val Glu Leu Leu Cys Val Pro Ser Pro Ala Ser Gln
        995                 1000                1005

Gly Asp Leu His Thr Lys Pro Leu Gly Thr Asp Asp Phe Trp
    1010                1015                1020

Gly Pro Thr Gly Pro Val Ala Thr Glu Val Val Asp Lys Glu Lys
    1025                1030                1035

Asn Leu Tyr Arg Val His Phe Pro Val Ala Gly Ser Tyr Arg Trp
    1040                1045                1050

Pro Asn Thr Gly Leu Cys Phe Val Met Arg Glu Ala Val Thr Val
    1055                1060                1065

Glu Ile Glu Phe Cys Val Trp Asp Gln Phe Leu Gly Glu Ile Asn
    1070                1075                1080

Pro Gln His Ser Trp Met Val Ala Gly Pro Leu Leu Asp Ile Lys
    1085                1090                1095

Ala Glu Pro Gly Ala Val Glu Ala Val His Leu Pro His Phe Val
    1100                1105                1110

Ala Leu Gln Gly Gly His Val Asp Thr Ser Leu Phe Gln Met Ala
    1115                1120                1125

His Phe Lys Glu Glu Gly Met Leu Leu Glu Lys Pro Ala Arg Val
    1130                1135                1140

-continued

Glu Leu His His Ile Val Leu Glu Asn Pro Ser Phe Ser Pro Leu
    1145                1150                1155

Gly Val Leu Leu Lys Met Ile His Asn Ala Leu Arg Phe Ile Pro
    1160                1165                1170

Val Thr Ser Val Val Leu Leu Tyr His Arg Val His Pro Glu Glu
    1175                1180                1185

Val Thr Phe His Leu Tyr Leu Ile Pro Ser Asp Cys Ser Ile Arg
    1190                1195                1200

<210> SEQ ID NO 12
<211> LENGTH: 1473
<212> TYPE: PRT
<213> ORGANISM: Artificial Sequence
<220> FEATURE:
<223> OTHER INFORMATION: Synthesized

<400> SEQUENCE: 12

Met Ala Gly Gly Ala Trp Gly Arg Leu Ala Cys Tyr Leu Glu Phe Leu
1               5                   10                  15

Lys Lys Glu Glu Leu Lys Glu Phe Gln Leu Leu Leu Ala Asn Lys Ala
            20                  25                  30

His Ser Arg Ser Ser Ser Gly Glu Thr Pro Ala Gln Pro Glu Lys Thr
        35                  40                  45

Ser Gly Met Glu Val Thr Ser Tyr Leu Val Ala Gln Tyr Gly Glu Gln
    50                  55                  60

Arg Ala Trp Asp Leu Ala Leu His Thr Trp Glu Gln Met Gly Leu Arg
65                  70                  75                  80

Ser Leu Cys Ala Gln Ala Gln Glu Gly Ala Gly His Ser Pro Ser Phe
                85                  90                  95

Pro Tyr Ser Pro Ser Glu Pro His Leu Gly Ser Pro Ser Gln Pro Thr
            100                 105                 110

Ser Thr Ala Val Leu Met Pro Trp Ile His Glu Leu Pro Ala Gly Cys
        115                 120                 125

Thr Gln Gly Ser Glu Arg Arg Val Leu Arg Gln Leu Pro Asp Thr Ser
    130                 135                 140

Gly Arg Arg Trp Arg Glu Ile Ser Ala Ser Leu Leu Tyr Gln Ala Leu
145                 150                 155                 160

Pro Ser Ser Pro Asp His Glu Ser Pro Ser Gln Glu Ser Pro Asn Ala
                165                 170                 175

Pro Thr Ser Thr Ala Val Leu Gly Ser Trp Gly Ser Pro Pro Gln Pro
            180                 185                 190

Ser Leu Ala Pro Arg Glu Gln Glu Ala Pro Gly Thr Gln Trp Pro Leu
        195                 200                 205

Asp Glu Thr Ser Gly Ile Tyr Tyr Thr Glu Ile Arg Glu Arg Glu Arg
    210                 215                 220

Glu Lys Ser Glu Lys Gly Arg Pro Pro Trp Ala Ala Val Val Gly Thr
225                 230                 235                 240

Pro Pro Gln Ala His Thr Ser Leu Gln Pro His His Pro Trp Glu
                245                 250                 255

Pro Ser Val Arg Glu Ser Leu Cys Ser Thr Trp Pro Trp Lys Asn Glu
            260                 265                 270

Asp Phe Asn Gln Lys Phe Thr Gln Leu Leu Leu Leu Gln Arg Pro His
        275                 280                 285

Pro Arg Ser Gln Asp Pro Leu Val Lys Arg Ser Trp Pro Asp Tyr Val
    290                 295                 300

```
Glu Asn Arg Gly His Leu Ile Glu Ile Arg Asp Leu Phe Gly Pro
305                 310                 315                 320

Gly Leu Asp Thr Gln Glu Pro Arg Ile Val Ile Leu Gln Gly Ala Ala
                325                 330                 335

Gly Ile Gly Lys Ser Thr Leu Ala Arg Gln Val Lys Glu Ala Trp Gly
            340                 345                 350

Arg Gly Gln Leu Tyr Gly Asp Arg Phe Gln His Val Phe Tyr Phe Ser
        355                 360                 365

Cys Arg Glu Leu Ala Gln Ser Lys Val Val Ser Leu Ala Glu Leu Ile
    370                 375                 380

Gly Lys Asp Gly Thr Ala Thr Pro Ala Pro Ile Arg Gln Ile Leu Ser
385                 390                 395                 400

Arg Pro Glu Arg Leu Leu Phe Ile Leu Asp Gly Val Asp Glu Pro Gly
                405                 410                 415

Trp Val Leu Gln Glu Pro Ser Ser Glu Leu Cys Leu His Trp Ser Gln
            420                 425                 430

Pro Gln Pro Ala Asp Ala Leu Leu Gly Ser Leu Leu Gly Lys Thr Ile
        435                 440                 445

Leu Pro Glu Ala Ser Phe Leu Ile Thr Ala Arg Thr Thr Ala Leu Gln
    450                 455                 460

Asn Leu Ile Pro Ser Leu Glu Gln Ala Arg Trp Val Glu Val Leu Gly
465                 470                 475                 480

Phe Ser Glu Ser Ser Arg Lys Glu Tyr Phe Tyr Arg Tyr Phe Thr Asp
                485                 490                 495

Glu Arg Gln Ala Ile Arg Ala Phe Arg Leu Val Lys Ser Asn Lys Glu
            500                 505                 510

Leu Trp Ala Leu Cys Leu Val Pro Trp Val Ser Trp Leu Ala Cys Thr
        515                 520                 525

Cys Leu Met Gln Gln Met Lys Arg Lys Glu Lys Leu Thr Leu Thr Ser
    530                 535                 540

Lys Thr Thr Thr Thr Leu Cys Leu His Tyr Leu Ala Gln Ala Leu Gln
545                 550                 555                 560

Ala Gln Pro Leu Gly Pro Gln Leu Arg Asp Leu Cys Ser Leu Ala Ala
                565                 570                 575

Glu Gly Ile Trp Gln Lys Lys Thr Leu Phe Ser Pro Asp Asp Leu Arg
            580                 585                 590

Lys His Gly Leu Asp Gly Ala Ile Ile Ser Thr Phe Leu Lys Met Gly
        595                 600                 605

Ile Leu Gln Glu His Pro Ile Pro Leu Ser Tyr Ser Phe Ile His Leu
    610                 615                 620

Cys Phe Gln Glu Phe Phe Ala Ala Met Ser Tyr Val Leu Glu Asp Glu
625                 630                 635                 640

Lys Gly Arg Gly Lys His Ser Asn Cys Ile Ile Asp Leu Glu Lys Thr
                645                 650                 655

Leu Glu Ala Tyr Gly Ile His Gly Leu Phe Gly Ala Ser Thr Thr Arg
            660                 665                 670

Phe Leu Leu Gly Leu Leu Ser Asp Glu Gly Glu Arg Glu Met Glu Asn
        675                 680                 685

Ile Phe His Cys Arg Leu Ser Gln Gly Arg Asn Leu Met Gln Trp Val
    690                 695                 700

Pro Ser Leu Gln Leu Leu Leu Gln Pro His Ser Leu Glu Ser Leu His
705                 710                 715                 720
```

```
Cys Leu Tyr Glu Thr Arg Asn Lys Thr Phe Leu Thr Gln Val Met Ala
            725                 730                 735

His Phe Glu Glu Met Gly Met Cys Val Glu Thr Asp Met Glu Leu Leu
            740                 745                 750

Val Cys Thr Phe Cys Ile Lys Phe Ser Arg His Val Lys Lys Leu Gln
            755                 760                 765

Leu Ile Glu Gly Arg Gln His Arg Ser Thr Trp Ser Pro Thr Met Val
770                 775                 780

Val Leu Phe Arg Trp Val Pro Val Thr Asp Ala Tyr Trp Gln Ile Leu
785                 790                 795                 800

Phe Ser Val Leu Lys Val Thr Arg Asn Leu Lys Glu Leu Asp Leu Ser
                805                 810                 815

Gly Asn Ser Leu Ser His Ser Ala Val Lys Ser Leu Cys Lys Thr Leu
                820                 825                 830

Arg Arg Pro Arg Cys Leu Leu Glu Thr Leu Arg Leu Ala Gly Cys Gly
                835                 840                 845

Leu Thr Ala Glu Asp Cys Lys Asp Leu Ala Phe Gly Leu Arg Ala Asn
    850                 855                 860

Gln Thr Leu Thr Glu Leu Asp Leu Ser Phe Asn Val Leu Thr Asp Ala
865                 870                 875                 880

Gly Ala Lys His Leu Cys Gln Arg Leu Arg Gln Pro Ser Cys Lys Leu
                885                 890                 895

Gln Arg Leu Gln Leu Val Ser Cys Gly Leu Thr Ser Asp Cys Cys Gln
                900                 905                 910

Asp Leu Ala Ser Val Leu Ser Ala Ser Pro Ser Leu Lys Glu Leu Asp
                915                 920                 925

Leu Gln Gln Asn Asn Leu Asp Asp Val Gly Val Arg Leu Leu Cys Glu
                930                 935                 940

Gly Leu Arg His Pro Ala Cys Lys Leu Ile Arg Leu Gly Leu Asp Gln
945                 950                 955                 960

Thr Thr Leu Ser Asp Glu Met Arg Gln Glu Leu Arg Ala Leu Glu Gln
                965                 970                 975

Glu Lys Pro Gln Leu Leu Ile Phe Ser Arg Arg Lys Pro Ser Val Met
                980                 985                 990

Thr Pro Thr Glu Gly Leu Asp Thr Gly Glu Met Ser Asn Ser Thr Ser
        995                 1000                1005

Ser Leu Lys Arg Gln Arg Leu Gly Ser Glu Arg Ala Ala Ser His
        1010                1015                1020

Val Ala Gln Ala Asn Leu Lys Leu Leu Asp Val Ser Lys Ile Phe
        1025                1030                1035

Pro Ile Ala Glu Ile Ala Glu Glu Ser Ser Pro Glu Val Val Pro
        1040                1045                1050

Val Glu Leu Leu Cys Val Pro Ser Pro Ala Ser Gln Gly Asp Leu
        1055                1060                1065

His Thr Lys Pro Leu Gly Thr Asp Asp Asp Phe Trp Gly Pro Thr
        1070                1075                1080

Gly Pro Val Ala Thr Glu Val Val Asp Lys Glu Lys Asn Leu Tyr
        1085                1090                1095

Arg Val His Phe Pro Val Ala Gly Ser Tyr Arg Trp Pro Asn Thr
        1100                1105                1110

Gly Leu Cys Phe Val Met Arg Glu Ala Val Thr Val Glu Ile Glu
        1115                1120                1125
```

Phe Cys Val Trp Asp Gln Phe Leu Gly Glu Ile Asn Pro Gln His
    1130            1135                1140

Ser Trp Met Val Ala Gly Pro Leu Leu Asp Ile Lys Ala Glu Pro
    1145            1150                1155

Gly Ala Val Glu Ala Val His Leu Pro His Phe Val Ala Leu Gln
    1160            1165                1170

Gly Gly His Val Asp Thr Ser Leu Phe Gln Met Ala His Phe Lys
    1175            1180                1185

Glu Glu Gly Met Leu Leu Glu Lys Pro Ala Arg Val Glu Leu His
    1190            1195                1200

His Ile Val Leu Glu Asn Pro Ser Phe Ser Pro Leu Gly Val Leu
    1205            1210                1215

Leu Lys Met Ile His Asn Ala Leu Arg Phe Ile Pro Val Thr Ser
    1220            1225                1230

Val Val Leu Leu Tyr His Arg Val His Pro Glu Glu Val Thr Phe
    1235            1240                1245

His Leu Tyr Leu Ile Pro Ser Asp Cys Ser Ile Arg Lys Ala Ile
    1250            1255                1260

Asp Asp Leu Glu Met Lys Phe Gln Phe Val Arg Ile His Lys Pro
    1265            1270                1275

Pro Pro Leu Thr Pro Leu Tyr Met Gly Cys Arg Tyr Thr Val Ser
    1280            1285                1290

Gly Ser Gly Ser Gly Met Leu Glu Ile Leu Pro Lys Glu Leu Glu
    1295            1300                1305

Leu Cys Tyr Arg Ser Pro Gly Glu Asp Gln Leu Phe Ser Glu Phe
    1310            1315                1320

Tyr Val Gly His Leu Gly Ser Gly Ile Arg Leu Gln Val Lys Asp
    1325            1330                1335

Lys Lys Asp Glu Thr Leu Val Trp Glu Ala Leu Val Lys Pro Gly
    1340            1345                1350

Asp Leu Met Pro Ala Thr Thr Leu Ile Pro Pro Ala Arg Ile Ala
    1355            1360                1365

Val Pro Ser Pro Leu Asp Ala Pro Gln Leu Leu His Phe Val Asp
    1370            1375                1380

Gln Tyr Arg Glu Gln Leu Ile Ala Arg Val Thr Ser Val Glu Val
    1385            1390                1395

Val Leu Asp Lys Leu His Gly Gln Val Leu Ser Gln Glu Gln Tyr
    1400            1405                1410

Glu Arg Val Leu Ala Glu Asn Thr Arg Pro Ser Gln Met Arg Lys
    1415            1420                1425

Leu Phe Ser Leu Ser Gln Ser Trp Asp Arg Lys Cys Lys Asp Gly
    1430            1435                1440

Leu Tyr Gln Ala Leu Lys Glu Thr His Pro His Leu Ile Met Glu
    1445            1450                1455

Leu Trp Glu Lys Gly Ser Lys Lys Gly Leu Leu Pro Leu Ser Ser
    1460            1465                1470

<210> SEQ ID NO 13
<211> LENGTH: 1473
<212> TYPE: PRT
<213> ORGANISM: Artificial Sequence
<220> FEATURE:
<223> OTHER INFORMATION: Synthesized

<400> SEQUENCE: 13

```
Met Ala Gly Gly Ala Trp Gly Arg Leu Ala Cys Tyr Leu Glu Phe Leu
1               5                   10                  15

Lys Lys Glu Glu Leu Lys Glu Phe Gln Leu Leu Ala Asn Lys Ala
            20                  25                  30

His Ser Arg Ser Ser Gly Glu Thr Pro Ala Gln Pro Glu Lys Thr
            35                  40                  45

Ser Gly Met Glu Val Ala Ser Tyr Leu Val Ala Gln Tyr Gly Glu Gln
    50                  55                  60

Arg Val Trp Asp Leu Ala Leu His Thr Trp Glu Gln Met Gly Leu Arg
65                  70                  75                  80

Ser Leu Cys Ala Gln Ala Gln Glu Gly Ala Gly His Ser Pro Ser Phe
                85                  90                  95

Pro Tyr Ser Pro Ser Glu Pro His Leu Gly Ser Pro Ser Gln Pro Thr
            100                 105                 110

Ser Thr Ala Val Leu Met Pro Trp Ile His Glu Leu Pro Ala Gly Cys
            115                 120                 125

Thr Gln Gly Ser Glu Arg Arg Val Leu Arg Gln Leu Pro Asp Thr Ser
    130                 135                 140

Gly Arg Arg Trp Arg Glu Ile Ser Ala Ser Leu Leu Tyr Gln Ala Leu
145                 150                 155                 160

Pro Ser Ser Pro Asp His Glu Ser Pro Ser Gln Glu Ser Pro Asn Ala
                165                 170                 175

Pro Thr Ser Thr Ala Val Leu Gly Ser Trp Gly Ser Pro Pro Gln Pro
            180                 185                 190

Ser Leu Ala Pro Arg Glu Gln Glu Ala Pro Gly Thr Gln Trp Pro Leu
            195                 200                 205

Asp Glu Thr Ser Gly Ile Tyr Tyr Thr Glu Ile Arg Glu Arg Glu Arg
    210                 215                 220

Glu Lys Ser Glu Lys Gly Arg Pro Pro Trp Ala Ala Val Val Gly Thr
225                 230                 235                 240

Pro Pro Gln Ala His Thr Ser Leu Gln Pro His His Pro Trp Glu
                245                 250                 255

Pro Ser Val Arg Glu Ser Leu Cys Ser Thr Trp Pro Trp Lys Asn Glu
            260                 265                 270

Asp Phe Asn Gln Lys Phe Thr Gln Leu Leu Leu Gln Arg Pro His
            275                 280                 285

Pro Arg Ser Gln Asp Pro Leu Val Lys Arg Ser Trp Pro Asp Tyr Val
    290                 295                 300

Glu Glu Asn Arg Gly His Leu Ile Glu Ile Arg Asp Leu Phe Gly Pro
305                 310                 315                 320

Gly Leu Asp Thr Gln Glu Pro Arg Ile Val Ile Leu Gln Gly Ala Ala
            325                 330                 335

Gly Ile Gly Lys Ser Thr Leu Ala Arg Gln Val Lys Glu Ala Trp Gly
            340                 345                 350

Arg Gly Gln Leu Tyr Gly Asp Arg Phe Gln His Val Phe Tyr Phe Ser
    355                 360                 365

Cys Arg Glu Leu Ala Gln Ser Lys Val Val Ser Leu Ala Glu Leu Ile
    370                 375                 380

Gly Lys Asp Gly Thr Ala Thr Pro Ala Pro Ile Arg Gln Ile Leu Ser
385                 390                 395                 400
```

```
Arg Pro Glu Arg Leu Leu Phe Ile Leu Asp Gly Val Asp Glu Pro Gly
                405                 410                 415

Trp Val Leu Gln Glu Pro Ser Ser Glu Leu Cys Leu His Trp Ser Gln
            420                 425                 430

Pro Gln Pro Ala Asp Ala Leu Leu Gly Ser Leu Leu Gly Lys Thr Ile
        435                 440                 445

Leu Pro Glu Ala Ser Phe Leu Ile Thr Ala Arg Thr Thr Ala Leu Gln
    450                 455                 460

Asn Leu Ile Pro Ser Leu Glu Gln Ala Arg Trp Val Glu Val Leu Gly
465                 470                 475                 480

Phe Ser Glu Ser Ser Arg Lys Glu Tyr Phe Tyr Arg Tyr Phe Thr Asp
                485                 490                 495

Glu Arg Gln Ala Ile Arg Ala Phe Arg Leu Val Lys Ser Asn Lys Glu
            500                 505                 510

Leu Trp Ala Leu Cys Leu Val Pro Trp Val Ser Trp Leu Ala Cys Thr
        515                 520                 525

Cys Leu Met Gln Gln Met Lys Arg Lys Glu Lys Leu Thr Leu Thr Ser
    530                 535                 540

Lys Thr Thr Thr Thr Leu Cys Leu His Tyr Leu Ala Gln Ala Leu Gln
545                 550                 555                 560

Ala Gln Pro Leu Gly Pro Gln Leu Arg Asp Leu Cys Ser Leu Ala Ala
                565                 570                 575

Glu Gly Ile Trp Gln Lys Lys Thr Leu Phe Ser Pro Asp Asp Leu Arg
            580                 585                 590

Lys His Gly Leu Asp Gly Ala Ile Ile Ser Thr Phe Leu Lys Met Gly
        595                 600                 605

Ile Leu Gln Glu His Pro Ile Pro Leu Ser Tyr Ser Phe Ile His Leu
    610                 615                 620

Cys Phe Gln Glu Phe Phe Ala Ala Met Ser Tyr Val Leu Glu Asp Glu
625                 630                 635                 640

Lys Gly Arg Gly Lys His Ser Asn Cys Ile Ile Asp Leu Glu Lys Thr
                645                 650                 655

Leu Glu Ala Tyr Gly Ile His Gly Leu Phe Gly Ala Ser Thr Thr Arg
            660                 665                 670

Phe Leu Leu Gly Leu Leu Ser Asp Glu Gly Glu Arg Glu Met Glu Asn
        675                 680                 685

Ile Phe His Cys Arg Leu Ser Gln Gly Arg Asn Leu Met Gln Trp Val
    690                 695                 700

Pro Ser Leu Gln Leu Leu Leu Gln Pro His Ser Leu Glu Ser Leu His
705                 710                 715                 720

Cys Leu Tyr Glu Thr Arg Asn Lys Thr Phe Leu Thr Gln Val Met Ala
                725                 730                 735

His Phe Glu Glu Met Gly Met Cys Val Glu Thr Asp Met Glu Leu Leu
            740                 745                 750

Val Cys Thr Phe Cys Ile Lys Phe Ser Arg His Val Lys Lys Leu Gln
        755                 760                 765

Leu Ile Glu Gly Arg Gln His Arg Ser Thr Trp Ser Pro Thr Met Val
    770                 775                 780

Val Leu Phe Arg Trp Val Pro Val Thr Asp Ala Tyr Trp Gln Ile Leu
785                 790                 795                 800

Phe Ser Val Leu Lys Val Thr Arg Asn Leu Lys Glu Leu Asp Leu Ser
                805                 810                 815
```

-continued

```
Gly Asn Ser Leu Ser His Ser Ala Val Lys Ser Leu Cys Lys Thr Leu
            820                 825                 830

Arg Arg Pro Arg Cys Leu Leu Glu Thr Leu Arg Leu Ala Gly Cys Gly
        835                 840                 845

Leu Thr Ala Glu Asp Cys Lys Asp Leu Ala Phe Gly Leu Arg Ala Asn
850                 855                 860

Gln Thr Leu Thr Glu Leu Asp Leu Ser Phe Asn Val Leu Thr Asp Ala
865                 870                 875                 880

Gly Ala Lys His Leu Cys Gln Arg Leu Arg Gln Pro Ser Cys Lys Leu
            885                 890                 895

Gln Arg Leu Gln Leu Val Ser Cys Gly Leu Thr Ser Asp Cys Cys Gln
        900                 905                 910

Asp Leu Ala Ser Val Leu Ser Ala Ser Pro Ser Leu Lys Glu Leu Asp
        915                 920                 925

Leu Gln Gln Asn Asn Leu Asp Asp Val Gly Val Arg Leu Leu Cys Glu
    930                 935                 940

Gly Leu Arg His Pro Ala Cys Lys Leu Ile Arg Leu Gly Leu Asp Gln
945                 950                 955                 960

Thr Thr Leu Ser Asp Glu Met Arg Gln Glu Leu Arg Ala Leu Glu Gln
            965                 970                 975

Glu Lys Pro Gln Leu Leu Ile Phe Ser Arg Arg Lys Pro Ser Val Met
        980                 985                 990

Thr Pro Thr Glu Gly Leu Asp Thr Gly Glu Met Ser Asn Ser Thr Ser
        995                 1000                1005

Ser Leu Lys Arg Gln Arg Leu Gly Ser Glu Arg Ala Ala Ser His
    1010                1015                1020

Val Ala Gln Ala Asn Leu Lys Leu Leu Asp Val Ser Lys Ile Phe
    1025                1030                1035

Pro Ile Ala Glu Ile Ala Glu Glu Ser Ser Pro Glu Val Val Pro
    1040                1045                1050

Val Glu Leu Leu Cys Val Pro Ser Pro Ala Ser Gln Gly Asp Leu
    1055                1060                1065

His Thr Lys Pro Leu Gly Thr Asp Asp Asp Phe Trp Gly Pro Thr
    1070                1075                1080

Gly Pro Val Ala Thr Glu Val Val Asp Lys Glu Lys Asn Leu Tyr
    1085                1090                1095

Arg Val His Phe Pro Val Ala Gly Ser Tyr Arg Trp Pro Asn Thr
    1100                1105                1110

Gly Leu Cys Phe Val Met Arg Glu Ala Val Thr Val Glu Ile Glu
    1115                1120                1125

Phe Cys Val Trp Asp Gln Phe Leu Gly Glu Ile Asn Pro Gln His
    1130                1135                1140

Ser Trp Met Val Ala Gly Pro Leu Leu Asp Ile Lys Ala Glu Pro
    1145                1150                1155

Gly Ala Val Glu Ala Val His Leu Pro His Phe Val Ala Leu Gln
    1160                1165                1170

Gly Gly His Val Asp Thr Ser Leu Phe Gln Met Ala His Phe Lys
    1175                1180                1185

Glu Glu Gly Met Leu Leu Glu Lys Pro Ala Arg Val Glu Leu His
    1190                1195                1200

His Ile Val Leu Glu Asn Pro Ser Phe Ser Pro Leu Gly Val Leu
    1205                1210                1215
```

Leu Lys Met Ile His Asn Ala Leu Arg Phe Ile Pro Val Thr Ser
      1220                1225                1230

Val Val Leu Leu Tyr His Arg Val His Pro Glu Glu Val Thr Phe
      1235                1240                1245

His Leu Tyr Leu Ile Pro Ser Asp Cys Ser Ile Arg Lys Ala Ile
      1250                1255                1260

Asp Asp Leu Glu Met Lys Phe Gln Phe Val Arg Ile His Lys Pro
      1265                1270                1275

Pro Pro Leu Thr Pro Leu Tyr Met Gly Cys Arg Tyr Thr Val Ser
      1280                1285                1290

Gly Ser Gly Ser Gly Met Leu Glu Ile Leu Pro Lys Glu Leu Glu
      1295                1300                1305

Leu Cys Tyr Arg Ser Pro Gly Glu Asp Gln Leu Phe Ser Glu Phe
      1310                1315                1320

Tyr Val Gly His Leu Gly Ser Gly Ile Arg Leu Gln Val Lys Asp
      1325                1330                1335

Lys Lys Asp Glu Thr Leu Val Trp Glu Ala Leu Val Lys Pro Gly
      1340                1345                1350

Asp Leu Met Pro Ala Thr Thr Leu Ile Pro Pro Ala Arg Ile Ala
      1355                1360                1365

Val Pro Ser Pro Leu Asp Ala Pro Gln Leu Leu His Phe Val Asp
      1370                1375                1380

Gln Tyr Arg Glu Gln Leu Ile Ala Arg Val Thr Ser Val Glu Val
      1385                1390                1395

Val Leu Asp Lys Leu His Gly Gln Val Leu Ser Gln Glu Gln Tyr
      1400                1405                1410

Glu Arg Val Leu Ala Glu Asn Thr Arg Pro Ser Gln Met Arg Lys
      1415                1420                1425

Leu Phe Ser Leu Ser Gln Ser Trp Asp Arg Lys Cys Lys Asp Gly
      1430                1435                1440

Leu Tyr Gln Ala Leu Lys Glu Thr His Pro His Leu Ile Met Glu
      1445                1450                1455

Leu Trp Glu Lys Gly Ser Lys Lys Gly Leu Leu Pro Leu Ser Ser
      1460                1465                1470

<210> SEQ ID NO 14
<211> LENGTH: 1473
<212> TYPE: PRT
<213> ORGANISM: Artificial Sequence
<220> FEATURE:
<223> OTHER INFORMATION: Synthesized

<400> SEQUENCE: 14

Met Ala Gly Gly Ala Trp Gly Arg Leu Ala Cys Tyr Leu Glu Phe Leu
1               5                   10                  15

Lys Lys Glu Glu Leu Lys Glu Phe Gln Leu Leu Leu Ala Asn Lys Ala
                20                  25                  30

His Ser Arg Ser Ser Ser Gly Glu Thr Pro Ala Gln Pro Glu Lys Thr
            35                  40                  45

Ser Gly Met Glu Val Ala Ser Tyr Leu Val Ala Gln Tyr Gly Glu Gln
        50                  55                  60

Arg Ala Trp Asp Leu Ala Leu His Thr Trp Glu Gln Met Gly Leu Arg
65                  70                  75                  80

Ser Leu Cys Ala Gln Ala Gln Glu Gly Ala Gly His Ser Pro Ser Phe
                85                  90                  95

```
Pro Tyr Ser Pro Ser Glu Pro His Leu Gly Ser Pro Ser Gln Pro Thr
            100                 105                 110

Ser Thr Ala Val Leu Met Pro Trp Ile His Glu Leu Pro Ala Gly Cys
            115                 120                 125

Thr Gln Gly Ser Glu Arg Arg Val Leu Arg Gln Leu Pro Asp Thr Ser
            130                 135                 140

Gly Arg Arg Trp Arg Glu Ile Ser Ala Ser Leu Leu Tyr Gln Ala Leu
145                 150                 155                 160

Pro Ser Ser Pro Asp His Glu Ser Pro Ser Gln Glu Ser Pro Asn Ala
                    165                 170                 175

Pro Thr Ser Thr Ala Val Leu Gly Ser Trp Gly Ser Pro Pro Gln Pro
            180                 185                 190

Ser Leu Ala Pro Arg Glu Gln Glu Ala Pro Gly Thr Gln Trp Pro Leu
            195                 200                 205

Asp Glu Thr Ser Gly Ile Tyr Tyr Thr Glu Ile Arg Glu Arg Glu Arg
            210                 215                 220

Glu Lys Ser Glu Lys Gly Arg Pro Pro Trp Ala Ala Val Val Gly Thr
225                 230                 235                 240

Pro Pro Gln Ala His Thr Ser Leu Gln Pro His His His Pro Trp Glu
            245                 250                 255

Pro Ser Val Arg Glu Ser Leu Cys Ser Thr Trp Pro Trp Lys Asn Glu
            260                 265                 270

Asp Phe Asn Gln Lys Phe Thr Gln Leu Leu Leu Leu Gln Arg Pro His
            275                 280                 285

Pro Arg Ser Gln Asp Pro Leu Val Lys Arg Ser Trp Pro Asp Tyr Val
            290                 295                 300

Glu Glu Asn Arg Gly His Leu Ile Glu Ile Arg Asp Leu Phe Gly Pro
305                 310                 315                 320

Gly Leu Asp Thr Gln Glu Pro Arg Ile Val Ile Leu Gln Gly Ala Ala
            325                 330                 335

Gly Ile Gly Lys Ser Thr Leu Ala Arg Gln Val Lys Glu Ala Trp Gly
            340                 345                 350

Arg Gly Gln Leu Tyr Gly Asp Arg Phe Gln His Val Phe Tyr Phe Ser
            355                 360                 365

Cys Arg Glu Leu Ala Gln Ser Lys Val Val Ser Leu Ala Glu Leu Ile
            370                 375                 380

Gly Lys Asp Gly Thr Ala Thr Pro Ala Pro Ile Arg Gln Ile Leu Ser
385                 390                 395                 400

Arg Pro Glu Arg Leu Leu Phe Ile Leu Asp Gly Val Asp Glu Pro Gly
                    405                 410                 415

Trp Val Leu Gln Glu Pro Ser Ser Glu Leu Cys Leu His Trp Ser Gln
            420                 425                 430

Pro Gln Pro Ala Asp Ala Leu Leu Gly Ser Leu Leu Gly Lys Thr Ile
            435                 440                 445

Leu Pro Glu Ala Ser Phe Leu Ile Thr Ala Arg Thr Thr Ala Leu Gln
            450                 455                 460

Asn Leu Ile Pro Ser Leu Glu Gln Ala Arg Trp Val Glu Val Leu Gly
465                 470                 475                 480

Phe Ser Glu Ser Ser Arg Lys Glu Tyr Phe Tyr Arg Tyr Phe Thr Asp
                    485                 490                 495

Glu Arg Gln Ala Ile Arg Ala Phe Arg Leu Val Lys Ser Asn Lys Glu
            500                 505                 510
```

```
Leu Trp Ala Leu Cys Leu Val Pro Trp Val Ser Trp Leu Ala Cys Thr
            515                 520                 525

Cys Leu Met Gln Gln Met Lys Arg Lys Glu Lys Leu Thr Leu Thr Ser
530                 535                 540

Lys Thr Thr Thr Thr Leu Cys Leu His Tyr Leu Ala Gln Ala Leu Gln
545                 550                 555                 560

Ala Gln Pro Leu Gly Pro Gln Leu Arg Asp Leu Cys Ser Leu Ala Ala
                565                 570                 575

Glu Gly Ile Trp Gln Lys Lys Thr Leu Phe Ser Pro Asp Asp Leu Arg
            580                 585                 590

Lys His Gly Leu Asp Gly Ala Ile Ile Ser Thr Phe Leu Lys Met Gly
            595                 600                 605

Ile Leu Gln Glu His Pro Ile Pro Leu Ser Tyr Ser Phe Ile His Leu
            610                 615                 620

Cys Phe Gln Glu Phe Phe Ala Ala Met Ser Tyr Val Leu Glu Asp Glu
625                 630                 635                 640

Lys Gly Arg Gly Lys His Ser Asn Cys Ile Ile Asp Leu Glu Lys Thr
                645                 650                 655

Leu Glu Ala Tyr Gly Ile His Gly Leu Phe Gly Ala Ser Thr Thr Arg
            660                 665                 670

Phe Leu Leu Gly Leu Leu Ser Asp Glu Gly Glu Arg Glu Met Glu Asn
675                 680                 685

Ile Phe His Cys Arg Leu Ser Gln Gly Arg Asn Leu Met Gln Trp Val
            690                 695                 700

Pro Ser Leu Gln Leu Leu Leu Gln Pro His Ser Leu Glu Ser Leu His
705                 710                 715                 720

Cys Leu Tyr Glu Thr Arg Asn Lys Thr Phe Leu Thr Gln Val Met Ala
                725                 730                 735

His Phe Glu Glu Met Gly Met Cys Val Glu Thr Asp Met Glu Leu Leu
            740                 745                 750

Val Cys Thr Phe Cys Ile Lys Phe Ser Arg His Val Lys Lys Leu Gln
                755                 760                 765

Leu Ile Glu Gly Arg Gln His Arg Ser Thr Trp Ser Pro Thr Met Val
770                 775                 780

Val Leu Phe Arg Trp Val Pro Val Thr Asp Ala Tyr Trp Gln Ile Leu
785                 790                 795                 800

Phe Ser Val Leu Lys Val Thr Arg Asn Leu Lys Glu Leu Asp Leu Ser
                805                 810                 815

Gly Asn Ser Leu Ser His Ser Ala Val Lys Ser Leu Cys Lys Thr Leu
            820                 825                 830

Arg Arg Pro Arg Cys Leu Leu Glu Thr Leu Arg Leu Ala Gly Cys Gly
                835                 840                 845

Leu Thr Ala Glu Asp Cys Lys Asp Leu Ala Phe Gly Leu Arg Ala Asn
            850                 855                 860

Gln Thr Leu Thr Glu Leu Asp Leu Ser Phe Asn Val Leu Thr Asp Ala
865                 870                 875                 880

Gly Ala Lys His Leu Cys Gln Arg Leu Arg Gln Pro Ser Cys Lys Leu
                885                 890                 895

Gln Arg Leu Gln Leu Val Ser Cys Gly Leu Thr Ser Asp Cys Cys Gln
                900                 905                 910

Asp Leu Ala Ser Val Leu Ser Ala Ser Pro Ser Leu Lys Glu Leu Asp
            915                 920                 925
```

```
Leu Gln Gln Asn Asn Leu Asp Asp Val Gly Val Arg Leu Leu Cys Glu
    930                 935                 940

Gly Leu Arg His Pro Ala Cys Lys Leu Ile Arg Leu Gly Leu Asp Gln
945                 950                 955                 960

Thr Thr Leu Ser Asp Glu Met Arg Gln Glu Leu Arg Ala Leu Glu Gln
            965                 970                 975

Glu Lys Pro Gln Leu Leu Ile Phe Ser Arg Arg Lys Pro Ser Val Met
                980                 985                 990

Thr Pro Thr Glu Gly Leu Asp Thr Gly Glu Met Ser Asn Ser Thr Ser
            995                 1000                1005

Ser Leu Lys Arg Gln Arg Leu Gly Ser Glu Arg Ala Ala Ser His
    1010                1015                1020

Val Ala Gln Ala Asn Leu Lys Leu Leu Asp Val Ser Lys Ile Phe
    1025                1030                1035

Pro Ile Ala Glu Ile Ala Glu Glu Ser Ser Pro Glu Val Val Pro
    1040                1045                1050

Val Glu Leu Leu Cys Val Pro Ser Pro Ala Ser Gln Gly Asp Leu
    1055                1060                1065

His Thr Lys Pro Leu Gly Thr Asp Asp Asp Phe Trp Gly Pro Thr
    1070                1075                1080

Gly Pro Val Ala Thr Glu Val Val Asp Lys Glu Lys Asn Leu Tyr
    1085                1090                1095

Arg Val His Phe Pro Val Ala Gly Ser Tyr Arg Trp Pro Asn Thr
    1100                1105                1110

Gly Leu Cys Phe Val Met Arg Glu Ala Val Thr Val Glu Ile Glu
    1115                1120                1125

Phe Cys Val Trp Asp Gln Phe Leu Gly Glu Ile Asn Pro Gln His
    1130                1135                1140

Ser Trp Met Val Ala Gly Pro Leu Leu Asp Ile Lys Ala Glu Pro
    1145                1150                1155

Gly Ala Val Glu Ala Val His Leu Pro His Phe Val Ala Leu Gln
    1160                1165                1170

Gly Gly His Val Asp Thr Ser Leu Phe Gln Val Ala His Phe Lys
    1175                1180                1185

Glu Glu Gly Met Leu Leu Glu Lys Pro Ala Arg Val Glu Leu His
    1190                1195                1200

His Ile Val Leu Glu Asn Pro Ser Phe Ser Pro Leu Gly Val Leu
    1205                1210                1215

Leu Lys Met Ile His Asn Ala Leu Arg Phe Ile Pro Val Thr Ser
    1220                1225                1230

Val Val Leu Leu Tyr His Arg Val His Pro Glu Glu Val Thr Phe
    1235                1240                1245

His Leu Tyr Leu Ile Pro Ser Asp Cys Ser Ile Arg Lys Ala Ile
    1250                1255                1260

Asp Asp Leu Glu Met Lys Phe Gln Phe Val Arg Ile His Lys Pro
    1265                1270                1275

Pro Pro Leu Thr Pro Leu Tyr Met Gly Cys Arg Tyr Thr Val Ser
    1280                1285                1290

Gly Ser Gly Ser Gly Met Leu Glu Ile Leu Pro Lys Glu Leu Glu
    1295                1300                1305

Leu Cys Tyr Arg Ser Pro Gly Glu Asp Gln Leu Phe Ser Glu Phe
    1310                1315                1320
```

```
Tyr Val Gly His Leu Gly Ser Gly Ile Arg Leu Gln Val Lys Asp
    1325                1330                1335

Lys Lys Asp Glu Thr Leu Val Trp Glu Ala Leu Val Lys Pro Gly
    1340                1345                1350

Asp Leu Met Pro Ala Thr Thr Leu Ile Pro Pro Ala Arg Ile Ala
    1355                1360                1365

Val Pro Ser Pro Leu Asp Ala Pro Gln Leu Leu His Phe Val Asp
    1370                1375                1380

Gln Tyr Arg Glu Gln Leu Ile Ala Arg Val Thr Ser Val Glu Val
    1385                1390                1395

Val Leu Asp Lys Leu His Gly Gln Val Leu Ser Gln Glu Gln Tyr
    1400                1405                1410

Glu Arg Val Leu Ala Glu Asn Thr Arg Pro Ser Gln Met Arg Lys
    1415                1420                1425

Leu Phe Ser Leu Ser Gln Ser Trp Asp Arg Lys Cys Lys Asp Gly
    1430                1435                1440

Leu Tyr Gln Ala Leu Lys Glu Thr His Pro His Leu Ile Met Glu
    1445                1450                1455

Leu Trp Glu Lys Gly Ser Lys Lys Gly Leu Leu Pro Leu Ser Ser
    1460                1465                1470

<210> SEQ ID NO 15
<211> LENGTH: 1203
<212> TYPE: PRT
<213> ORGANISM: Artificial Sequence
<220> FEATURE:
<223> OTHER INFORMATION: Synthesized

<400> SEQUENCE: 15

Met Ala Gly Gly Ala Trp Gly Arg Leu Ala Cys Tyr Leu Glu Phe Leu
1               5                   10                  15

Lys Lys Glu Glu Leu Lys Glu Phe Gln Leu Leu Leu Ala Asn Lys Ala
                20                  25                  30

His Ser Arg Ser Ser Ser Gly Glu Thr Pro Ala Gln Pro Glu Lys Thr
            35                  40                  45

Ser Gly Met Glu Val Ala Ser Tyr Leu Val Ala Gln Tyr Gly Glu Gln
        50                  55                  60

Arg Ala Trp Asp Leu Ala Leu His Thr Trp Glu Gln Met Gly Leu Arg
65                  70                  75                  80

Ser Leu Cys Ala Gln Ala Gln Glu Gly Ala Gly His Ser Pro Ser Phe
                85                  90                  95

Pro Tyr Ser Pro Ser Glu Pro His Leu Gly Ser Pro Ser Gln Pro Thr
            100                 105                 110

Ser Thr Ala Val Leu Met Pro Trp Ile His Glu Leu Pro Ala Gly Cys
        115                 120                 125

Thr Gln Gly Ser Glu Arg Arg Val Leu Arg Gln Leu Pro Asp Thr Ser
    130                 135                 140

Gly Arg Arg Trp Arg Glu Ile Ser Ala Ser Leu Leu Tyr Gln Ala Leu
145                 150                 155                 160

Pro Ser Ser Pro Asp His Glu Ser Pro Ser Gln Glu Ser Pro Asn Ala
                165                 170                 175

Pro Thr Ser Thr Ala Val Leu Gly Ser Trp Gly Ser Pro Pro Gln Pro
            180                 185                 190

Ser Leu Ala Pro Arg Glu Gln Glu Ala Pro Gly Thr Gln Trp Pro Leu
        195                 200                 205
```

```
Asp Glu Thr Ser Gly Ile Tyr Tyr Thr Glu Ile Arg Glu Arg Glu Arg
    210                 215                 220

Glu Lys Ser Glu Lys Gly Arg Pro Pro Trp Ala Ala Val Val Gly Thr
225                 230                 235                 240

Pro Pro Gln Ala His Thr Ser Leu Gln Pro His His His Pro Trp Glu
                245                 250                 255

Pro Ser Val Arg Glu Ser Leu Cys Ser Thr Trp Pro Trp Lys Asn Glu
            260                 265                 270

Asp Phe Asn Gln Lys Phe Thr Gln Leu Leu Leu Gln Arg Pro His
                275                 280                 285

Pro Arg Ser Gln Asp Pro Leu Val Lys Arg Ser Trp Pro Asp Tyr Val
290                 295                 300

Glu Glu Asn Arg Gly His Leu Ile Glu Ile Arg Asp Leu Phe Gly Pro
305                 310                 315                 320

Gly Leu Asp Thr Gln Glu Pro Arg Ile Val Ile Leu Gln Gly Ala Ala
                325                 330                 335

Gly Ile Gly Lys Ser Thr Leu Ala Arg Gln Val Lys Glu Ala Trp Gly
                340                 345                 350

Arg Gly Gln Leu Tyr Gly Asp Arg Phe Gln His Val Phe Tyr Phe Ser
                355                 360                 365

Cys Arg Glu Leu Ala Gln Ser Lys Val Val Ser Leu Ala Glu Leu Ile
            370                 375                 380

Gly Lys Asp Gly Thr Ala Thr Pro Ala Pro Ile Arg Gln Ile Leu Ser
385                 390                 395                 400

Arg Pro Glu Arg Leu Leu Phe Ile Leu Asp Gly Val Asp Glu Pro Gly
                405                 410                 415

Trp Val Leu Gln Glu Pro Ser Ser Glu Leu Cys Leu His Trp Ser Gln
                420                 425                 430

Pro Gln Pro Ala Asp Ala Leu Leu Gly Ser Leu Leu Gly Lys Thr Ile
            435                 440                 445

Leu Pro Glu Ala Ser Phe Leu Ile Thr Ala Arg Thr Thr Ala Leu Gln
450                 455                 460

Asn Leu Ile Pro Ser Leu Glu Gln Ala Arg Trp Val Glu Val Leu Gly
465                 470                 475                 480

Phe Ser Glu Ser Ser Arg Lys Glu Tyr Phe Arg Tyr Phe Thr Asp
                485                 490                 495

Glu Arg Gln Ala Ile Arg Ala Phe Arg Leu Val Lys Ser Asn Lys Glu
                500                 505                 510

Leu Trp Ala Leu Cys Leu Val Pro Trp Val Ser Trp Leu Ala Cys Thr
                515                 520                 525

Cys Leu Met Gln Gln Met Lys Arg Lys Glu Lys Leu Thr Leu Thr Ser
                530                 535                 540

Lys Thr Thr Thr Thr Leu Cys Leu His Tyr Leu Ala Gln Ala Leu Gln
545                 550                 555                 560

Ala Gln Pro Leu Gly Pro Gln Leu Arg Asp Leu Cys Ser Leu Ala Ala
                565                 570                 575

Glu Gly Ile Trp Gln Lys Lys Thr Leu Phe Ser Pro Asp Asp Leu Arg
                580                 585                 590

Lys His Gly Leu Asp Gly Ala Ile Ile Ser Thr Phe Leu Lys Met Gly
                595                 600                 605

Ile Leu Gln Glu His Pro Ile Pro Leu Ser Tyr Ser Phe Ile His Leu
                610                 615                 620
```

```
Cys Phe Gln Glu Phe Phe Ala Ala Met Ser Tyr Val Leu Glu Asp Glu
625                 630                 635                 640

Lys Gly Arg Gly Lys His Ser Asn Cys Ile Ile Asp Leu Glu Lys Thr
            645                 650                 655

Leu Glu Ala Tyr Gly Ile His Gly Leu Phe Gly Ala Ser Thr Thr Arg
            660                 665                 670

Phe Leu Leu Gly Leu Leu Ser Asp Glu Gly Glu Arg Glu Met Glu Asn
            675                 680                 685

Ile Phe His Cys Arg Leu Ser Gln Gly Arg Asn Leu Met Gln Trp Val
            690                 695                 700

Pro Ser Leu Gln Leu Leu Leu Gln Pro His Ser Leu Glu Ser Leu His
705                 710                 715                 720

Cys Leu Tyr Glu Thr Arg Asn Lys Thr Phe Leu Thr Gln Val Met Ala
            725                 730                 735

His Phe Glu Glu Met Gly Met Cys Val Glu Thr Asp Met Glu Leu Leu
            740                 745                 750

Val Cys Thr Phe Cys Ile Lys Phe Ser Arg His Val Lys Lys Leu Gln
            755                 760                 765

Leu Ile Glu Gly Arg Gln His Arg Ser Thr Trp Ser Pro Thr Met Val
770                 775                 780

Val Leu Leu Ala Gly Cys Gly Leu Thr Ala Glu Asp Cys Lys Asp Leu
785                 790                 795                 800

Ala Phe Gly Leu Arg Ala Asn Gln Thr Leu Thr Glu Leu Asp Leu Ser
            805                 810                 815

Phe Asn Val Leu Thr Asp Ala Gly Ala Lys His Leu Cys Gln Arg Leu
            820                 825                 830

Arg Gln Pro Ser Cys Lys Leu Gln Arg Leu Gln Leu Val Ser Cys Gly
            835                 840                 845

Leu Thr Ser Asp Cys Cys Gln Asp Leu Ala Ser Val Leu Ser Ala Ser
850                 855                 860

Pro Ser Leu Lys Glu Leu Asp Leu Gln Gln Asn Asn Leu Asp Asp Val
865                 870                 875                 880

Gly Val Arg Leu Leu Cys Glu Gly Leu Arg His Pro Ala Cys Lys Leu
            885                 890                 895

Ile Arg Leu Gly Leu Asp Gln Thr Thr Leu Ser Asp Glu Met Arg Gln
            900                 905                 910

Glu Leu Arg Ala Leu Glu Gln Glu Lys Pro Gln Leu Leu Ile Phe Ser
            915                 920                 925

Arg Arg Lys Pro Ser Val Met Thr Pro Thr Glu Gly Leu Asp Thr Gly
            930                 935                 940

Glu Met Ser Asn Ser Thr Ser Ser Leu Lys Arg Gln Arg Leu Gly Ser
945                 950                 955                 960

Glu Arg Ala Ala Ser His Val Ala Gln Ala Asn Leu Lys Leu Leu Asp
            965                 970                 975

Val Ser Lys Ile Phe Pro Ile Ala Glu Ile Ala Glu Glu Ser Ser Pro
            980                 985                 990

Glu Val Val Pro Val Glu Leu Leu  Cys Val Pro Ser Pro  Ala Ser Gln
            995                 1000                1005

Gly Asp  Leu His Thr Lys Pro  Leu Gly Thr Asp Asp  Asp Phe Trp
            1010                1015                1020

Gly Pro  Thr Gly Pro Val Ala  Thr Glu Val Val Asp  Lys Glu Lys
            1025                1030                1035
```

-continued

```
Asn Leu Tyr Arg Val His Phe Pro Val Ala Gly Ser Tyr Arg Trp
1040                1045                1050

Pro Asn Thr Gly Leu Cys Phe Val Met Arg Glu Ala Val Thr Val
1055                1060                1065

Glu Ile Glu Phe Cys Val Trp Asp Gln Phe Leu Gly Glu Ile Asn
1070                1075                1080

Pro Gln His Ser Trp Met Val Ala Gly Pro Leu Leu Asp Ile Lys
1085                1090                1095

Ala Glu Pro Gly Ala Val Glu Ala Val His Leu Pro His Phe Val
1100                1105                1110

Ala Leu Gln Gly Gly His Val Asp Thr Ser Leu Phe Gln Met Ala
1115                1120                1125

His Phe Lys Glu Glu Gly Met Leu Leu Glu Lys Pro Ala Arg Val
1130                1135                1140

Glu Leu His His Ile Val Leu Glu Asn Pro Ser Phe Ser Pro Leu
1145                1150                1155

Gly Val Leu Leu Lys Met Ile His Asn Ala Leu Arg Phe Ile Pro
1160                1165                1170

Val Thr Ser Val Val Leu Leu Tyr His Arg Val His Pro Glu Glu
1175                1180                1185

Val Thr Phe His Leu Tyr Leu Ile Pro Ser Asp Cys Ser Ile Arg
1190                1195                1200
```